(12) United States Patent
Mahfouz et al.

(10) Patent No.: US 11,584,936 B2
(45) Date of Patent: Feb. 21, 2023

(54) TARGETED VIRAL-MEDIATED PLANT GENOME EDITING USING CRISPR /CAS9

(71) Applicant: KING ABDULLAH UNIVERSITY OF SCIENCE AND TECHNOLOGY, Thuwal (SA)

(72) Inventors: Magdy M. Mahfouz, Thuwal (SA); Zahir Ali, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 15/317,283

(22) PCT Filed: Jun. 12, 2015

(86) PCT No.: PCT/IB2015/001202
§ 371 (c)(1),
(2) Date: Dec. 8, 2016

(87) PCT Pub. No.: WO2015/189693
PCT Pub. Date: Dec. 17, 2015

(65) Prior Publication Data
US 2017/0114351 A1    Apr. 27, 2017

Related U.S. Application Data

(60) Provisional application No. 62/014,309, filed on Jun. 19, 2014, provisional application No. 62/011,124, filed on Jun. 12, 2014.

(51) Int. Cl.
*C12N 15/82* (2006.01)
*C12N 9/22* (2006.01)

(52) U.S. Cl.
CPC ........... *C12N 15/8203* (2013.01); *C12N 9/22* (2013.01); *C12N 15/8213* (2013.01); *C12N 15/8261* (2013.01); *Y02A 40/146* (2018.01)

(58) Field of Classification Search
None
See application file for complete search history.

(56) References Cited

U.S. PATENT DOCUMENTS

| | | |
|---|---|---|
| 5,107,065 A | 4/1992 | Shewmaker |
| 5,316,931 A | 5/1994 | Donson |
| 5,380,831 A | 1/1995 | Adang |
| 5,436,391 A | 7/1995 | Fujimoto |
| 5,889,190 A * | 3/1999 | Donson ................ C07K 14/005 435/235.1 |
| 7,229,829 B2 * | 6/2007 | Dinesh Kumar .. C12N 15/8203 435/468 |
| 2015/0082478 A1 * | 3/2015 | Cigan .................... C12N 15/81 800/270 |
| 2015/0167000 A1 * | 6/2015 | Voytas ............... C12N 15/8203 435/469 |
| 2015/0225734 A1 * | 8/2015 | Voytas ................. C12N 15/902 435/468 |
| 2016/0237451 A1 * | 8/2016 | Voytas ..................... C12N 9/22 |

FOREIGN PATENT DOCUMENTS

| | | | |
|---|---|---|---|
| WO | 87/06261 | 10/1987 | |
| WO | 8706261 | 10/1987 | |
| WO | WO2013192278 | * 12/2013 | ............. C12N 15/11 |
| WO | WO 2013192278 A1 | 12/2013 | |
| WO | WO 2014186686 A2 | 11/2014 | |

OTHER PUBLICATIONS

Zaidi et al. Viral Vectors for Plant Genome Engineering. Frontiers in Plant Science, 8(539): 1-6 (2017). (Year: 2017).*
Vainstein et al. Permanent genome modifications in plant cells by transient viral vectors. Trends Biotechnol. Aug. 2011;29(8):363-9. Epub Apr. 30, 2011. (Year: 2011).*
Marton et al. Nontransgenic genome modification in plant cells. Plant Physiol. Nov. 2010;154(3):1079-87. Epub Sep. 27, 2010. (Year: 2010).*
Gratz et al. Genome engineering of *Drosophila* with the CRISPR RNA-guided Cas9 nuclease. Genetics. Aug. 2013;194(4):1029-35. Epub May 24, 2013. (Year: 2013).*
Bassett et al. Highly efficient targeted mutagenesis of *Drosophila* with the CRISPR/Cas9 system. Cell Rep. Jul. 11, 2013;4(1):220-8. Epub Jul. 1, 2013. (Year: 2013).*

(Continued)

*Primary Examiner* — Cynthia E Collins
(74) *Attorney, Agent, or Firm* — PABST Patent Group LLP

(57) ABSTRACT

The present disclosure provides a viral-mediated genome-editing platform that facilitates multiplexing, obviates stable transformation, and is applicable across plant species. The RNA2 genome of the tobacco rattle virus (TRV) was engineered to carry and systemically deliver a guide RNA molecules into plants overexpressing Cas9 endonuclease. High genomic modification frequencies were observed in inoculated as well as systemic leaves including the plant growing points. This system facilitates multiplexing and can lead to germinal transmission of the genomic modifications in the progeny, thereby obviating the requirements of repeated transformations and tissue culture. The editing platform of the disclosure is useful in plant genome engineering and applicable across plant species amenable to viral infections for agricultural biotechnology applications.

20 Claims, 30 Drawing Sheets
Specification includes a Sequence Listing.

(56) References Cited

OTHER PUBLICATIONS

Hwang et al. Efficient genome editing in zebrafish using a CRISPR-Cas system. Nat. Biotechnol. Mar. 2013;31(3):227-9. Epub Jan. 29, 2013. (Year: 2013).*
Chang et al. Genome editing with RNA-guided Cas9 nuclease in zebrafish embryos. Cell Res. Apr. 2013;23(4):465-72. Epub Mar. 26, 2013. (Year: 2013).*
Friedland et al. Heritable genome editing in C. elegans via a CRISPR-Cas9 system. Nat. Methods. Aug. 2013;10(8):741-3. Epub Jun. 30, 2013. (Year: 2013).*
Cong et al. Multiplex genome engineering using CRISPR/Cas systems. Science. Feb. 15, 2013;339(6121):819-23. Epub Jan. 3, 2013. (Year: 2013).*
Mali et al. RNA-guided human genome engineering via Cas9. Science. Feb. 15, 2013;339(6121):823-6. Epub Jan. 3, 2013. (Year: 2013).*
Cho et al. Targeted genome engineering in human cells with the Cas9 RNA-guided endonuclease. Nat. Biotechnol. Mar. 2013;31(3):230-2. Epub Jan. 29, 2013. (Year: 2013).*
Jinek et al. RNA-programmed genome editing in human cells. Elife. Jan. 29, 2013;2:e00471. (Year: 2013).*
DiCarlo et al. Genome engineering in *Saccharomyces cerevisiae* using CRISPR-Cas systems. Nucleic Acids Res. Apr. 2013;41(7):4336-43. Epub Mar. 4, 2013. (Year: 2013).*
Shan et al. Targeted genome modification of crop plants using a CRISPR-Cas system. Nat. Biotechnol. Aug. 2013;31(8):686-8. (Year: 2013).*
Nekrasov et al. Targeted mutagenesis in the model plant *Nicotiana benthamiana* using Cas9 RNA-guided endonuclease. Nat. Biotechnol. Aug. 2013;31(8):691-3. (Year: 2013).*
Xie et al. RNA-guided genome editing in plants using a CRISPR-Cas system. Mol. Plant. Nov. 2013;6(6):1975-83. Epub Aug. 17, 2013. (Year: 2013).*
Jiang et al. Demonstration of CRISPR/Cas9/sgRNA-mediated targeted gene modification in *Arabidopsis*, tobacco, sorghum and rice. Nucleic Acid Res. Nov. 2013;41(20):e188. Epub Sep. 2, 2013. (Year: 2013).*
Upadhyay et al. RNA-guided genome editing for target gene mutations in wheat. G3 (Bethesda) Dec. 9, 2013;3(12):2233-8. (Year: 2013).*
Liu et al. CRISPR-Cas system: a powerful tool for genome engineering. Plant Mol. Biol. Jun. 2014;85(3):209-18. Epub Mar. 18, 2014. (Year: 2014).*
Lozano-Juste et al. Plant genome engineering in full bloom. Trends Plant Sci. May 2014;19(5):284-7. Epub Mar. 24, 2014. (Year: 2014).*
Jia et al. Targeted genome editing of sweet orange using Cas9/sgRNA. PLOS One. Apr. 7, 2014;9(4):e93806. eCollection 2014. (Year: 2014).*
Xu et al. Gene targeting using the Agrobacterium tumefaciens-mediated CRISPR-Cas system in rice. Rice (NY). May 2, 2014;7(1):5. eCollection 2014. (Year: 2014).*
Zhang et al. The CRISPR/Cas9 system produces specific and homozygous targeted gene editing in rice in one generation. Plant Biotechnol. J. Aug. 2014;12(6):797-807. Epub May 23, 2014. (Year: 2014).*
Jiang et al. Efficient CRISPR/Cas9-mediated gene editing in *Arabidopsis thaliana* and inheritance of modified genes in the T2 and T3 generations. PloS One. Jun. 11, 2014;9(6):e99225.. eCollection 2014. (Year: 2014).*
Fauser et al. Both CRISPR/Cas-based nucleases and nickases can be used efficiently for genome engineering in *Arabidopsis thaliana*. Plant J. Jul. 2014;79(2):348-59. Published online May 16, 2014. (Year: 2014).*
Feng et al. Multigeneration analysis reveals the inheritance, specificity, and patterns of CRISPR/Cas-induced gene modifications in *Arabidopsis*. Proc. Natl. Acad. Sci. USA. Mar. 25, 2014;111(12):4632-7. Epub Feb. 18, 2014. (Year: 2014).*

Li et al. Multiplex and homologous recombination-mediated genome editing in *Arabidopsis* and Nicotiana benthamiana using guide RNA and Cas9. Nat. Biotechnol. Aug. 2013;31(8):688-91. (Year: 2013).*
Fichtner et al. Precision genetic modifications: a new era in molecular biology and crop improvement. Planta. Apr. 2014;239(4):921-39. Epub Feb. 8, 2014. (Year: 2014).*
Swanson et al. The E116 isolate of Dutch pea early-browning virus is a recombinant virus. Virus Research 60 (1999) 87-94. (Year: 1999).*
Goulden et al. The complete nucleotide sequence of PEBV RNA2 reveals the presence of a novel open reading frame and provides insights into the structure of tobaviral subgenomic promoters. Nucleic Acids Research, 1990, vol. 18, No. 15, 4507-4512. (Year: 1990).*
International Search Report and Written Opinion of Application No. PCT/IB2015/001202 dated Oct. 20, 2015, 15 pages.
Jian-Feng Li et al: "Multiplex and homologous recombination-mediated genome editing in *Arabidopsis* and Nicotiana benthamiana using guide RNA and Cas9", Nature Biotechnoogy, vol. 31, Jan. 1, 2013, pp. 388-691, XP055129103.
W. Jiang et al: "Demonstration of CRISPR/Cas9/sgRNA-mediated targeted gene modification in *Arabidopsis*, tobacco, sorghum and rice", Nucleic Acids Research, vol. 41, No. 20, Sep. 2, 2013, pp. e188-e188, XP055219328.
Wenzhi Jiang et al: "Efficient CRISPR/Cas9-Mediated Gene Editing in *Arabidopsis thaliana* and Inheritance of Modified Genes in the T2 and T3 Generations", PLOS ONE, vol. 9, No. 6, Jun. 11, 2014, p. e99225, XP055219594.
Muthappa Senthil-Kumar et al: "Tobacco rattle virus-based virus-induced gene silencing in Nicotiana benthamiana", Nature Protocols, vol. 9, No. 7, Jun. 5, 2014, pp. 1549-1562, XP055219608.
Franziska Fichtner et al: "Precision genetic modifications: a new era in molecular biology and crop improvement", PLANTA, vol. 239, No. 4, Apr. 1, 2014, pp. 921-939, XP055219342.
M. Jinek et al: "A Programmable Dual-RNA-Guided DNA Endonuclease in Adaptive Bacterial Immunity", SCIENCE, vol. 337, No. 6096, Aug. 17, 2012, pp. 816-821, XP055067740.
Ali, et al., "Activity and specificity of TRV-mediated gene editing in plants", *Plant Signal Behav.*, 10(10):e1044191-5 (2015a).
Ali, et al., "CRISPR/Cas9-mediated Viral Interference in Plants", *Genome Biol.*, 16(238):1-11 (2015b).
Ali, et al., "Efficient Virus-Mediated Genome Editing in Plants Using the CRISPR/Cas9 System", *Mol. Plant.*, 8(8):1288-91 (2015c).
Aouida, et al., "Activities and specificities of homodimeric TALENs in *Saccharomyces cerevisiae*," *Curr Genet*, 60, 61-74 (2014).
Baltes, et al., "DNA Replicons for Plant Genome Engineering", *Plant Cell*, 26: 151-163 (2014).
Brunt & Stace-Smith, "Some hosts, propertied and possible affinities of a labile virus from Hypochoeris radicata (Compositae)", *Ann. Appl. Biol.*, 90: 205-214 (1978).
Cong, et al., "Multiplex Genome Engineering Using CRISPR/Cas Systems", *Science*, 339: 819-823 (2013).
Dinesh-Kumar, et al., "Virus-induced Gene Silencing", *Meth. Mol. Biol.*, 236: 287-294 (2003).
Feng, et al., "Multigeneration Analysis Reveals the Inheritance, Specificity, and Patterns of CRISPR/Cas-induced Gene Modifications in *Arabidopsis*", *Proc. Natl. Acad. Sci.*, 111:4632-4637 (2014).
Fauser, et al., "Both CRISPR/Cas-based nucleases and nickases can be used efficiently for genome engineering in *Arabidopsis thaliana*", *Plant J*, 79, 348-359 (2014).
GenBank Accession No. AF406990, 4 pages, accessed May 26, 2020.
GenBank Accession No. AF406991, 3 pages, accessed May 26, 2020.
GenBank Accession No. AY179605, 1 page, accessed May 26, 2020.
Gluzman et al., Communications in Molecular Biology: Viral Vectors, Cold Spring Harbor Laboratory, New York, pp. 172-189 (1988).
Groenen, et al., "Nature of DNA Polymorphism in the Direct Repeat Cluster of *Mycobacterium tuberculosis*; Application for Strain Differentiation by a Novel Typing Method", *Mol. Microbial.*, 10: 1057-1065 (1993).

(56) References Cited

OTHER PUBLICATIONS

Haft, et al., "A Guild of 45 CRISPR-associated (Cas) Protein Families and Multiple CRISPR/Cas Subtypes Exist in Prokaryotic Genomes", *Computational Biology*, PLoS Comput. Biol. 1(e60):0474-0483 (2005).
Harrison, et al, "Comparison of nucleic acid hybridisation and other tests for detecting tobacco rattle virus in narcissus plants and potato tubers", *Ann. Appl. Biol.*, 102: 331-338 (1983).
Hoe, et al., "Rapid Molecular Genetic subtyping of Serotype M1 Group A *Streptococcus* Strains", *Emerg. Infect. Dis.*, 5: 254-263 (1999).
Honig, et al., "Transient expression of virally delivered meganuclease in planta generates inherited genomic deletions", *Mol. Plant*, 8:1292-1294 (2015).
Ishino, et al., "Nucleotide Sequence of the Iap Gene, Responsible for Alkaline Phosphates Isozyme Conversion in *Escherichia coli*, and Identification of the Gene Product", *J. Bacteriol.*, 169: 5429-5433 (1987).
Jansen, et al., "Identification of Genes That Are Associated with DNA Repeats in Prokaryotes", *Mol. Microbial.*, 43:1565-1575 (2002).
Janssen, et al., "Identification of a Novel Family off Sequence Repeats Among Prokaryotes", *OMICS J. Integ. Biol.*, 6:23-33 (2002).
Kuscu, et al., "Genome-wide analysis reveals characteristics of off-target sites bound by the Cas9 endonuclease," *Nat. Biotechnol.*, 32:677-683 (2014).
Li, et al., "Characterization and DNA-binding Specificities of Ralstonia TAL-like Effectors", *Mol. Plant*, 6:1318-1330 (2013b).
Liu, et al., "Virus-induced gene silencing in tomato", *Plant J.*, 31:777-786 (2002).
MacFarlane, "Tobraviruses-plant pathogens and tools for biotechnology," *Mol. Plant Pathol.*, 11:577-583 (2011).
Mahas, et al., "Virus-Mediated Genome Editing in Plants Using the CRISPR/Cas9 System", *Methods Mol Biol.*, 1917:311-326 (2019).
Mahfouz, et al., "Genome Engineering via TALENs and CRISPR/Cas9 Systems: Challenges and Perspectives", *Plant Biotechnol J.*, 12(8):1006-1014 (2012).
Mali, et al., "RNA-Guided Human Genome Engineering via Cas9", *Science*, 339:823-826 (2013).
Martin-Hernandez and Baulcombe, "Tobacco Rattle Virus 16-kilodalton Protein Encodes a Suppressor of RNA Silencing That Allows Transient Viral Entry in Meristems", *J. Virol.*, 82: 4064-4071 (2008).
Marton, et al., "Nontransgenic Genome Modification in Plant Cells", *Plant Physiol.*, 154:1079-1087 (2010).
Masepohl, et al., "Long Tandemly Repeated Repetitive (LTRR) Sequences in the Filamentous Cyanobacterium *Anabaena* Sp. PCC 7120", *Biochim. Biophys. Acta.*, 1307: 26-30 (2010).
Mojica, et al., "Long Stretches of Short Tandem repeats Are Present in the Largeset Replicons of the Archaea Haloferax Mediterranei and Haloferax Volcanii and Could Be Involved in Relpicon Particioning", *Mol. Microbial.*, 17:85-93 (1995).
Mojica, et al., "Biological Significance of a Family of Regularly Spaced Repeats in the Genomes of Archaea, Bacteria and Mitochondria", *Mol. Microbiol.*, 36: 244-246 (2000).
Nakamura, et al., "Codon Usage Tabulated From International DNA Sequence Databases: Status for the Year 2000", *Nucl. Acids Res.*, 28:292 (2000).
Nakata, et al., "Unusual Nucleotide Arrangement with Repeated Sequences in the *Escherichia coli* K-12 Chromosome", *J. Bacteriol.*, 171: 3553-3556 (1989).
Nekrasov, et al., "Targeted Mutagenesis in the Model Plant Nicotiana Benthamiana Using Cs9 RNA-guided Endonuclease", *Nature Biotechnol.*, 31: 691-693 (2013).
Pennisi, "Sowing the Seeds for the Ideal Crop", *Science*, 327: 802-803 (2010).
Piatek, et al., "RNA-guided transcriptional regulation in planta via synthetic dCas9-based transcription factors," *Plant Biotechnol J.*, 13(4):578-89 (2014).
Puchta, et al., "Synthetic Nucleases for Gnome Engineering in Plants: Prospects for a Bright Future", *Plant J.*, 78: 727-741 (2014).
Ratcliff, et al., "Technical Advance. Tobacco Rattle Virus as a Vector for Analysis of Gene Function by Silencing", *Plant J.*, 25: 237-245 (2014).
Shan, et al., "Targeted Genome Modification of Crop Plants Using a CRISPR-Cas System", *Nature Biotechnol.*, 31: 686-688 (2013).
Shukla, et al., "Precise Genome Modification in the Crop species *Zea mays* Using Zinc-Finger Nucleases", *Nature*, 459: 437-441 (2009).
UniProt Accession No. Q99ZW2, 13 pages, accessed May 29, 2020.
Townsend, et al., "High-frequency Modification of Plant Genes Using Engineered Zinc-Finger Nucleases", *Nature*, 459: 442-445 (2009).
Van Embden, et al., "Genetic Variation and evolutionary Origin of the Direct Repeat Locus of *Mycobacterium tuberculosis* Complex Bacteria", *J. Bacteriol.*, 182:2393-2401 (2000).
Voytas, "Plant Genome Engineering with Sequence-Specific Nucleases", *Ann. Rev. Plant Biol.*, 64: 327-350 (2013).
Wu, et al., "Genome-wide binding of the CRISPR endonuclease Cas9 in mammalian cells," *Nat. Biotechnol.*, 32:670-676 (2014).
Zhang, et al., "The CRISPR/Cas9 system produces specific and homozygous targeted gene editing in rice in one generation", *Plant Biotechnol J.*, 12:797-807 (2014).
Groenen, et al., "Nature of DNA Polymorphism in the Direct Repeat Cluster of *Mycobacterium tuberculosis*; Application for Strain Differentiation by a Novel Typing Method", Mol. Microbiol., 10: 1057-1065 (1993).
Jansen, et al., "Identification of Genes That Are Associated With DNA Repeats in Prokaryotes", Mol. Microbiol., 43:1565-1575 (2002).
Janssen, et al., "Identification of a Novel Family of Sequence Repeats Among Prokaryotes", OMICS J. Integ. Biol., 6:23-33 (2002).
Mojica, et al., "Long Stretches of Short Tandem repeats Are Present in the Largest Replicons of the Archaea Haloferax Mediterranei and Haloferax Volcanii and Could Be Involved in Relpicon Particioning", Mol. Microbiol., 17:85-93 (1995).
Gluzman, et al., Communications in Molecular Biology: Viral Vectors, Cold Spring Harbor Laboratory, New York, pp. 172-189 (1988). (2 page Book Review/Summary).
Jansen, et al., "Identification of a Novel Family of Sequence Repeats Among Prokaryotes", OMICS J. Integ. Biol., 6:23-33 (2002b).

\* cited by examiner

```
                                    NcoI PAM
pds3    GTTATGTTTTGGTAGTAGCGACTCCA TGGGGCATAAGTTTTAGAATTCGT       (SEQ ID NO: 123)
08_B11  GTTATGTTTTGGTAGTAGC        TGGGGCATAAGTTTTAGAATTCGT  -7   (SEQ ID NO: 124)
10_D11  GTTATGTTTTGGTAGTAGC       A TGGGGCATAAGTTTTAGAATTCGT -6   (SEQ ID NO: 125)
12_F11  GTTATGTTTTGGTAGTAGCGA     A TGGGGCATAAGTTTTAGAATTCGT  -4  (SEQ ID NO: 126)
19_E12  GTTATGTTTTGGTAGTAGCGAC    A TGGGGCATAAGTTTTAGAATTCGT  -3  (SEQ ID NO: 127)
22_H12  GTTATGTTTTGGTAGTAGCGACTC  A TGGGGCATAAGTTTTAGAATTCGT  -1  (SEQ ID NO: 128)
11_E11  GTTATGTTTTGGTAGTAGCGACTCCAATGGGGCATAAGTTTTAGAATTCGT  +1A (SEQ ID NO: 129)
```

Fig. 1C

```
                                    NcoI PAM
pds3    GTTATGTTTTGGTAGTAGCGACTCC ATGGGGCATAAGTTTTAGAATTCGT       (SEQ ID NO: 123)
12_D06  GTTATGTTTTGGTAGTAGCGACTCC  GGGGCATAAGTTTTAGAATTCGT   -1   (SEQ ID NO: 130)
08_H05  GTTATGTTTTGGTAGTAGCGA      GGCATAAGTTTTAGAATTCGT     -7   (SEQ ID NO: 131)
10_B06  GTTATGTTTTGGTAGTAGCGA     ATGGGGCATAAGTTTTAGAATTCGT  -4   (SEQ ID NO: 132)
09_A06  GTTATGTTTTGGTAGTAGCGAC    ATGGGGCATAAGTTTTAGAATTCGT  -3   (SEQ ID NO: 133)
30_F08  GTTATGTTTTGGTAGTAGCGACTCC  TGGGGCATAAGTTTTAGAATTCGT  -1   (SEQ ID NO: 134)
05_E05  GTTATGTTTTGGTAGTAGCGACTC   ATGGGGCATAAGTTTTAGAATTCGT -1   (SEQ ID NO: 135)
20_D07  GTTATGTTTTGGTAGTAGCGACTCCAATGGGGCATAAGTTTTAGAATTCGT  +1A  (SEQ ID NO: 136)
```

Fig. 1D

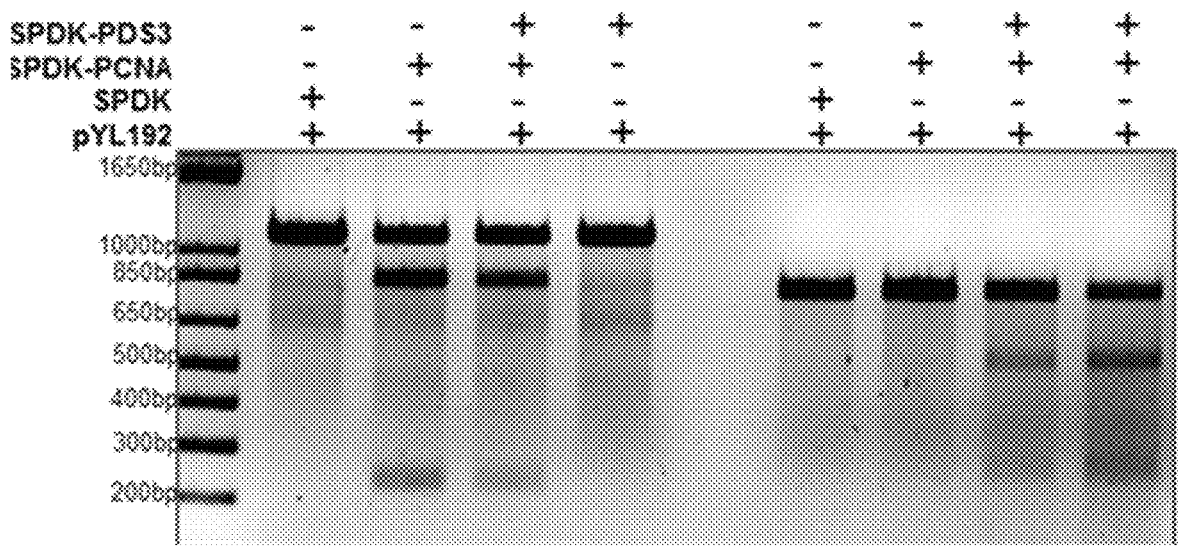
Fig. 2C
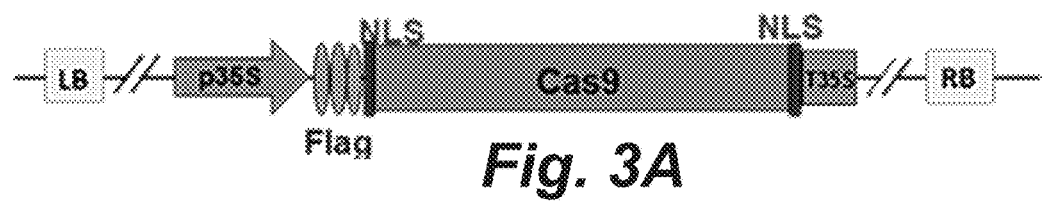
Fig. 3A
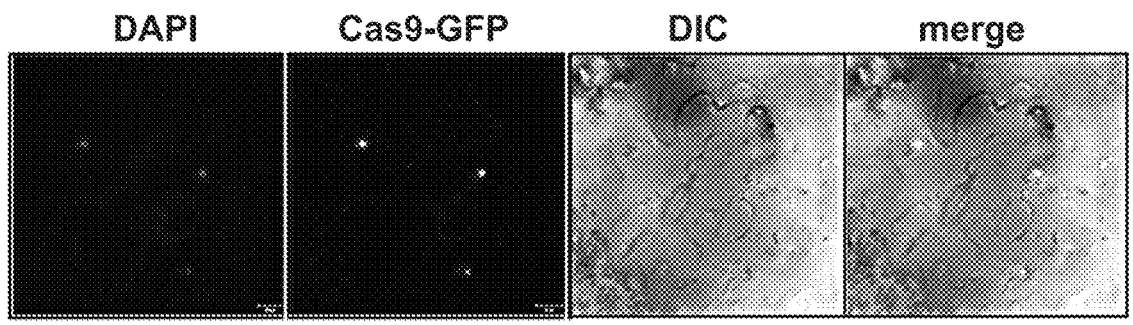
Fig. 3B

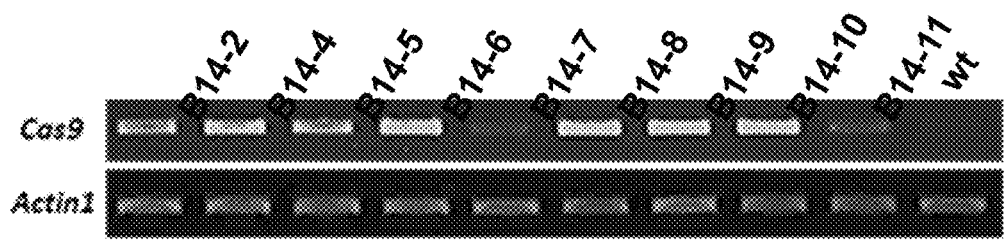
*Fig. 3C*
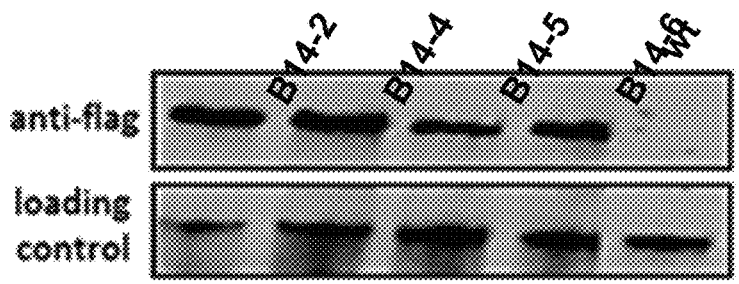
*Fig. 3D*
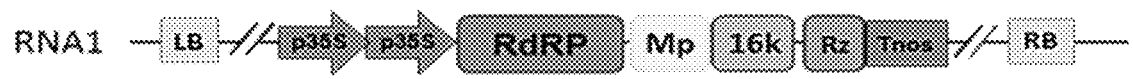
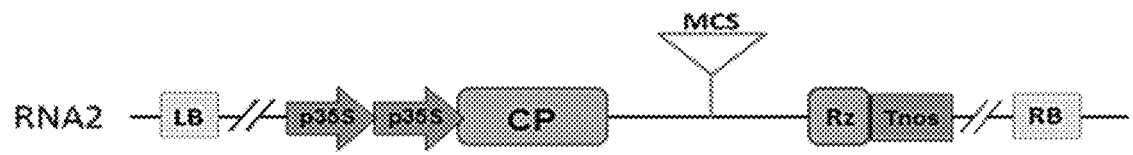
*Fig. 4A*

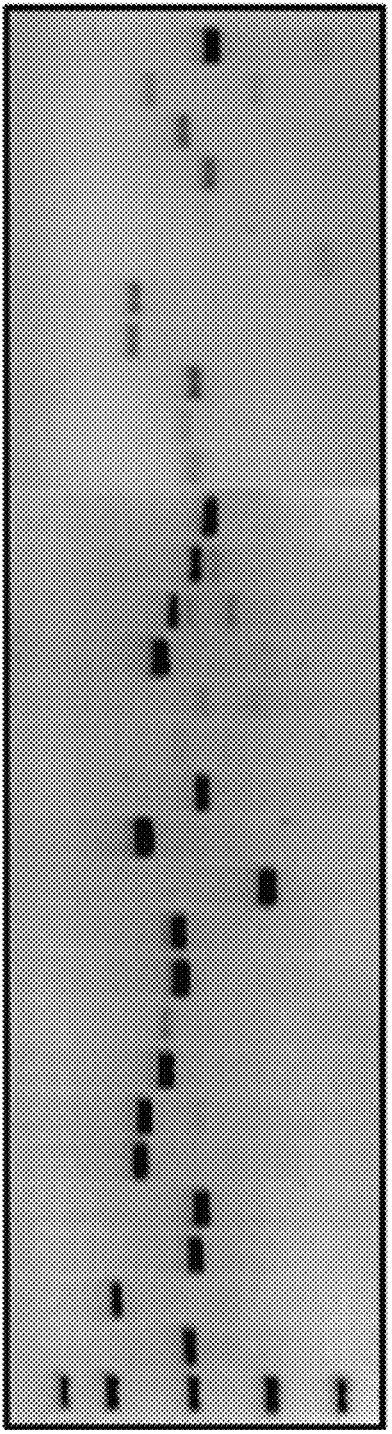
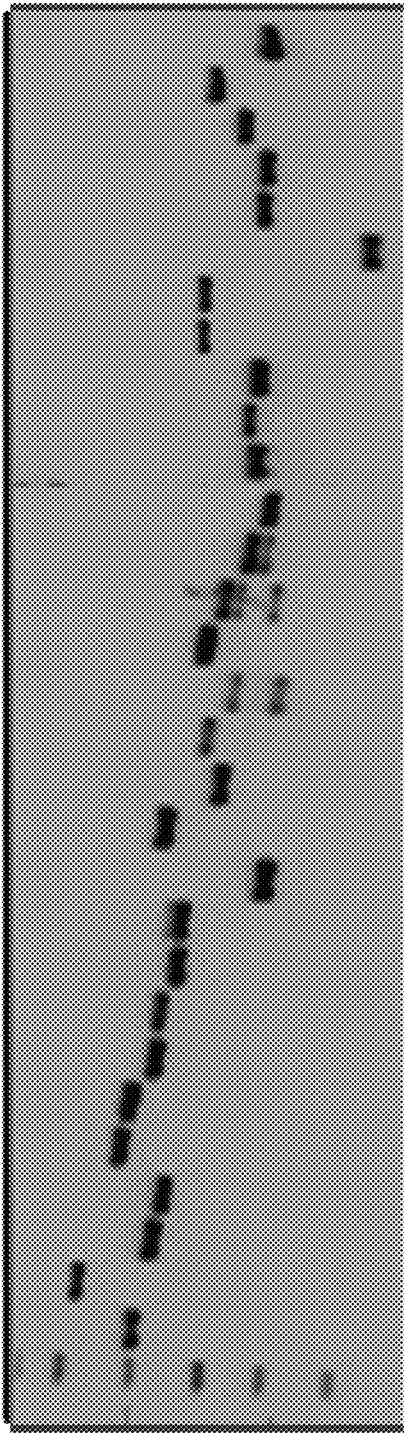
Fig. 12A
Fig. 12B

Cas9 sequence (flag-nls-cas9-nls)(SEQ ID NO: 1)
ATGGACTATAAGGACCACGACGGAGACTACAAGGATCATGATATTGATTACAAAGACGATGACGATAAGA
TGGCCCCAAAGAAGAAGCGGAAGGTCGGTATCCACGGAGTCCCAGCAGCCGACAAGAAGTACAGCATCGG
CCTGGACATCGGCACCAACTCTGTGGGCTGGGCCGTGATCACCGACGAGTACAAGGTGCCCAGCAAGAAA
TTCAAGGTGCTGGGCAACACCGACCGGCACAGCATCAAGAAGAACCTGATCGGAGCCCTGCTGTTCGACA
GCGGCGAAACAGCCGAGGCCACCCGGCTGAAGAGAACCGCCAGAAGAAGATACACCAGACGGAAGAACCG
GATCTGCTATCTGCAAGAGATCTTCAGCAACGAGATGGCCAAGGTGGACGACAGCTTCTTCCACAGACTG
GAAGAGTCCTTCCTGGTGGAAGAGGATAAGAAGCACGAGCGGCACCCCATCTTCGGCAACATCGTGGACG
AGGTGGCCTACCACGAGAAGTACCCCACCATCTACCACCTGAGAAAGAAACTGGTGGACAGCACCGACAA
GGCCGACCTGCGGCTGATCTATCTGGCCCTGGCCCACATGATCAAGTTCCGGGGCCACTTCCTGATCGAG
GGCGACCTGAACCCCGACAACAGCGACGTGGACAAGCTGTTCATCCAGCTGGTGCAGACCTACAACCAGC
TGTTCGAGGAAAACCCCATCAACGCCAGCGGCGTGGACGCCAAGGCCATCCTGTCTGCCAGACTGAGCAA
GAGCAGACGGCTGGAAAATCTGATCGCCCAGCTGCCCGGCGAGAAGAAGAATGGCCTGTTCGGAAACCTG
ATTGCCCTGAGCCTGGGCCTGACCCCAACTTCAAGAGCAACTTCGACCTGGCCGAGGATGCCAAACTGC
AGCTGAGCAAGGACACCTACGACGACGACCTGGACAACCTGCTGGCCCAGATCGGCGACCAGTACGCCGA
CCTGTTCCTGGCCGCCAAGAACCTGTCCGACGCCATCCTGCTGAGCGACATCCTGAGAGTGAACACCGAG
ATCACCAAGGCCCCCCTGAGCGCCTCTATGATCAAGAGATACGACGAGCACCACCAGGACCTGACCCTGC
TGAAAGCTCTCGTGCGGCAGCAGCTGCCTGAGAAGTACAAAGAGATTTTCTTCGACCAGAGCAAGAACGG
CTACGCCGGCTACATTGACGGCGGAGCCAGCCAGGAAGAGTTCTACAAGTTCATCAAGCCCATCCTGGAA
AAGATGGACGGCACCGAGGAACTGCTCGTGAAGCTGAACAGAGAGGACCTGCTGCGGAAGCAGCGGACCT
TCGACAACGGCAGCATCCCCCACCAGATCCACCTGGGAGAGCTGCACGCCATTCTGCGGCGGCAGGAAGA
TTTTTACCCATTCCTGAAGGACAACCGGGAAAAGATCGAGAAGATCCTGACCTTCCGCATCCCCTACTAC
GTGGGCCCTCTGGCCAGGGGAAACAGCAGATTCGCCTGGATGACCAGAAAGAGCGAGGAAACCATCACCC
CCTGGAACTTCGAGGAAGTGGTGGACAAGGGCGCTTCCGCCCAGAGCTTCATCGAGCGGATGACCAACTT
CGATAAGAACCTGCCCAACGAGAAGGTGCTGCCCAAGCACAGCCTGCTGTACGAGTACTTCACCGTGTAT
AACGAGCTGACCAAAGTGAAATACGTGACCGAGGGAATGAGAAAGCCCGCCTTCCTGAGCGGCGAGCAGA
AAAAGGCCATCGTGGACCTGCTGTTCAAGACCAACCGGAAAGTGACCGTGAAGCAGCTGAAAGAGGACTA
CTTCAAGAAAATCGAGTGCTTCGACTCCGTGGAAATCTCCGGCGTGGAAGATCGGTTCAACGCCTCCCTG
GGCACATACCACGATCTGCTGAAAATTATCAAGGACAAGGACTTCCTGGACAATGAGGAAAACGAGGACA
TTCTGGAAGATATCGTGCTGACCCTGACACTGTTTGAGGACAGAGAGATGATCGAGGAACGGCTGAAAAC
CTATGCCCACCTGTTCGACGACAAAGTGATGAAGCAGCTGAAGCGGCGGAGATACACCGGCTGGGGCAGG
CTGAGCCGGAAGCTGATCAACGGCATCCGGGACAAGCAGTCCGGCAAGACAATCCTGGATTTCCTGAAGT
CCGACGGCTTCGCCAACAGAAACTTCATGCAGCTGATCCACGACGACAGCCTGACCTTTAAAGAGGACAT
CCAGAAAGCCCAGGTGTCCGGCCAGGGCGATAGCCTGCACGAGCACATTGCCAATCTGGCCGGCAGCCCC
GCCATTAAGAAGGGCATCCTGCAGACAGTGAAGGTGGTGGACGAGCTCGTGAAAGTGATGGGCCGGCACA
AGCCCGAGAACATCGTGATCGAAATGGCCAGAGAGAACCAGACCACCCAGAAGGGACAGAAGAACAGCCG
CGAGAGAATGAAGCGGATCGAAGAGGGCATCAAGGAGCTGGGCAGCCAGATCCTGAAAGAACACCCCGTG
GAAAACACCCAGCTGCAGAACGAGAAGCTGTACCTGTACTACCTGCAGAATGGGCGGGATATGTACGTGG
ACCAGGAACTGGACATCAACCGGCTGTCCGACTACGATGTGGACCATATCGTGCCTCAGAGCTTTCTGAA
GGACGACTCCATCGACAACAAGGTGCTGACCAGAAGCGACAAGAACCGGGGCAAGAGCGACAACGTGCCC
TCCGAAGAGGTCGTGAAGAAGATGAAGAACTACTGGCGGCAGCTGCTGAACGCCAAGCTGATTACCCAGA
GAAAGTTCGACAATCTGACCAAGGCCGAGAGAGGCGGCCTGAGCGAACTGGATAAGGCCGGCTTCATCAA
GAGACAGCTGGTGGAAACCCGGCAGATCACAAAGCACGTGGCACAGATCCTGGACTCCCGGATGAACACT
AAGTACGACGAGAATGACAAGCTGATCCGGGAAGTGAAAGTGATCACCCTGAAGTCCAAGCTGGTGTCCG
ATTTCCGGAAGGATTTCCAGTTTTACAAAGTGCGCGAGATCAACAACTACCACCACGCCCACGACGCCTA
CCTGAACGCCGTCGTGGGAACCGCCCTGATCAAAAAGTACCCTAAGCTGGAAAGCGAGTTCGTGTACGGC
GACTACAAGGTGTACGACGTGCGGAAGATGATCGCCAAGAGCGAGCAGGAAATCGGCAAGGCTACCGCCA
AGTACTTCTTCTACAGCAACATCATGAACTTTTTCAAGACCGAGATTACCCTGGCCAACGGCGAGATCCG

*Fig. 14*

```
GAAGCGGCCTCTGATCGAGACAAACGGCGAAACCGGGGAGATCGTGTGGGATAAGGGCCGGGATTTTGCC
ACCGTGCGGAAAGTGCTGAGCATGCCCCAAGTGAATATCGTGAAAAAGACCGAGGTGCAGACAGGCGGCT
TCAGCAAAGAGTCTATCCTGCCCAAGAGGAACAGCGATAAGCTGATCGCCAGAAAGAAGGACTGGGACCC
TAAGAAGTACGGCGGCTTCGACAGCCCCACCGTGGCCTATTCTGTGCTGGTGGTGGCCAAAGTGGAAAAG
GGCAAGTCCAAGAAACTGAAGAGTGTGAAAGAGCTGCTGGGGATCACCATCATGGAAAGAAGCAGCTTCG
AGAAGAATCCCATCGACTTTCTGGAAGCCAAGGGCTACAAAGAAGTGAAAAAGGACCTGATCATCAAGCT
GCCTAAGTACTCCCTGTTCGAGCTGGAAAACGGCCGGAAGAGAATGCTGGCCTCTGCCGGCGAACTGCAG
AAGGGAAACGAACTGGCCCTGCCCTCCAAATATGTGAACTTCCTGTACCTGGCCAGCCACTATGAGAAGC
TGAAGGGCTCCCCCGAGGATAATGAGCAGAAACAGCTGTTTGTGGAACAGCACAAGCACTACCTGGACGA
GATCATCGAGCAGATCAGCGAGTTCTCCAAGAGAGTGATCCTGGCCGACGCTAATCTGGACAAAGTGCTG
TCCGCCTACAACAAGCACCGGGATAAGCCCATCAGAGAGCAGGCCGAGAATATCATCCACCTGTTTACCC
TGACCAATCTGGGAGCCCCTGCCGCCTTCAAGTACTTTGACACCACCATCGACCGGAAGAGGTACACCAG
CACCAAAGAGGTGCTGGACGCCACCCTGATCCACCAGAGCATCACCGGCCTGTACGAGACACGGATCGAC
CTGTCTCAGCTGGGAGGCGACAAAAGGCCGGCGGCCACGAAAAAGGCCGGCCAGGCAAAAAAGAAAAAGt
aa
```

Fig. 14-cont'd

```
sgRNA (NB-PDS3) sequence and map (SEQ ID NO: 2)
TTGGTAGTAGCGACTCCATGGTTTTAGAGCTAGAAATAGCAAGTTAAAATAAGGCTAGTCCGTTATCAAC
TTGAAAAAGTGGCACCGAGTCGGTGCTTTTTTT
```

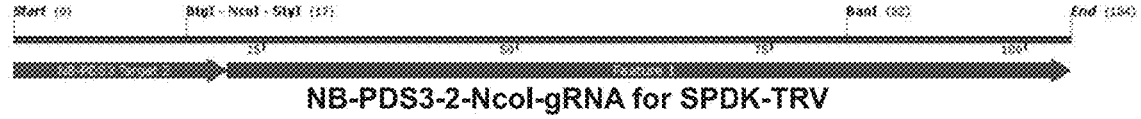

NB-PDS3-2-NcoI-gRNA for SPDK-TRV

Fig. 15

```
NB-PDS3 selected region and map (SEQ ID NO: 3).
Gaaacacatcacctaggcggtttcataccgaggtaacaaatgattttggtttctttggttacatcagctg
aatgctttacttgagaaaagctttctccttttcccgtttaggatcttgtttatttgctttcgtttttcta
ctcgttaaaattttaacttgattttgtgggtgaattataactttactcatagtgcgagaacaagtttcgt
atggactgtaaaagctagaatcttttttacttttgcatataaattgtgtaataaatgcttaagaaccag
aatattgaaaaacaaaggaattctacatagtatttaggttcacaagtgggacaatcttcttacagtgaa
atatctttatgtcaggcttaatttactgctattttgttcagtaaaatgcccaaattggacttgtttctg
ccgttaatttgagagtccaaggtaattcagcttatctttggagctcgaggtcttctttgggaactgaaag
tcaagatggtcgcttgcaaaggaatttgttatgttTTGGTAGTAGCGACTCCATGgggcataagtttaga
attcgtactccagtgccatgaccagaagattgacaaaggacttcaatcctttaaaggttttgttttgaat
gcgaaagtgtgatgctgaatttatgatcacgagcatatattctctaaaataagatatcttgccattcagg
tagtctgcattgattatccaagaccggagctagacaatacagttaactatttggaggcggcgttatcatc
atcatcatttcgtacttcctcacgccc
```

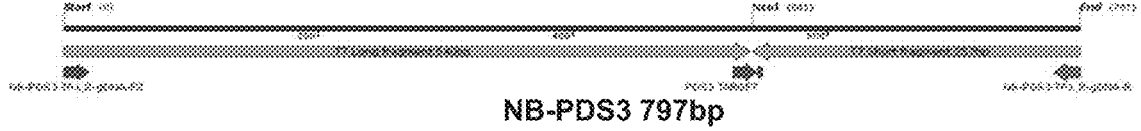

NB-PDS3 797bp

Fig. 16 sgRNA (NB.PCNA) sequence and map (SEQ ID NO: 4)
tgtgaccgtaatatttcaatGTTTTAGAGCTAGAAATAGCAAGTTAAAATAAGGCTAGTCCGTTATCAAC
TTGAAAAAGTGGCACCGAGTCGGTGCTTTTTTT

Fig. 17

NB-PCNA selected region and map (SEQ ID NO: 5)
CCTAACCCTAATTTCCCCAGACCTTCTCAAAGCCCCTTTTTCATAGAAAATGTTGGAATTACGGCTTGTT
CAGGGAAGTCTGCTGAAGAAGGTTCTAGAATCAATTAAGGATCTGGTGAACGATGCGAACTTCGATTGCT
CTGCCACCGGATTCTCTCTGCAGGCCATGGATTCCAGCCACGTAGCGTTGGTGGCGCTGCTGCTCCGATC
TGAGGGTTTTGAGCACTATCGTTGTGACCGTAATATTTCAATGGGGATGAACCTTGGTAACATGGCTAAA
ATGCTCAAATGTGCGGGGAATGATGACATCATCACCCTCAAGGCTGACGATGGCAGTGACACCGTCACTT
TCATGTTTGAAAGCCCCAGTAAGTTCCAAAACTTATTTTTCTTCTGAAGCCTATTTTTTTCGTAAGTTGT
GTAGCATATAAATAAGACCTAGAAACATTGTAAAATTTGTTATGTAAAGTTGCAAATTGTTCATTGCCTT
TCCCAAAATATGTGACCTTTTTTTTGCTTATGATTGCTCTTTTTTAGTACTTTGATATACCTTTTGGTTA
TTTTGACGTGGGAAAAATTGCAGCTAATAGTACTTTTGACAGTCTTTGAATATCTTAGATTTAAATTTTG
AAAATTATTATCTACTGATTCTAAATAATTATAAGTGAAATAAACTTGTTTATTTAGCTCAAAATTTTTA
TAATTGATATTTGATCCAATAGATAAAATTGCAGCTAAATAGTGTTTTTGCAATAGTGTTTGAATATCAA
TGTTAATTTTTTTATAAATTTTAGCTCGGAAGTGATAATATTAAAAAAGTATAAAATAAAAATGAGTTAA
ACTTGTTGATTTAGCTTGGAAGTGATATTATTGACATTTGATACAAGAAATTGGCATTGGCTATTTTCA
TCATAGCGTGTGGTGTTGCGTGTATTAAGCTGAATATATAGTTTTAGAAATTGTGATTTGATTCTGAATT
TGGATTTACTCTACTATTCTTCCATTGTTATGGCTGGGTGTAACTAAGTATACTGTAACGTATCACAGCC
CAAGACAAGATTGCTGATTTTGAGATGAAGCTGATGGACATTGACAGT Consensus_PCNA-our_genomic_tobacco 1098bp

Fig. 18 pYL156 RNA2 complete sequence (SEQ ID NO: 6)
aagcttgcatgcctgcaggtcaacatggtggagcacgacactctcgtctactccaagaatatcaaagata
cagtctcagaagaccagagggctattgagacttttcaacaaagggtaatatcgggaaacctcctcggatt
ccattgcccagctatctgtcacttcatcgaaaggacagtagaaaaggaagatggcttctacaaatgccat
cattgcgataaaggaaaggctatcgttcaagatgcctctaccgacagtggtcccaaagatggacccccac
ccacgaggaacatcgtggaaaaagaagacgttccaaccacgtcttcaaagcaagtggattgatgtgatgg
tcaacatggtggagcacgacactctcgtctactccaagaatatcaaagatacagtctcagaagaccagag
ggctattgagacttttcaacaaagggtaatatcgggaaacctcctcggattccattgcccagctatctgt
cacttcatcgaaaggacagtagaaaaggaagatggcttctacaaatgccatcattgcgataaaggaaagg
ctatcgttcaagatgcctctaccgacagtggtcccaaagatggaccccacccacgaggaacatcgtgga
aaagaagacgttccaaccacgtcttcaaagcaagtggattgatgtgatatctccactgacgtaagggat
gacgcacaatcccactatccttcgcaagacccttcctctatataaggaagttcatttcatttggagagga
taaaacattgcacctatggtgttgccctggctggggtatgtcagtgatcgcagtagaatgtactaattga
caagttggagaatacggtagaacgtccttatccaacacagcctttatccctctccctgacgaggtttttg
tcagtgtaatatttcttttgaactatccagcttagtacgtacgggaaagtgactggtgtgcttatctt
tgaaatgttactttgggtttcggttctttaggttagtaagaaagcacttgtcttctcatacaaaggaaaa
cctgagacgtatcgcttacgaaagtagcaatgaaagaaaggtggtggttttaatcgctaccgcaaaaacg
atggggtcgttttaattaacttctcctacgcaagcgtctaaacggacgttggggttttgctagtttcttt
agagaaaactagctaagtctttaatgttatcattagagatggcataaatataatacttgtgtctgctgat
aagatcattttaatttggacgattagacttgttgaactacaggttactgaatcacttgcgctaatcaaca
tgggagatatgtacgatgaatcatttgacaagtcgggcggtcctgctgacttgatggacgattcttggt
ggaatcagtttcgtggaaagatctgttgaagaagttacacagcataaaatttgcactacagtctggtaga
gatgagatcactgggttactagcggcactgaatagacagtgtccttattcaccatatgagcagtttccag
ataagaaggtgtatttccttttagactcacgggctaacagtgctcttggtgtgattcagaacgcttcagc
gttcaagagacgagctgatgagaagaatgcagtggcgggtgttacaaatattcctgcgaatccaaacaca
acggttacgacgaaccaagggagtactactactaccaaggcgaacactggctcgactttggaagaagact
tgtacacttattacaaattcgatgatgcctctacagctttccacaaatctctaacttcgttagagaacat
ggagttgaagagttattaccgaaggaactttgagaaagtattcgggattaagtttggtggagcagctgct
agttcatctgcaccgcctccagcgagtggaggtccgatacgtcctaatccctagggatttaaggacgtga
actctgttgagatctctgtgaaattcagagggtgggtgataccatattcactgatgccattagcgacatc
taaataggctaattgtgactaatttgagggaatttccttaccattgacgtcagtgtcgttggtagcat
ttgagtttcgcaatgcacgaattacttaggaagtggcttgacgacactaatgtgttattgttagataatg
gtttggtggtcaaggtacgtagtagagtcccacatattcgcacgtatgaagtaattggaaagttgtcagt
ttttgataattcactgggagatgatacgctgtttgagggaaaagtagagaacgtatttgttttatgttc
aggcggttcttgtgtgtcaacaaagatggacattgttactcaaggaagcacgatgagctttattattacg
gacgagtggacttagattctgtgagtaaggttaccgaattctctagaaggcctccatggggatccggtac
cgagctcacgcgtctcgaggccgggcatgtcccgaagacattaaactacggttctttaagtagatccgt
gtctgaagttttaggttcaatttaaacctacgagattgacattctcgactgatcttgattgatcggtaag
tcttttgtaatttaattttcttttgatttatttttaaattgttatctgtttctgtgtatagactgtttg
agatcggcgtttggccgactcattgtcttaccataggggaacggactttgtttgtgttgttatttatttt
gtattttattaaaattctcaacgatctgaaaaagcctcgcggctaagagattgttggggggtgagtaagt
actttaaagtgatgatggttacaaaggcaaaaggggtaaaaccctcgcctacgtaagcgttattacgc
ccgtctgtacttatatcagtacactgacgagtccctaaaggacgaaacgggagaacgctagccaccacca
ccaccaccgtgtgaattacaggtgaccagctcgaattccccgatcgttcaaacatttggcaataaag
tttcttaagattgaatcctgttgccggtcttgcgatgattatcatataatttctgttgaattacgttaag

*Fig. 19*

```
tgtgcatgccaaccacagggttcccctcgggatcaaagtactttgatccaaccccctccgctgctatagtg
cagtcggcttctgacgttcagtgcagccgtcttctgaaaacgacatgtcgcacaagtcctaagttacgcg
acaggctgccgccctgcccttttcctggcgttttcttgtcgcgtgttttagtcgcataaagtagaatact
tgcgactagaaccggagacattacgccatgaacaagagcgccgcgctggcctgctggctatgcccgcg
tcagcaccgacgaccaggacttgaccaaccaacgggccgaactgcacgcggccggctgcaccaagctgtt
ttccgagaagatcaccggcaccaggcgcgaccgcccggagctggccaggatgcttgaccacctacgccct
ggcgacgttgtgacagtgaccaggctagaccgctggccgcagcacccgcgacctactggacattgccg
agcgcatccaggaggccggcgcgggcctgcgtagcctggcagagccgtgggccgacaccaccacgccggc
cggccgcatggtgttgaccgtgttcgccggcattgccgagttcgagcgttccctaatcatcgaccgcacc
cggagcgggcgcgaggccgccaaggcccgaggcgtgaagtttggccccgccctacccctcaccccggcac
agatcgcgcacgccgcgagctgatcgaccaggaaggccgcaccgtgaaagaggcggctgcactgcttgg
cgtgcatcgctcgacctgtaccgcgcacttgagcgcagcgaggaagtgacgcccaccgaggccaggcgg
cgcggtgccttccgtgaggacgcattgaccgaggccgacgccctggcggccgcgagaatgaacgccaag
aggaacaagcatgaaaccgcaccaggacggccaggacgaaccgttttcattaccgaagagatcgaggcg
gagatgatcgcggccgggtacgtgttcgagccgccgcgcacgtctcaaccgtgcggctgcatgaaatcc
tggccggtttgtctgatgccaagctggcggcctggccggccagcttggccgctgaagaaaccgagcgccg
ccgtctaaaaaggtgatgtgtatttgagtaaaacagcttgcgtcatgcggtcgctgcgtatatgatgcga
tgagtaaataaacaaatacgcaaggggaacgcatgaaggttatcgctgtacttaaccagaaaggcgggtc
aggcaagacgaccatcgcaacccatctagcccgcgccctgcaactcgccggggccgatgttctgttagtc
gattccgatccccagggcagtgcccgcgattgggcggccgtgcgggaagatcaaccgctaaccgttgtcg
gcatcgaccgcccgacgattgaccgcgacgtgaaggccatcggccggcgcgacttcgtagtgatcgacgg
agcgccccaggcggcggacttggctgtgtccgcgatcaaggcagccgacttcgtgctgattccggtgcag
ccaagcccttacgacatatgggccaccgcgacctggtggagctggttaagcagcgcattgaggtcacgg
atggaaggctacaagcggcctttgtcgtgtcgcgggcgatcaaaggcacgcgcatcggcggtgaggttgc
cgaggcgctggccgggtacgagctgcccattcttgagtcccgtatcacgcagcgcgtgagctacccaggc
actgccgccgccggcacaaccgttcttgaatcagaacccgagggcgacgctgccgcgaggtccaggcgc
tggccgctgaaattaaatcaaaactcatttgagttaatgaggtaaagagaaaatgagcaaaagcacaaac
acgctaagtgccggccgtccgagcgcacgcagcagcaaggctgcaacgttggccagcctggcagacacgc
cagccatgaagcgggtcaactttcagttgccggcggaggatcacaccaagctgaagatgtacgcggtacg
ccaaggcaagaccattaccgagctgctatctgaatacatcgcgcagctaccagagtaaatgagcaaatga
ataaatgagtagatgaattttagcggctaaaggaggcggcatggaaaatcaagaacaaccaggcaccgac
gccgtggaatgcccccatgtgtggaggaacgggcggttggccaggcgtaagcggctggttgtctgccggc
cctgcaatggcactggaaccccaagcccgaggaatcggcgtgacggtcgcaaaccatccggcccggtac
aaatcggcgcggcgctgggtgatgacctggtggagaagttgaaggccgcgcaggccgcccagcggcaacg
catcgaggcagaagcacgccccggtgaatcgtggcaagcggccgctgatcgaatccgcaaagaatcccgg
caaccgccggcagccggtgcgccgtcgattaggaagccgcccaagggcgacgagcaaccagatttttcg
ttccgatgctctatgacgtgggcacccgcgatagtcgcagcatcatggacgtggccgttttccgtctgtc
gaagcgtgaccgacgagctggcgaggtgatccgctacgagcttccagacgggcacgtagaggtttccgca
ggccggccggcatggccagtgtgtggattacgacctggtactgatggcggtttcccatctaaccgaat
ccatgaaccgataccgggaagggaagggagacaagcccggccgcgtgttccgtccacacgttgcggacgt
actcaagttctgccggcgagccgatggcggaaagcagaaagacgacctggtagaaacctgcattcggtta
aacaccacgcacgttgccatgcagcgtacgaagaaggccaagaacggccgcctggtgacggtatccgagg
gtgaagccttgattagccgctacaagatcgtaaagagcgaaaccggggcgccggagtacatcgagatcga
gctagctgattggatgtaccgcgagatcacagaaggcaagaacccggacgtgctgacggttcacccccgat
tacttttttgatcgatcccggcatcggccgttttctctaccgcctggcacgccgcgccgcaggcaaggcag
```

```
gtacattgggaacccaaagccgtacattgggaaccggaacccgtacattgggaacccaaagccgtacatt
gggaaccggtcacacatgtaagtgactgatataaaagagaaaaaggcgattttccgcctaaaactctt
taaaacttattaaaactcttaaaacccgcctggcctgtgcataactgtctggccagcgcacagccgaaga
gctgcaaaagcgcctacccttcggtcgctgcgctccctacgcccgccgcttcgcgtcggcctatcgcg
gccgctggccgctcaaaaatggctggcctacggccaggcaatctaccagggcgcggacaagccgcgccgt
cgccactcgaccgccggcgcccacatcaaggcaccctgcctcgcgcgtttcggtgatgacggtgaaaacc
tctgacacatgcagctcccggagacggtcacagcttgtctgtaagcggatgcgggagcagacaagcccg
tcagggcgcgtcagcgggtgttggcgggtgtcggggcgcagccatgacccagtcacgtagcgatagcgga
gtgtatactggcttaactatgcggcatcagagcagattgtactgagagtgcaccatatgcggtgtgaaat
accgcacagatgcgtaaggagaaaataccgcatcaggcgctcttccgcttcctcgctcactgactcgctg
cgctcggtcgttcggctgcggcgagcggtatcagctcactcaaaggcggtaatacggttatccacagaat
caggggataacgcaggaaagaacatgtgagcaaaaggccagcaaaaggccaggaaccgtaaaaaggccgc
gttgctggcgtttttccataggctccgcccccctgacgagcatcacaaaaatcgacgctcaagtcagagg
tggcgaaacccgacaggactataaagataccaggcgtttccccctggaagctccctcgtgcgctcctg
ttccgaccctgccgcttaccggatacctgtccgcctttctcccttcgggaagcgtggcgctttctcatag
ctcacgctgtaggtatctcagttcggtgtaggtcgttcgctccaagctgggctgtgtgcacgaaccccc
gttcagcccgaccgctgcgccttatccggtaactatcgtcttgagtccaacccggtaagacacgacttat
cgccactggcagcagccactggtaacaggattagcagagcgaggtatgtaggcggtgctacagagttctt
gaagtggtggcctaactacggctacactagaaggacagtatttggtatctgcgctctgctgaagccagtt
accttcggaaaagagttggtagctcttgatccggcaaacaaaccaccgctggtagcggtggtttttttg
tttgcaagcagcagattacgcgcagaaaaaaaggatctcaagaagatcctttgatcttttctacggggtc
tgacgctcagtggaacgaaaactcacgttaagggattttggtcatgcattctaggtactaaaacaattca
tccagtaaaatataatattttattttctcccaatcaggcttgatccccagtaagtcaaaaaatagctcga
catactgttcttccccgatatcctccctgatcgaccggacgcagaaggcaatgtcataccacttgtccgc
cctgccgcttctcccaagatcaataaagccacttactttgccatctttcacaaagatgttgctgtctccc
aggtcgccgtgggaaaagacaagttcctcttcgggcttttccgtctttaaaaaatcatacagctcgcgcg
gatctttaaatggagtgtcttcttcccagttttcgcaatccacatcggcagatcgttattcagtaagta
atccaattcggctaagcggctgtctaagctattcgtatagggacaatccgatatgtcgatggagtgaaag
agcctgatgcactccgcatacagctcgataatcttttcagggctttgttcatcttcatactcttccgagc
aaaggacgccatcggcctcactcatgagcagattgctccagccatcatgccgttcaaagtgcaggacctt
tggaacaggcagctttccttccagccatagcatcatgtccttttccgttccacatcataggtggtccct
ttataccggctgtccgtcatttttaaatataggttttcattttctcccaccagcttatataccttagcag
gagacattccttccgtatcttttacgcagcggtattttcgatcagttttttcaattccggtgatattct
cattttagccatttattatttccttcctcttttctacagtatttaaagatacccaagaagctaattata
acaagacgaactccaattcactgttccttgcattctaaaaccttaaataccagaaacagcttttcaaa
gttgttttcaaagttggcgtataacatagtatcgacggagccgattttgaaaccgcggtgatcacaggca
gcaacgctctgtcatcgttacaatcaacatgctaccctcgcgagatcatccgtgtttcaaacccggcag
cttagttgccgttcttccgaatagcatcggtaacatgagcaaagtctgccgccttacaacggctctccg
ctgacgccgtcccggactgatgggctgcctgtatcgagtggtgattttgtgccgagctgccggtcgggga
gctgttggctggctggtggcaggatatattgtggtgtaaacaaattgacgcttagacaacttaataacac
attgcggacgttttaatgtactgaattaacgccgaattaattcctaggccaccatgttgggccggcgc
gcc
```

*Fig. 19-Cont'd*

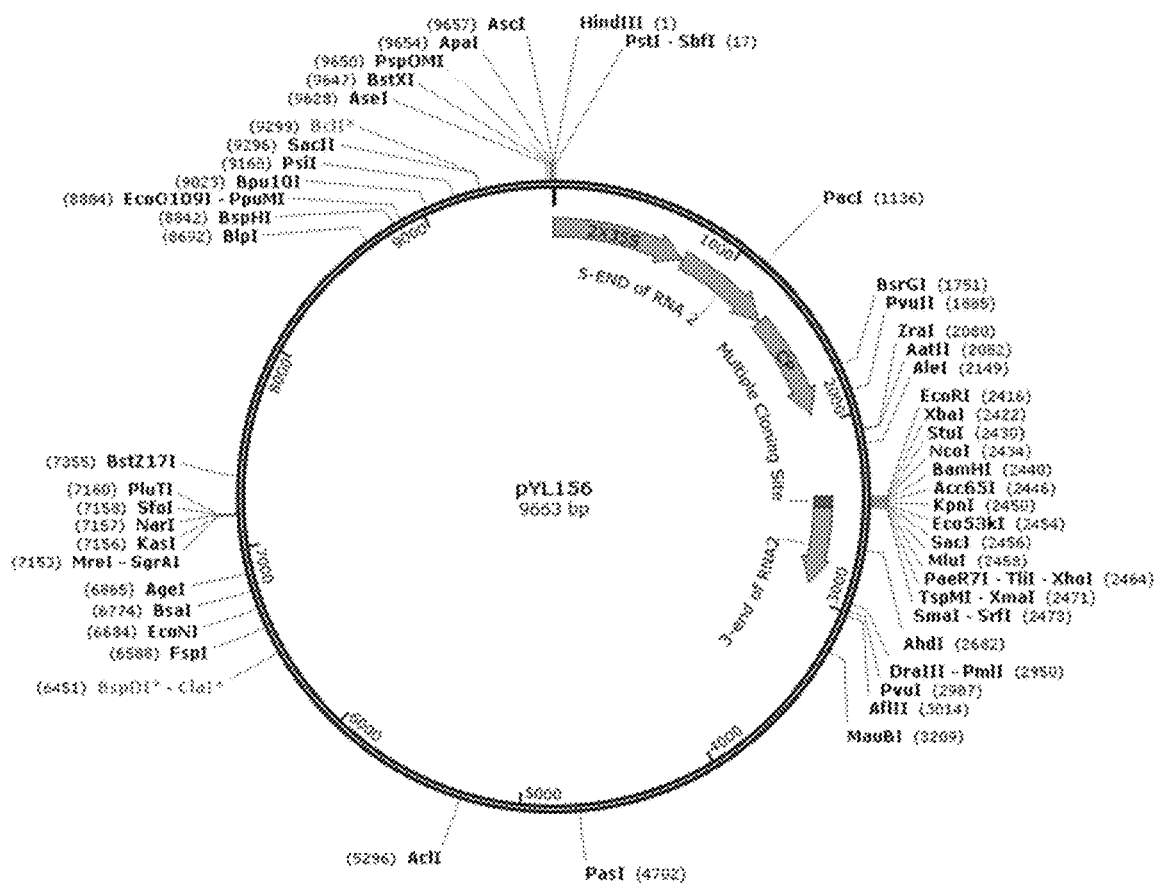

Fig. 20

Arabidopsis U6 promoter sequence for expression of sgRNA
(SEQ ID NO: 7)
agaaatctcaaaattccggcagaacaattttgaatctcgatccgtagaaacgagacggtcattgttttag
ttccaccacgattatatttgaaatttacgtgagtgtgagtgagacttgcataagaaaataaaatctttag
ttgggaaaaaattcaataatataaatgggcttgagaaggaagcgagggataggccttttttctaaaatagg
cccatttaagctattaacaatcttcaaaagtaccacagcgcttaggtaaagaaagcagctgagtttatat
atggttagagacgaagtagtgatt

Fig. 21

SPDK-RNA2 complete sequence and map (SEQ ID NO: 8)
AAGCTTGCATGCCTGCAGGTCAACATGGTGGAGCACGACACTCTCGTCTACTCCAAGAATATCAAAGATA
CAGTCTCAGAAGACCAGAGGGCTATTGAGACTTTTCAACAAAGGGTAATATCGGGAAACCTCCTCGGATT
CCATTGCCCAGCTATCTGTCACTTCATCGAAAGGACAGTAGAAAAGGAAGATGGCTTCTACAAATGCCAT
CATTGCGATAAAGGAAAGGCTATCGTTCAAGATGCCTCTACCGACAGTGGTCCCAAAGATGGACCCCCAC
CCACGAGGAACATCGTGGAAAAAGAAGACGTTCCAACCACGTCTTCAAAGCAAGTGGATTGATGTGATGG
TCAACATGGTGGAGCACGACACTCTCGTCTACTCCAAGAATATCAAAGATACAGTCTCAGAAGACCAGAG
GGCTATTGAGACTTTTCAACAAAGGGTAATATCGGGAAACCTCCTCGGATTCCATTGCCCAGCTATCTGT
CACTTCATCGAAAGGACAGTAGAAAAGGAAGATGGCTTCTACAAATGCCATCATTGCGATAAAGGAAAGG
CTATCGTTCAAGATGCCTCTACCGACAGTGGTCCCAAAGATGGACCCCCACCCACGAGGAACATCGTGGA
AAAGAAGACGTTCCAACCACGTCTTCAAAGCAAGTGGATTGATGTGATATCTCCACTGACGTAAGGGAT
GACGCACAATCCCACTATCCTTCGCAAGACCCTTCCTCTATATAAGGAAGTTCATTTCATTTGGAGagga
taaaacattgcacctatggtgttgccctggctggggtatgtcagtgatcgcagtagaatgtactaattga
caagttggagaatacggtagaacgtccttatccaacacagcctttatccctctccctgacgaggttttg
tcagtgtaatatttcttttgaactatccagcttagtaccgtacgggaaagtgactggtgtgcttatctt
tgaaatgttactttgggtttcggttctttaggttagtaagaaagcacttgtcttctcatacaaaggaaaa
cctgaGAcgtatcgcttacgaaagtagcaatgaaagaaaggtggtggttttaatcgCtaccgcaaaaacg
atggggtcgttttaattaacttctcctacGCaagcgtctaaacggacgttggggttttgctagtttcttt
agagaaaactagctaagtctttaatgttatcattagagatggcataaatataatacttgtgtctgctgat
aagatcattttaatttggacgattagacttgttgaactacaggttactgaatcacttgcgctaatcaacA
TGggagatatgtacgatgaatcatttgacaagtcgggcggtcctgctgacttgatggacgattcttgggt
ggaatcagtttcgtggaaagatCtgttgaagaagttacacagcataaaatttgcactacagtctggtaga
gatgagatcactgggttactagcggcactgaatagacagtgtccttattcaccatatgagcagtttccag
ataagaaggtgtatttcctttagactcacgggctaacagtgctcttggtgtgattcagaacgcttcagc
gttcaagagacgagctgatgagaagaatgcagtggcgggtgttacaaatattcctgcgaatccaaacaca
acggttacgacgaaccaagggagtactactactaccaaggcgaacactggctcgactttggaagaagact
tgtacacttattacaaattcgatgatgcctctacagcttttccacaaatctctaacttcgttagagaacat
ggagttgaagagttattaccgaaggaactttgagaaagtattcgggattaagtttggtggagcagctgct
agttcatctgcaccgcctccagcgagtggaggtccgatacgtcctaatccctagggatttaaggacgtga
actctgttgagatctctgtgaaattcagagggtgggtgataccatattcactgatgccattagcgacatc
taaataggctaattgtgactaatttgagggaatttcctttaccattgacgtcagtgtcgttggtagcat
ttgagtttcgAATTCGAGCATCTTGTTCTGGGGTTTCACACTATCTTTAGAGAAAGTGTTAAGTTAATTA
AGTTATCTTAATTAAGAGCATAATTATACTGATTTGTCTCTCGTTGATAGAGTCTATCATTCTGTTACTA
AAAATTTGACAACTCGGTTTGCTGACCTACTGGTTACTGTATCACTTACCCGAGTTAACGAGtctagaAG
GCCTCCATGGGGATCCGGTACCGAGCTCACGCGTCTCGAGGCCCGGGCatgtcccgaagacattaaacta
cgGttctttaagtagatccgtgTctgaagtttaggttcaatttaaacctacgagattgacattctcgac
tgatcttgattgatcggtaagtcttttgtaatttaattttcttttgattttatttaaattgttatctg
tttctgtgtatagactgtttgagatcggcgtttGgCCgActcattgtcttaccataggggaacggacttt
gtttgtgttgttatttttatttgtattttattaaaattctcaacgatctgaaaaagcctcgcgGctaagag
attgttggggggtgagtaagtacttttaaagtgatgatggttacaaaggcaaagggggtaaaacccctcg
cctacgtaagcgttattacgcccGTCTGTACTTATATCAGTACACTGACGAGTCCCTAAAGGACGAAACG
GGAGaacgctagccaccaccaccaccaccacgtgtgaattacaggtgaccagctcgaatttccccgatcg
ttcaaacatttggcaataaagtttcttaagattgaatcctgttgccggtcttgcgatgattatcatataa
tttctgttgaattacgttaagcatgtaataattaacatgtaatgcatgacgttatttatgagatgggttt
ttatgattagagtcccgcaattatacatttaatacgcgatagaaaacaaaatatagcgcgcaaactagga

*Fig. 22*

```
gcacaagtcctaagttacgcgacaggctgccgccctgccctttcctggcgttttcttgtcgcgtgtttt
agtcgcataaagtagaatacttgcgactagaaccggagacattacgccatgaacaagagcgccgccgctg
gcctgctgggctatgccgcgtcagcaccgacgaccaggacttgaccaaccaacgggccgaactgcacgc
ggccggctgcaccaagctgttttccgagaagatcaccggcaccaggcgcgaccgcccggagctggccagg
atgcttgaccacctacgccctggcgacgttgtgacagtgaccaggctagaccgcctggcccgcagcaccc
gcgacctactggacattgccgagcgcatccaggaggccggcgcgggcctgcgtagcctggcagagccgtg
ggccgacaccaccacgccggccggccgcatggtgttgaccgtgttcgccggcattgccgagttcgagcgt
tccctaatcatcgaccgcacccggagcgggcgcgaggccgccaaggcccgaggcgtgaagtttggccccc
gccctacccctcaccccggcacagatcgcgcacgcccgcgagctgatcgaccaggaaggccgcaccgtgaa
agaggcggctgcactgcttggcgtgcatcgctcgaccctgtaccgcgcacttgagcgcagcgaggaagtg
acgccaccgaggccaggcggcgcggtgccttccgtgaggacgcattgaccgaggccgacgccctggcgg
ccgccgagaatgaacgccaagaggaacaagcatgaaaccgcaccaggacggccaggacgaaccgtttttc
attaccgaagagatcgaggcggagatgatcgcggccgggtacgtgttcgagccgcccgcgcacgtctcaa
ccgtgcggctgcatgaaatcctggccggtttgtctgatgccaagctggcggcctggccggccagcttggc
cgctgaagaaaccgagcgccgccgtctaaaaaggtgatgtgtatttgagtaaaacagcttgcgtcatgcg
gtcgctgcgtatatgatgcgatgagtaaataaacaaatacgcaaggggaacgcatgaaggttatcgctgt
acttaaccagaaaggcgggtcaggcaagacgaccatcgcaacccatctagcccgcgccctgcaactcgcc
ggggccgatgttctgttagtcgattccgatccccagggcagtgcccgcgattgggcggccgtgcgggaag
atcaaccgctaaccgttgtcggcatcgaccgcccgacgattgaccgcgacgtgaaggccatcggccggcg
cgacttcgtagtgatcgacggagcgccccaggcggcggacttggctgtgtccgcgatcaaggcagccgac
ttcgtgctgattccggtgcagccaagcccttacgacatatgggccaccgccgacctggtggagctggtta
agcagcgcattgaggtcacggatggaaggctacaagcggcctttgtcgtgtcgcgggcgatcaaaggcac
gcgcatcggcggtgaggttgccgaggcgctggccgggtacgagctgcccattcttgagtcccgtatcacg
cagcgcgtgagctacccaggcactgccgccgccggcacaaccgttcttgaatcagaacccgagggcgacg
ctgccgcgaggtccaggcgctggccgctgaaattaaatcaaaactcatttgagttaatgaggtaaagag
aaaatgagcaaaagcacaaacacgctaagtgccggccgtccgagcgcacgcagcagcaaggctgcaacgt
tggccagcctggcagacacgccagccatgaagcgggtcaactttcagttgccggcggaggatcacaccaa
gctgaagatgtacgcggtacgccaaggcaagaccattaccgagctgctatctgaatacatcgcgcagcta
ccagagtaaatgagcaaatgaataaatgagtagatgaattttagcggctaaaggaggcggcatggaaaat
caagaacaaccaggcaccgacgccgtggaatgccccatgtgtggaggaacgggcggttggccaggcgtaa
gcggctgggttgtctgccggccctgcaatggcactggaaccccaagcccgaggaatcggcgtgacggtc
gcaaaccatccggcccggtacaaatcggcgcggcgctgggtgatgacctggtggagaagttgaaggccgc
gcaggccgcccagcggcaacgcatcgaggcagaagcacgccccggtgaatcgtggcaagcggccgctgat
cgaatccgcaaagaatcccggcaaccgccggcagccggtgcgccgtcgattaggaagccgcccaagggcg
acgagcaaccagatttttcgttccgatgctctatgacgtgggcacccgcgatagtcgcagcatcatgga
cgtggccgttttccgtctgtcgaagcgtgaccgacgagctggcgaggtgatccgctacgagcttccagac
gggcacgtagaggtttccgcagggccggccggcatggccagtgtgtgggattacgacctggtactgatgg
cggtttcccatctaaccgaatccatgaaccgataccgggaagggaagggagacaagcccggccgcgtgtt
ccgtccacacgttgcggacgtactcaagttctgccggcgagccgatggcggaaagcagaaagacgacctg
gtagaaacctgcattcggttaaacaccacgcacgttgccatgcagcgtacgaagaaggccaagaacggcc
gcctggtgacggtatccgagggtgaagccttgattagccgctacaagatcgtaaagagcgaaaccgggcg
gccggagtacatcgagatcgagctagctgattggatgtaccgcgagatcacagaaggcaagaacccggac
gtgctgacggttcaccccgattacttttgatcgatcccggcatcggccgttttctctaccgcctggcac
gccgcgccgcaggcaaggcagaagccagatggttgttcaagacgatctacgaacgcagtggcagcgccgg
agagttcaagaagttctgtttcaccgtgcgcaagctgatcgggtcaaatgacctgccggagtacgatttg
```

*Fig. 22-Cont'd*

```
gggaacccaaagccgtacattgggaaccggtcacacatgtaagtgactgatataaaagagaaaaaggcg
attttccgcctaaaactctttaaaacttattaaaactcttaaaacccgcctggcctgtgcataactgtc
tggccagcgcacagccgaagagctgcaaaaagcgcctacccttcggtcgctgcgctccctacgccccgcc
gcttcgcgtcggcctatcgcggccgctggccgctcaaaaatggctggcctacggccaggcaatctaccag
ggcgcggacaagccgcgccgtcgccactcgaccgccggcgcccacatcaaggcaccctgcctcgcgcgtt
tcggtgatgacggtgaaaacctctgacacatgcagctccggagacggtcacagcttgtctgtaagcgga
tgccgggagcagacaagcccgtcagggcgcgtcagcgggtgttggcgggtgtcggggcgcagccatgacc
cagtcacgtagcgatagcggagtgtatactggcttaactatgcggcatcagagcagattgtactgagagt
gcaccatatgcggtgtgaaataccgcacagatgcgtaaggagaaaataccgcatcaggcgctcttccgct
tcctcgctcactgactcgctgcgctcggtcgttcggctgcggcgagcggtatcagctcactcaaaggcgg
taatacggttatccacagaatcaggggataacgcaggaaagaacatgtgagcaaaaggccagcaaaaggc
caggaaccgtaaaaaggccgcgttgctggcgtttttccataggctccgcccccctgacgagcatcacaaa
aatcgacgctcaagtcagaggtggcgaaacccgacaggactataaagataccaggcgtttccccctggaa
gctccctcgtgcgctctcctgttccgaccctgccgcttaccggatacctgtccgcctttctcccttcggg
aagcgtggcgctttctcatagctcacgctgtaggtatctcagttcggtgtaggtcgttcgctccaagctg
ggctgtgtgcacgaaccccccgttcagcccgaccgctgcgccttatccggtaactatcgtcttgagtcca
acccggtaagacacgacttatcgccactggcagcagccactggtaacaggattagcagagcgaggtatgt
aggcggtgctacagagttcttgaagtggtggcctaactacggctacactagaaggacagtatttggtatc
tgcgctctgctgaagccagttaccttcggaaaaagagttggtagctcttgatccggcaaacaaaccaccg
ctggtagcggtggtttttttgtttgcaagcagcagattacgcgcagaaaaaaaggatctcaagaagatcc
tttgatcttttctacggggtctgacgctcagtggaacgaaaactcacgttaagggattttggtcatgcat
tctaggtactaaaacaattcatccagtaaaatataatattttattttctcccaatcaggcttgatcccca
gtaagtcaaaaaatagctcgacatactgttcttccccgatatcctccctgatcgaccggacgcagaaggc
aatgtcataccacttgtccgccctgccgcttctcccaagatcaataaagccacttactttgccatctttc
acaaagatgttgctgtctcccaggtcgccgtgggaaaagacaagttcctcttcgggcttttccgtcttta
aaaaatcatacagctcgcgcggatctttaaatggagtgtcttcttcccagttttcgcaatccacatcggc
cagatcgttattcagtaagtaatccaattcggctaagcggctgtctaagctattcgtatagggacaatcc
gatatgtcgatggagtgaaagagcctgatgcactccgcatacagctcgataatcttttcagggctttgtt
catcttcatactcttccgagcaaaggacgccatcggcctcactcatgagcagattgctccagccatcatg
ccgttcaaagtgcaggacctttggaacaggcagcttccttccagccatagcatcatgtccttttcccgt
tccacatcataggtggtccctttataccggctgtccgtcattttaaatataggtttcattttctccca
ccagcttatataccttagcaggagacattccttccgtatctttacgcagcggtattttcgatcagttt
tttcaattccggtgatattctcattttagccatttattatttccttcctcttttctacagtatttaaaga
taccccaagaagctaattataacaagacgaactccaattcactgttccttgcattctaaaaccttaaata
ccagaaaacagctttttcaaagttgttttcaaagttggcgtataacatagtatcgacggagccgattttg
aaacgcggtgatcacaggcagcaacgctctgtcatcgttacaatcaacatgctaccctccgcgagatca
tccgtgtttcaaacccggcagcttagttgccgttcttccgaatagcatcggtaacatgagcaaagtctgc
cgccttacaacggctctcccgctgacgccgtcccggactgatggctgcctgtcgagtggtgattttg
tgccgagctgccggtcggggagctgttggctggctggtggcaggatatattgtggtgtaaacaaattgac
gcttagacaacttaataacacattgcggacgtttttaatgtactgaattaacgccgaattaattcctagg
ccaccatgttgggcccggcgcgcc
```

*Fig. 22-Cont'd*

YL192 complete sequence and map (SEQ ID NO: 9)
ataaaacatttcaatcctttgaacgcggtagaacgtgctaattggattttggtgagaacgcggtagaacg
tacttatcacctacagttttattttgttttcttttggtttaatctatccagcttagtaccgagtgggg
gaaagtgactggtgtgcctaaaaccttttctttgatactttgtaaaaatacatacagatacaatggcgaa
cggtaacttcaagttgtctcaattgctcaatgtggacgagatgtctgctgagcagaggagtcatttcttt
gacttgatgctgactaaacctgattgtgagatcgggcaaatgatgcaagagttgttgttgataaagtcg
atgacatgattagagaaagaaagactaaagatccagtgattgttcatgaagttctttctcagaaggaaca
gaacaagttgatggaaatttatcctgaattcaatatcgtgtttaaagacgacaaaaacatggttcatggg
tttgcggctgctgagcgaaaactacaagctttattgcttttagatagagttcctgctctgcaagaggtgg
atgacatcggtggtcaatggtcgttttgggtaactagaggtgagaaaaggattcattcctgttgtccaaa
tctagatattcgggatgatcagagagaaatttctcgacagatatttcttactgctattggtgatcaagct
agaagtggtaagagacagatgtcggagaatgagctgtggatgtatgaccaatttcgtgaaaatattgctg
cgcctaacgcggttaggtgcaataatacatatcaggttgtacatgtagggttttctgatggtaagaa
gaaaggcgcgcagtatgcgatagctcttcacagcctgtatgacttcaagttgaaagacttgatggctact
atggttgagaagaaaactaaagtggttcatgctgctatgcttttgctcctgaaagtatgttagtggacg
aaggtccattaccttctgttgacggttactacatgaagaagaacgggaagatctatttcggttttgagaa
agatccttccttttcttacattcatgactgggaagagtacaagaagtatctactggggaagccagtgagt
taccaagggaatgtgttctacttcgaaccgtggcaggtgagaggagacacaatgcttttttcgatctaca
ggatagctggagttccgaggaggtctctatcatcgcaagagtactaccgaagaatatatatcagtagatg
gaaaacatggttgttgtcccaattttcgatctggtcgaatcaacgcgagagttggtcaagaaagacctg
tttgtagagaaacaattcatggacaagtgtttggattacatagctaggttatctgaccagcagctgacca
taagcaatgttaaatcatacttgagttcaaataattgggtcttattcataaacggggcggccgtgaagaa
caagcaaagtgtagattctcgagatttacagttgttggctcaaactttgctagtgaaggaacaagtggcg
agacctgtcatgagggagttgcgtgaagcaattctgactgagacgaaacctatcacgtcattgactgatg
tgctgggtttaatatcaagaaaactgtggaagcagtttgctaacaagatcgcagtcggcggattcgttgg
catggttggtactctaattggattctatccaaagaaggtactaacctgggcgaaggacacaccaaatggt
ccagaactatgttacgagaactcgcacaaaaccaaggtgatagtatttctgagtgttgtgtatgccattg
gaggaatcacgcttatgcgtcgagacatccgagatggactggtgaaaaaactatgtgatatgtttgatat
caaacgggggcccatgtcttagacgttgagaatccgtgccgctattatgaaatcaacgatttctttagc
agtctgtattcggcatctgagtccggtgagaccgttttaccagatttatccgaggtaaaagccaagtctg
ataagctattgcagcagaagaaagaaatcgctgacgagtttctaagtgcaaaattctctaactattctgg
cagttcggtgagaacttctccaccatcggtggtcggttcatctcgaagcggactgggtctgttgttggaa
gacagtaacgtgctgacccaagctagagttggagtttcaagaaaggtagacgatgaggagatcatggagc
agtttctgagtggtcttattgacactgaagcagaaattgacgaggttgttccagccttttcagctgaatg
tgaaagaggggaaacaagcggtacaaaggtgttgtgtaaacctttaacgccaccaggatttgagaacgtg
ttgccagctgtcaaacctttggtcagcaaaggaaaaacggtcaaacgtgtcgattacttccaagtgatgg
gaggtgagagattaccaaaaaggccggttgtcagtggagacgattctgtggacgctagaagagagtttct
gtactacttagatgcggagagagtcgctcaaaatgatgaaattatgtctctgtatcgtgactattcgaga
ggagttattcgaactggaggtcagaattacccgcacggactgggagtgtgggatgtggagatgaagaact
ggtgcatacgtccagtggtcactgaacatgcttatgtgttccaaccagacaaacgtatggatgattggtc
gggatacttagaagtggctgtttgggaacgaggtatgttggtcaacgacttcgcggtcgaaaggatgagt
gattatgtcatagtttgcgatcagacgtatctttgcaataacaggttgatcttggacaatttaagtgccc
tggatctaggaccagttaactgttcttttgaattagttgacggtgtacctggttgtggtaagtcgacaat
gattgtcaactcagctaatccttgtgtcgatgtggttctctctactgggagagcagcaaccgacgacttg
atcgagagattcgcgagcaaaggttttccatgcaaattgaaaaggagagtgaagacggttgattcttttt
tgatgcattgtgttgatggttctttaaccggagacgtgttgcatttcgatgaagctctcatggcccatgc
tggtatggtgtacttttgcgctcagatagctggtgctaaacgatgtatctgtcaaggagatcagaatcaa
atttctttcaagcctagggtatctcaagttgatttgaggttttctagtctggtcggaaagtttgacattg
ttacagaaaaagagaaacttacagaagtccagcagatgtggctgccgtattgaacaagtactatactgg
agatgtcagaacacataacgcgactgctaattcgatgacggtgaggaagattgtgtctaaagaacaggtt

*Fig. 24*

```
tctttgaagcctggtgctcagtacataactttccttcagtctgagaagaaggagttggtaaatttgttgg
cattgaggaaagtggcagctaaagtgagtacagtacacgagtcgcaaggagagacattcaaagatgtagt
cctagtcaggacgaaacctacggatgactcaatcgctagaggtcgggagtacttaatcgtggcgttgtcg
cgtcacacacaatcacttgtgtatgaaactgtgaagaggacgatgtaagcaaagagatcagggaaagtg
ccgcgcttacgaaggcggctttggcaagattttttgttactgagaccgtcttatgacggtttcggtctag
gtttgatgtctttagacatcatgaagggccttgcgccgttccagattcaggtacgattacggacttggag
atgtggtacgacgctttgtttccgggaaattcgttaagagactcaagcctagacgggtatttggtggcaa
cgactgattgcaatttgcgattagacaatgttacgatcaaaagtggaaactggaaagacaagtttgctga
aaaagaaacgtttctgaaaccggttattcgtactgctatgcctgacaaaggaagactactcagttggag
agtttgttagcattgcagaaaaggaaccaagcggcacccgatctacaagaaaatgtgcacgcaacagttc
taatcgaagagacgatgaagaagttgaaatctgttgtctacgatgtgggaaaaattcgggctgatcctat
tgtcaatagagctcaaatggagagatggtggagaaatcaaagcacagcggtacaggctaaggtagtagca
gatgtgagagagttacatgaaatagactattcgtcttacatgtatatgatcaaatctgacgtgaaaccta
agactgatttaacaccgcaatttgaatactcagctctacagactgttgtgtatcacgagaagttgatcaa
ctcgttgttcggtccaatttttcaaagaaattaatgaacgcaagttggatgctatgcaaccacattttgtg
ttcaacacgagaatgacatcgagtgatttaaacgatcgagtgaagttcttaaatacggaagcggcttacg
actttgttgagatagacatgtctaaattcgacaagtcggcaaatcgcttccatttacaactgcagctgga
gatttacaggttatttgggctagatgagtgggcggccttcctttgggaggtgtcgcacactcaaactact
gtgagagatattcaaaatggtatgatggcgcatatttggtaccaacaaaagagtggagatgctgatactt
ataatgcaaattcagatagaacactgtgtgcactcttgtctgaattaccattggagaaagcagtcatggt
tacatatggaggagatgactcactgattgcgtttcctagaggaacgcagtttgttgatccgtgtccaaag
ttggctactaagtggaatttcgagtgcaagattttttaagtacgatgtcccaatgttttgtgggaagttct
tgcttaagacgtcatcgtgttacgagttcgtgccagatccggtaaaagttctgacgaagttggggaaaaa
gagtataaaggatgtgcaacatttagccgagatctacatctcgctgaatgattccaatagagctcttggg
aactacatggtggtatccaaactgtccgagtctgtttcagaccggtatttgtacaaggtgattctgttc
atgcgctttgtgcgctatggaagcatattaagagttttacagctctgtgtacattattccgagacgaaaa
cgataaggaattgaacccggctaaggttgattggaagaaggcacagagagctgtgtcaaacttttacgac
tggtaatatggaagacaagtcattggtcaccttgaagaagaagactttcgaagtctcaaaattctcaaat
ctaggggccattgaattgtttgtggacggtaggaggaagagaccgaagtattttcacagaagaagagaaa
ctgtcctaaatcatgttggtgggaagaagagtgaacacaagttagacgttttttgaccaaagggattacaa
aatgattaaatcttacgcgtttctaaagatagtaggtgtacaactagttgtaacatcacatctacctgca
gatacgcctgggttcattcaaatcgatctgttggattcgagacttactgagaaaagaaagagaggaaaga
ctattcagagattcaaagctcgagcttgcgataactgttcagttgcgcagtacaaggttgaatacagtat
ttccacacaggagaacgtacttgatgtctggaaggtgggttgtatttctgagggcgttccggtctgtgac
ggtacatacccttttcagtatcgaagtgtcgctaatatggggttgctactgattcgactaggcgcctcaatg
tggaagaactgaacagttcggattacattgaaggcgatttaccgatcaagaggttttcggtgagttcat
gtctttgaaacaagtggagatgaagacgattgaggcgaagtacgatggtccttacagaccagctactact
agacctaagtcattattgtcaagtgaagatgttaagagagcgtctaataagaaaaactcgtcttaatgca
taaagaaatttattgtcaatatgacgtgtgtactcaagggttgtgtgaatgaagtcactgttcttggtca
cgagacgtgtagtatcggtcatgctaacaaattgcgaaagcaagttgctgacatggttggtgtcacacgt
aggtgtgcggaaaataattgtggatggtttgtctgtgttgttatcaatgatttactttttgatgtgtata
attgttgtggccgtagtcaccttgaaaagtgtcgtaaacgtgttgaaacaagaaatcgagaaatttggaa
acaaattcgacgaaatcaagctgaaaacatgtctgcgacagctaaaaagtctcataattcgaagacctct
aagaagaaattcaaagaggacagagaatttgggacaccaaaagatttttaagagatgatgttcctttcg
ggattgatcgtttgtttgcttttgatttatttatattgttatctgtttctgtgtatagactgtttga
gattggcgcttggccgactcattgtcttaccataggggaacggactttgtttgtgttgttatttttatttg
tattttattaaaattctcaatgatctgaaaaggcctcgaggctaagagattattgggggtgagtaagta
cttttaaagtgatgatggttacaaaggcaaaaggggtaaaacccctcgcctacgtaagcgttattacgcc
c
```

*Fig. 24-Cont'd*

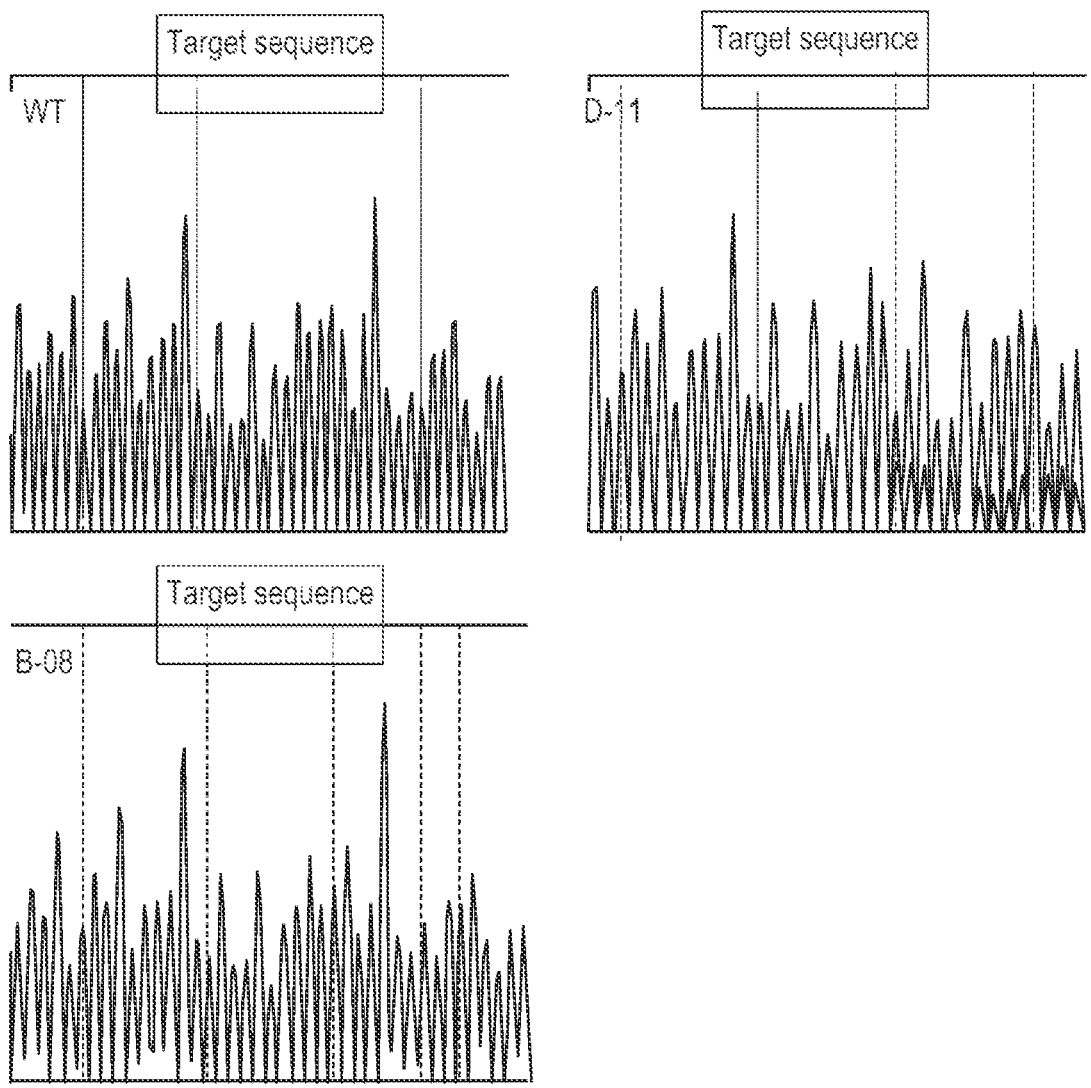
FIG. 28
FIG. 29

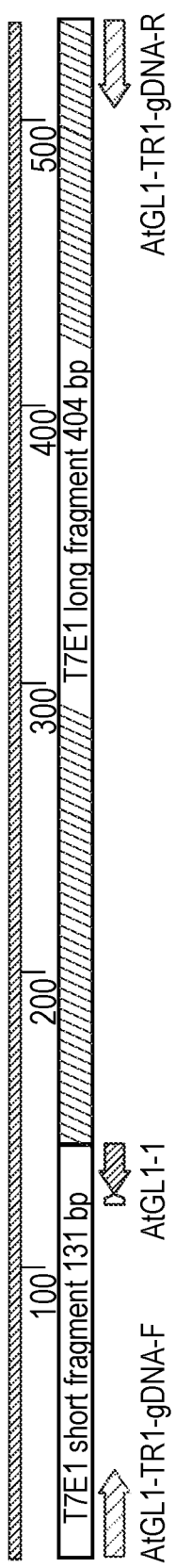
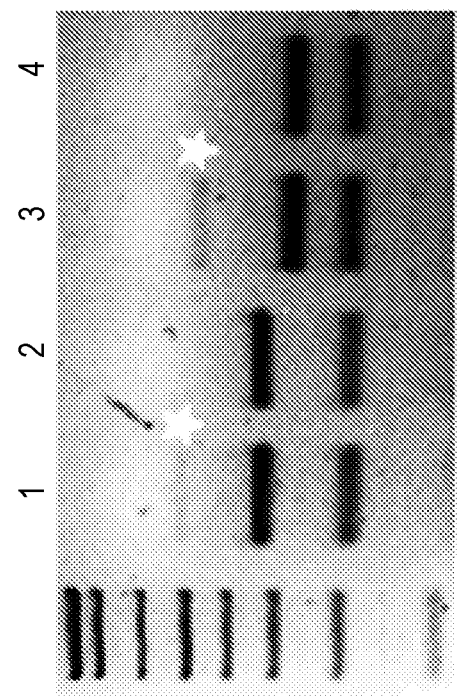
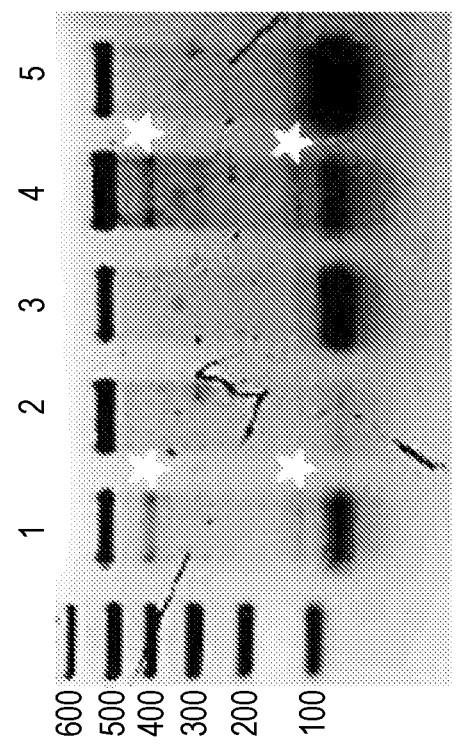
FIG. 32A
FIG. 32B
FIG. 32C

SEQUENCE LISTING

<160> NUMBER OF SEQ ID NOS: 147

<210> SEQ ID NO 1
<211> LENGTH: 4272
<212> TYPE: DNA
<213> ORGANISM: Artificial sequence
<220> FEATURE:
<223> OTHER INFORMATION: Cas9 sequence (flag-nls-cas9-nls)

<400> SEQUENCE: 1

```
atggactata aggaccacga cggagactac aaggatcatg atattgatta caaagacgat      60
gacgataaga tggcccccaaa gaagaagcgg aaggtcggta tccacggagt cccagcagcc     120
gacaagaagt acagcatcgg cctggacatc ggcaccaact ctgtgggctg ggccgtgatc     180
accgacgagt acaaggtgcc cagcaagaaa ttcaaggtgc tgggcaacac cgaccggcac     240
agcatcaaga gaacctgat cggagccctg ctgttcgaca gcggcgaaac agccgaggcc     300
acccggctga gagaaccgc cagaagaaga taccagcagac ggaagaaccg gatctgctat     360
ctgcaagaga tcttcagcaa cgagatggcc aaggtggacg acagcttctt ccacagactg     420
gaagagtcct tcctggtgga agaggataag aagcacgagc ggcacccat cttcggcaac     480 atcgtggacg aggtggccta ccacgagaag tacccaccaa tctaccacct gagaaagaaa     540
ctggtggaca gcaccgacaa ggccgacctg cggctgatct atctggccct ggcccacatg     600
atcaagttcc ggggccactt cctgatcgag ggcgacctga accccgacaa cagcgacgtg     660
gacaagctgt tcatccagct ggtgcagacc tacaaccagc tgttcgagga aaaccccatc     720
aacgccagcg gcgtggacgc caaggccatc ctgtctgcca gactgagcaa gagcagacgg     780
ctggaaaatc tgatcgccca gctgcccggc gagaagaaga tggcctgtt cggaaacctg     840 attgccctga gcctgggcct gaccccaac ttcaagagca cttcgacct ggccgaggat     900
```

```
gccaaactgc agctgagcaa ggacacctac gacgacgacc tggacaacct gctggcccag    960
atcggcgacc agtacgccga cctgtttctg gccgccaaga acctgtccga cgccatcctg   1020
ctgagcgaca tcctgagagt gaacaccgag atcaccaagg ccccctgag cgcctctatg   1080 atcaagagat acgacgagca ccaccaggac ctgaccctgc tgaaagctct cgtgcggcag   1140
cagctgcctg agaagtacaa agagattttc ttcgaccaga gcaagaacgg ctacgccggc   1200
tacattgacg gcggagccag ccaggaagag ttctacaagt tcatcaagcc catcctggaa   1260
aagatggacg gcaccgagga actgctcgtg aagctgaaca gagaggacct gctgcggaag   1320 cagcggaccct tcgacaacgg cagcatcccc caccagatcc acctgggaga gctgcacgcc   1380
attctgcggc ggcaggaaga tttttaccca ttcctgaagg acaaccggga aaagatcgag   1440
aagatcctga ccttccgcat ccctactac gtgggccctc tggccagggg aaacagcaga   1500
ttcgcctgga tgaccagaaa gagcgaggaa accatcaccc cctggaactt cgaggaagtg   1560
gtggacaagg cgcttccgc ccagagcttc atcgagcgga tgaccaactt cgataagaac   1620
ctgcccaacg agaaggtgct gcccaagcac agcctgctgt acgagtactt caccgtgtat   1680
aacgagctga ccaaagtgaa atacgtgacc gagggaatga aaagcccgc cttcctgagc   1740 ggcgagcaga aaaaggccat cgtggacctg ctgttcaaga ccaaccggaa agtgaccgtg   1800
aagcagctga agaggactac cttcaagaaa atcgagtgct tcgactccgt ggaaatctcc   1860
ggcgtggaag atcggttcaa cgcctccctg ggcacatacc acgatctgct gaaaattatc   1920
aaggacaagg acttcctgga caatgaggaa aacgaggaca ttctggaaga tatcgtgctg   1980 acccctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccggcaagac aatcctggat   2160
ttcctgaagt ccgacggctt cgccaacaga aacttcatgc agctgatcca cgacgacagc   2220
ctgaccttta agaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca gcccgagaa catcgtgatc   2400 gaaatggcca gagagaacca gaccacccag aagggacaga agaacagccg cgagagaatg   2460
aagcggatcg aagagggcat caaagagctg ggcagccaga tcctgaaaga acaccccgtg   2520
gaaaacaccc agctgcagaa cgagaagctg tacctgtact acctgcagaa tgggcgggat   2580
atgtacgtgg accaggaact ggacatcaac cggctgtccg actacgatgt ggaccatatc   2640
gtgcctcaga gctttctgaa ggacgactcc atcgacaaca aggtgctgac cagaagcgac   2700
aagaaccggg gcaagagcga caacgtgccc tccgaagagg tcgtgaagaa gatgaagaac   2760
tactggcggc agctgctgaa cgccaagctg attacccaga gaaagttcga caatctgacc   2820
aaggccgaga gaggcggcct gagcgaactg gataaggccg gcttcatcaa gagacagctg   2880
gtggaaaccc ggcagatcac aaagcacgtg gcacagatcc tggactcccg gatgaacact   2940
aagtacgacg agaatgacaa gctgatccgg gaagtgaaag tgatcaccct gaagtccaag   3000
ctggtgtccg atttccggaa ggatttccag ttttacaaag tgcgcgagat caacaactac   3060
caccacgccc acgacgccta cctgaacgcc gtcgtgggaa ccgccctgat caaaaagtac   3120
cctaagctgg aaagcgagtt cgtgtacggc gactacaagg tgtacgacgt gcggaagatg   3180
atcgccaaga gcgagcagga aatcggcaag gctaccgcca gtacttctt ctacagcaac   3240 atcatgaact ttttcaagac cgagattacc ctggccaacg gcgagatccg gaagcggcct   3300
```

```
ctgatcgaga caaacggcga aaccggggag atcgtgtggg ataagggccg ggattttgcc      3360
accgtgcgga aagtgctgag catgccccaa gtgaatatcg tgaaaaagac cgaggtgcag      3420
acaggcggct tcagcaaaga gtctatcctg cccaagagga acagcgataa gctgatcgcc      3480
agaaagaagg actgggaccc taagaagtac ggcggcttcg acagcccac  cgtggcctat      3540 tctgtgctgg tggtggccaa agtggaaaag ggcaagtcca agaaactgaa gagtgtgaaa      3600
gagctgctgg ggatcaccat catggaaaga agcagcttcg agaagaatcc catcgacttt      3660
ctggaagcca agggctacaa agaagtgaaa aaggacctga tcatcaagct gcctaagtac      3720
tccctgttcg agctggaaaa cggccggaag agaatgctgg cctctgccgg cgaactgcag      3780
aagggaaacg aactggccct gccctccaaa tatgtgaact tcctgtacct ggccagccac      3840
tatgagaagc tgaagggctc ccccgaggat aatgagcaga acagctgtt  tgtggaacag      3900 cacaagcact acctggacga gatcatcgag cagatcagcg agttctccaa gagagtgatc      3960
ctggccgacg ctaatctgga caaagtgctg tccgcctaca caagcaccg  ggataagccc      4020 atcagagagc aggccgagaa tatcatccac ctgtttaccc tgaccaatct gggagcccct      4080
gccgccttca gtactttga  caccaccatc gaccggaaga ggtacaccag caccaaagag      4140
gtgctggacg ccacccctga tccaccagagc atcaccggcc tgtacgagac acggatcgac      4200
ctgtctcagc tgggaggcga caaaaggccg gcggccacga aaaaggccgg ccaggcaaaa      4260
aagaaaaagt aa                                                         4272

<210> SEQ ID NO 2
<211> LENGTH: 103
<212> TYPE: DNA
<213> ORGANISM: Artificial sequence
<220> FEATURE:
<223> OTHER INFORMATION: sgRNA (NB-PDS3) sequence and map

<400> SEQUENCE: 2
ttggtagtag cgactccatg gttttagagc tagaaatagc aagttaaaat aaggctagtc        60
cgttatcaac ttgaaaaagt ggcaccgagt cggtgctttt ttt                         103

<210> SEQ ID NO 3
<211> LENGTH: 797
<212> TYPE: DNA
<213> ORGANISM: Artificial sequence
<220> FEATURE:
<223> OTHER INFORMATION: NB-PDS3 selected region

<400> SEQUENCE: 3
gaaacacatc acctaggcgg tttcataccg aggtaacaaa tgattttggt ttctttggtt        60
acatcagctg aatgctttac ttgagaaaag ctttctcctt ttcccgttta ggatcttgtt       120
tatttgcttt cgttttttcta ctcgttaaaa ttttaacttg attttgtggg tgaattataa      180
ctttactcat agtgcgagaa caagtttcgt atggactgta aaagctagaa tcttttttac       240
ttttgcatat aaatttgtgt aataaatgct taagaaccag aatattgaaa aaacaaagga       300
attctacata gtatttaggt tcacaagtgg gacaatcttc ttacagtgaa atatctttat       360
gtcaggctta atttactgct attttgttca gtaaaatgcc ccaaattgga cttgtttctg       420
ccgttaattt gagagtccaa ggtaattcag cttatctttg gagctcgagg tcttctttgg       480
gaactgaaag tcaagatggt cgcttgcaaa ggaatttgtt atgttttggt agtagcgact       540
ccatggggca taagtttaga attcgtactc ccagtgccat gaccagaaga ttgacaaagg       600
```

```
acttcaatcc tttaaaggtt tgttttgaat gcgaaagtgt gatgctgaat ttatgatcac      660
gagcatatat tctctaaaat aagatatctt gccattcagg tagtctgcat tgattatcca      720
agaccggagc tagacaatac agttaactat ttggaggcgg cgttatcatc atcatcattt      780
cgtacttcct cacgccc                                                    797

<210> SEQ ID NO 4
<211> LENGTH: 103
<212> TYPE: DNA
<213> ORGANISM: Artificial sequence
<220> FEATURE:
<223> OTHER INFORMATION: sgRNA (NB.PCNA)

<400> SEQUENCE: 4
tgtgaccgta atatttcaat gttttagagc tagaaatagc aagttaaaat aaggctagtc       60
cgttatcaac ttgaaaaagt ggcaccgagt cggtgctttt ttt                        103

<210> SEQ ID NO 5
<211> LENGTH: 1098
<212> TYPE: DNA
<213> ORGANISM: Artificial sequence
<220> FEATURE:
<223> OTHER INFORMATION: NB-PCNA selected region

<400> SEQUENCE: 5
cctaaccctA atttccccag accttctcaa agcccctttt tcatagaaaa tgttggaatt       60
acggcttgtt cagggaagtc tgctgaagaa ggttctagaa tcaattaagg atctggtgaa      120
cgatgcgaac ttcgattgct ctgccaccgg attctctctg caggccatgg attccagcca      180
cgtagcgttg gtggcgctgc tgctccgatc tgagggtttt gagcactatc gttgtgaccg      240
taatatttca atggggatga accttggtaa catggctaaa atgctcaaat gtgcggggaa      300
tgatgacatc atcacccctca aggctgacga tggcagtgac accgtcactt tcatgtttga      360
aagccccagt aagttccaaa acttattttt cttctgaagc ctatttttt cgtaagttgt       420 gtagcatata ataagacct agaaacattg taaaatttgt tatgtaaagt tgcaaattgt       480
tcattgcctt tcccaaaata tgtgaccttt ttttgctta tgattgctct ttttagtac       540 tttgatatac cttttggtta tttttgacgtg ggaaaaattg cagctaatag tactttttgac      600 agtctttgaa tatcttagat ttaaattttg aaaattatta tctactgatt ctaaataatt      660
ataagtgaaa taaacttgtt tatttagctc aaaattttta taattgatat ttgatccaat      720
agataaaatt gcagctaaat agtgtttttg caatagtgtt tgaatatcaa tgttaatttt      780
tttataaatt ttagctcgga agtgataata ttaaaaaagt ataaaataaa aatgagttaa      840
acttgtttga tttagcttgg aagtgatatt attgacattt gatacaagaa attggcattg      900 gctatttttca tcatagcgtg tggtgttgcg tgtattaagc tgaatatata gttttagaaa      960
ttgtgatttg attctgaatt tggatttact ctactattct tccattgtta tggctgggtg      1020
taactaagta tactgtaacg tatcacagcc caagacaaga ttgctgattt tgagatgaag      1080
ctgatggaca ttgacagt                                                   1098

<210> SEQ ID NO 6
<211> LENGTH: 9663
<212> TYPE: DNA
<213> ORGANISM: Artificial sequence
<220> FEATURE:
<223> OTHER INFORMATION: pYL156 RNA2

<400> SEQUENCE: 6
```

```
aagcttgcat gcctgcaggt caacatggtg gagcacgaca ctctcgtcta ctccaagaat      60
atcaaagata cagtctcaga agaccagagg gctattgaga cttttcaaca aagggtaata    120
tcgggaaacc tcctcggatt ccattgccca gctatctgtc acttcatcga aaggacagta    180
gaaaaggaag atggcttcta caaatgccat cattgcgata aaggaaaggc tatcgttcaa    240
gatgcctcta ccgacagtgg tcccaaagat ggaccccccac ccacgaggaa catcgtggaa   300
aaagaagacg ttccaaccac gtcttcaaag caagtggatt gatgtgatgg tcaacatggt   360
ggagcacgac actctcgtct actccaagaa tatcaaagat acagtctcag aagaccagag   420
ggctattgag acttttcaac aaagggtaat atcgggaaac ctcctcggat tccattgccc   480
agctatctgt cacttcatcg aaaggacagt agaaaaggaa gatggcttct acaaatgcca   540
tcattgcgat aaaggaaagg ctatcgttca agatgcctct accgacagtg gtcccaaaga   600 tggacccccca cccacgagga acatcgtgga aaaagaagac gttccaacca cgtcttcaaa   660
gcaagtggat tgatgtgata tctccactga cgtaagggat gacgcacaat cccactatcc   720
ttcgcaagac ccttcctcta tataaggaag ttcatttcat ttggagagga taaaacattg   780
cacctatggt gttgccctgg ctggggtatg tcagtgatcg cagtagaatg tactaattga   840
caagttggag aatacggtag aacgtcctta tccaacacag cctttatccc tctccctgac   900 gaggttttg tcagtgtaat atttcttttt gaactatcca gcttagtacc gtacgggaaa    960
gtgactggtg tgcttatctt tgaaatgtta ctttgggttt cggttcttta ggttagtaag   1020
aaagcacttg tcttctcata caaaggaaaa cctgagacgt atcgcttacg aaagtagcaa   1080
tgaaagaaag gtggtggttt taatcgctac cgcaaaaacg atgggtcgt tttaattaac    1140 ttctcctacg caagcgtcta aacggacgtt ggggttttgc tagtttcttt agagaaaact   1200
agctaagtct ttaatgttat cattagagat ggcataaata taatacttgt gtctgctgat   1260
aagatcattt taatttggac gattagactt gttgaactac aggttactga atcacttgcg   1320
ctaatcaaca tgggagatat gtacgatgaa tcatttgaca agtcgggcgg tcctgctgac   1380 ttgatgacg attcttgggt ggaatcagtt tcgtggaaag atctgttgaa gaagttacac    1440
agcataaaat ttgcactaca gtctggtaga gatgagatca ctgggttact agcggcactg   1500
aatagacagt gtccttattc accatatgag cagtttccag ataagaaggt gtatttcctt   1560
ttagactcac gggctaacag tgctcttggt gtgattcaga acgcttcagc gttcaagaga   1620
cgagctgatg agaagaatgc agtggcgggt gttacaaata ttcctgcgaa tccaaacaca   1680
acggttacga cgaaccaagg gagtactact actaccaagg cgaacactgg ctcgactttg   1740
gaagaagact tgtacactta ttacaaattc gatgatgcct ctacagcttt ccacaaatct   1800
ctaacttcgt tagagaacat ggagttgaag agttattacc gaaggaactt tgagaaagta   1860
ttcgggatta agtttggtgg agcagctgct agttcatctg caccgcctcc agcgagtgga   1920
ggtccgatac gtcctaatcc ctagggattt aaggacgtga actctgttga gatctctgtg   1980
aaattcagag ggtgggtgat accatattca ctgatgccat tagcgacatc taaatagggc   2040
taattgtgac taatttgagg gaatttcctt taccattgac gtcagtgtcg ttggtagcat   2100
ttgagtttcg caatgcacga attacttagg aagtggcttg acgacactaa tgtgttattg   2160
ttagataatg gtttggtggt caaggtacgt agtagagtcc cacatattcg cacgtatgaa   2220
gtaattggaa agttgtcagt ttttgataat tcactgggag atgatacgct gtttgaggga   2280
aaagtagaga acgtatttgt ttttatgttc aggcggttct tgtgtgtcaa caaagatgga   2340
```

```
cattgttact caaggaagca cgatgagctt tattattacg gacgagtgga cttagattct   2400
gtgagtaagg ttaccgaatt ctctagaagg cctccatggg gatccggtac cgagctcacg   2460
cgtctcgagg cccgggcatg tcccgaagac attaaactac ggttctttaa gtagatccgt   2520
gtctgaagtt ttaggttcaa tttaaaccta cgagattgac attctcgact gatcttgatt   2580
gatcggtaag tcttttgtaa tttaatttc tttttgattt tattttaaat tgttatctgt    2640
ttctgtgtat agactgtttg agatcggcgt tggccgact cattgtctta ccataggga     2700 acggactttg tttgtgttgt tattttattt gtattttatt aaaattctca acgatctgaa   2760
aaagcctcgc ggctaagaga ttgttggggg gtgagtaagt acttttaaag tgatgatggt   2820
tacaaaggca aagggtaa aaccctcgc ctacgtaagc gttattacgc ccgtctgtac      2880
ttatatcagt acactgacga gtccctaaag gacgaaacgg gagaacgcta gccaccacca   2940
ccaccaccac gtgtgaatta caggtgacca gctcgaattt ccccgatcgt tcaaacattt   3000
ggcaataaag tttcttaaga ttgaatcctg ttgccggtct tgcgatgatt atcatataat   3060
ttctgttgaa ttacgttaag catgtaataa ttaacatgta atgcatgacg ttatttatga   3120
gatgggtttt tatgattaga gtcccgcaat tatacatttta atacgcgata gaaaacaaaa   3180
tatagcgcgc aaactaggat aaattatcgc gcgcggtgtc atctatgtta ctagatcggg   3240
aattaaacta tcagtgtttg acaggatata ttggcgggta aacctaagag aaaagagcgt   3300
ttattagaat aacggatatt taaagggcg tgaaaaggtt tatccgttcg tccatttgta    3360
tgtgcatgcc aaccacaggg ttcccctcgg gatcaaagta ctttgatcca acccctccgc   3420
tgctatagtg cagtcggctt ctgacgttca gtgcagccgt cttctgaaaa cgacatgtcg   3480
cacaagtcct aagttacgcg acaggctgcc gccctgccct tttcctggcg ttttcttgtc   3540
gcgtgtttta gtcgcataaa gtagaatact tgcgactaga accggagaca ttacgccatg   3600
aacaagagcg ccgccgctgg cctgctgggc tatgcccgcg tcagcaccga cgaccaggac   3660
ttgaccaacc aacgggccga actgcacgcg gccggctgca ccaagctgtt ttccgagaag   3720
atcaccggca ccaggcgcga ccgcccggag ctggccagga tgcttgacca cctacgccct   3780
ggcgacgttg tgacagtgac caggctagac cgcctggccc gcagcacccg cgacctactg   3840
gacattgccg agcgcatcca ggaggccggc gcgggcctgc gtagcctggc agagccgtgg   3900
gccgacacca ccacgccggc cggccgcatg gtgttgaccg tgttcgccgg cattgccgag   3960
ttcgagcgtt ccctaatcat cgaccgcacc cggagcgggc gcgaggccgc caaggcccga   4020
ggcgtgaagt ttggcccccg ccctaccctc accccggcac agatcgcgca cgcccgcgag   4080
ctgatcgacc aggaaggccg caccgtgaaa gaggcggctg cactgcttgg cgtgcatcgc   4140
tcgaccctgt accgcgcact tgagcgcagc gaggaagtga cgcccaccga ggccaggcgg   4200
cgcggtgcct tccgtgagga cgcattgacc gaggccgacg cctggcggc cgccgagaat   4260 gaacgccaag aggaacaagc atgaaaccgc accaggacgg ccaggacgaa ccgttttca   4320 ttaccgaaga gatcgaggcg gagatgatcg cggccgggta cgtgttcgag ccgcccgcgc   4380
acgtctcaac cgtgcggctg catgaaatcc tggccggttt gtctgatgcc aagctggcgg   4440
cctggccgga cagcttggcc gctgaagaaa ccgagcgccg ccgtctaaaa aggtgatgtg   4500
tatttgagta aaacagcttg cgtcatgcgg tcgctgcgta tatgatgcga tgagtaaata   4560
aacaaatacg caaggggaac gcatgaaggt tatcgctgta cttaaccaga aaggcgggtc   4620
aggcaagacg accatcgcaa cccatctagc ccgcgccctg caactcgccg ggccgatgt    4680 tctgttagtc gattccgatc cccagggcag tgcccgcgat tgggcggccg tgcggaagag   4740
```

```
tcaaccgcta accgttgtcg gcatcgaccg cccgacgatt gaccgcgacg tgaaggccat    4800
cggccggcgc gacttcgtag tgatcgacgg agcgccccag gcggcggact tggctgtgtc    4860
cgcgatcaag gcagccgact tcgtgctgat tccggtgcag ccaagccctt acgacatatg    4920
ggccaccgcc gacctggtgg agctggttaa gcagcgcatt gaggtcacgg atggaaggct    4980
acaagcggcc tttgtcgtgt cgcgggcgat caaaggcacg cgcatcggcg gtgaggttgc    5040
cgaggcgctg gccgggtacg agctgcccat tcttgagtcc cgtatcacgc agcgcgtgag    5100
ctacccaggc actgccgccg ccggcacaac cgttcttgaa tcagaacccg agggcgacgc    5160
tgcccgcgag gtccaggcgc tggccgctga aattaaatca aaactcattt gagttaatga    5220
ggtaaagaga aaatgagcaa aagcacaaac acgctaagtg ccggccgtcc gagcgcacgc    5280
agcagcaagg ctgcaacgtt ggccagcctg gcagacacgc cagccatgaa gcgggtcaac    5340
tttcagttgc cggcggagga tcacaccaag ctgaagatgt acgcggtacg ccaaggcaag    5400
accattaccg agctgctatc tgaatacatc gcgcagctac cagagtaaat gagcaaatga    5460
ataaatgagt agatgaattt tagcggctaa aggaggcggc atggaaaatc aagaacaacc    5520
aggcaccgac gccgtggaat gccccatgtg tggaggaacg ggcggttggc caggcgtaag    5580
cggctgggtt gtctgccggc cctgcaatgg cactggaacc cccaagcccg aggaatcggc    5640
gtgacggtcg caaaccatcc ggcccggtac aaatcggcgc ggcgctgggt gatgacctgg    5700
tggagaagtt gaaggccgcg caggccgccc agcggcaacg catcgaggca gaagcacgcc    5760
ccggtgaatc gtggcaagcg gccgctgatc gaatccgcaa agaatcccgg caaccgccgg    5820
cagccggtgc gccgtcgatt aggaagccgc ccaagggcga cgagcaacca gattttttcg    5880
ttccgatgct ctatgacgtg ggcacccgcg atagtcgcag catcatggac gtggccgttt    5940
tccgtctgtc gaagcgtgac cgacgagctg gcgaggtgat ccgctacgag cttccagacg    6000
ggcacgtaga ggtttccgca gggccggccg catggccag tgtgtgggat tacgacctgg    6060
tactgatggc ggtttcccat ctaaccgaat ccatgaaccg ataccgggaa gggaagggag    6120
acaagcccgg ccgcgtgttc cgtccacacg ttgcggacgt actcaagttc tgccggcgag    6180
ccgatggcgg aaagcagaaa gacgacctgg tagaaacctg cattcggtta aacaccacgc    6240
acgttgccat gcagcgtacg aagaaggcca agaacggccg cctggtgacg gtatccgagg    6300
gtgaagcctt gattagccgc tacaagatcg taaagagcga accgggcgg ccggagtaca    6360
tcgagatcga gctagctgat tggatgtacc gcgagatcac agaaggcaag aacccggacg    6420
tgctgacggt tcaccccgat tacttttttga tcgatcccgg catcggccgt tttctctacc    6480
gcctggcacg ccgcgccgca ggcaaggcag aagccagatg gttgttcaag acgatctacg    6540
aacgcagtgg cagcgccgga gagttcaaga agttctgttt caccgtgcgc aagctgatcg    6600
ggtcaaatga cctgccggag tacgatttga aggaggaggc ggggcaggct ggcccgatcc    6660
tagtcatgcg ctaccgcaac ctgatcgagg gcgaagcatc cgccggttcc taatgtacgg    6720
agcagatgct agggcaaatt gccctagcag gggaaaaagg tcgaaaaggt ctctttcctg    6780
tggatagcac gtacattggg aacccaaagc cgtacattgg gaaccggaac ccgtacattg    6840
ggaacccaaa gccgtacatt gggaaccggt cacacatgta agtgactgat ataaaagaga    6900
aaaaaggcga ttttccgcc taaaactctt taaaacttat taaaactctt aaaacccgcc    6960
tggcctgtgc ataactgtct ggccagcgca cagccgaaga gctgcaaaaa gcgcctaccc    7020
ttcggtcgct gcgctcccta cgccccgccg cttcgcgtcg gcctatcgcg gccgctggcc    7080
```

```
gctcaaaaat ggctggccta cggccaggca atctaccagg gcgcggacaa gccgcgccgt    7140
cgccactcga ccgccggcgc ccacatcaag gcaccctgcc tcgcgcgttt cggtgatgac    7200
ggtgaaaacc tctgacacat gcagctcccg gagacggtca cagcttgtct gtaagcggat    7260
gccgggagca gacaagcccg tcagggcgcg tcagcgggtg ttggcgggtg tcggggcgca    7320
gccatgaccc agtcacgtag cgatagcgga gtgtatactg gcttaactat gcggcatcag    7380
agcagattgt actgagagtg caccatatgc ggtgtgaaat accgcacaga tgcgtaagga    7440
gaaaataccg catcaggcgc tcttccgctt cctcgctcac tgactcgctg cgctcggtcg    7500
ttcggctgcg gcgagcggta tcagctcact caaaggcggt aatacggtta ccacagaat     7560 caggggataa cgcaggaaag aacatgtgag caaaaggcca gcaaaaggcc aggaaccgta    7620
aaaaggccgc gttgctggcg ttttccata ggctccgccc ccctgacgag catcacaaaa     7680
atcgacgctc aagtcagagg tggcgaaacc cgacaggact ataaagatac caggcgtttc    7740
cccctggaag ctccctcgtg cgctctcctg ttccgaccct gccgcttacc ggatacctgt    7800
ccgcctttct cccttcggga agcgtggcgc tttctcatag ctcacgctgt aggtatctca    7860
gttcggtgta ggtcgttcgc tccaagctgg gctgtgtgca cgaaccccc gttcagcccg     7920 accgctgcgc cttatccggt aactatcgtc ttgagtccaa cccggtaaga cacgacttat    7980
cgccactggc agcagccact ggtaacagga ttagcagagc gaggtatgta ggcggtgcta    8040
cagagttctt gaagtggtgg cctaactacg gctacactag aaggacagta tttggtatct    8100
gcgctctgct gaagccagtt accttcggaa aaagagttgg tagctcttga tccggcaaac    8160
aaaccaccgc tggtagcggt ggtttttttg tttgcaagca gcagattacg cgcagaaaaa    8220
aaggatctca agaagatcct ttgatctttt ctacgggtc tgacgctcag tggaacgaaa     8280
actcacgtta agggattttg gtcatgcatt ctaggtacta aaacaattca tccagtaaaa    8340
tataatattt tattttctcc caatcaggct tgatccccag taagtcaaaa aatagctcga    8400
catactgttc ttccccgata tcctccctga tcgaccggac gcagaaggca atgtcatacc    8460
acttgtccgc cctgccgctt ctcccaagat caataaagcc acttactttg ccatctttca    8520
caaagatgtt gctgtctccc aggtcgccgt gggaaaagac aagttcctct cgggcttttt    8580
ccgtctttaa aaatcatac agctcgcgcg gatctttaaa tggagtgtct tcttcccagt     8640
tttcgcaatc cacatcggcc agatcgttat tcagtaagta atccaattcg gctaagcggc    8700
tgtctaagct attcgtatag ggacaatccg atatgtcgat ggagtgaaag agcctgatgc    8760
actccgcata cagctcgata atcttttcag ggctttgttc atcttcatac tcttccgagc    8820
aaaggacgcc atcggcctca ctcatgagca gattgctcca gccatcatgc cgttcaaagt    8880
gcaggacctt tggaacaggc agctttcctt ccagccatag catcatgtcc tttcccgtt    8940 ccacatcata ggtggtccct ttataccggc tgtccgtcat ttttaaatat aggttttcat    9000
tttctcccac cagcttatat accttagcag gagacattcc ttccgtatct tttacgcagc    9060
ggtatttttc gatcagtttt ttcaattccg gtgatattct cattttagcc atttattatt    9120
tccttcctct tttctacagt atttaaagat accccaagaa gctaattata acaagacgaa    9180
ctccaattca ctgttccttg cattctaaaa ccttaaatac cagaaaacag ctttttcaaa    9240
gttgttttca agttggcgt ataacatagt atcgacggag ccgattttga aaccgcggtg     9300
atcacaggca gcaacgctct gtcatcgtta caatcaacat gctaccctcc gcgagatcat    9360
ccgtgtttca aacccggcag cttagttgcc gttcttccga atagcatcgg taacatgagc    9420
aaagtctgcc gccttacaac ggctctcccg ctgacgccgt cccggactga tgggctgcct    9480
```

```
gtatcgagtg gtgattttgt gccgagctgc cggtcgggga gctgttggct ggctggtggc    9540
aggatatatt gtggtgtaaa caaattgacg cttagacaac ttaataacac attgcggacg    9600
tttttaatgt actgaattaa cgccgaatta attcctaggc caccatgttg ggcccggcgc    9660
gcc                                                                  9663

<210> SEQ ID NO 7
<211> LENGTH: 304
<212> TYPE: DNA
<213> ORGANISM: Artificial sequence
<220> FEATURE:
<223> OTHER INFORMATION: Arabidopsis U6 promoter sequence for expression
      of sgRNA

<400> SEQUENCE: 7
agaaatctca aaattccggc agaacaattt tgaatctcga tccgtagaaa cgagacggtc      60
attgttttag ttccaccacg attatatttg aaatttacgt gagtgtgagt gagacttgca    120
taagaaaata aaatctttag ttgggaaaaa attcaataat ataaatgggc ttgagaagga    180
agcgagggat aggcctttt ctaaaatagg cccatttaag ctattaacaa tcttcaaaag    240
taccacagcg cttaggtaaa gaaagcagct gagtttatat atggttagag acgaagtagt    300
gatt                                                                 304

<210> SEQ ID NO 8
<211> LENGTH: 9544
<212> TYPE: DNA
<213> ORGANISM: Artificial sequence
<220> FEATURE:
<223> OTHER INFORMATION: RNA2-pEBV

<400> SEQUENCE: 8
aagcttgcat gcctgcaggt caacatggtg gagcacgaca ctctcgtcta ctccaagaat      60
atcaaagata cagtctcaga agaccagagg gctattgaga ctttcaaca aagggtaata    120 tcgggaaacc tcctcggatt ccattgccca gctatctgtc acttcatcga aggacagta    180 gaaaggaag atggcttcta caaatgccat cattgcgata aaggaaaggc tatcgttcaa    240
gatgcctcta ccgacagtgg tcccaaagat ggacccccac ccacgaggaa catcgtggaa    300
aaagaagacg ttccaaccac gtcttcaaag caagtggatt gatgtgatgg tcaacatggt    360
ggagcacgac actctcgtct actccaagaa tatcaaagat acagtctcag aagaccagag    420 gctattgag acttttcaac aaagggtaat atcgggaaac ctcctcggat tccattgccc    480
agctatctgt cacttcatcg aaaggacagt agaaaaggaa gatggcttct acaaatgcca    540
tcattgcgat aaaggaaagg ctatcgttca agatgcctct accgacagtg gtcccaaaga    600
tggaccccca cccacgagga acatcgtgga aaaagaagac gttccaacca cgtcttcaaa    660
gcaagtggat tgatgtgata tctccactga cgtaagggga gacgcacaat cccactatcc    720
ttcgcaagac ccttcctcta taaggaag ttcatttcat ttggagagga taaaacattg    780
cacctatggt gttgccctgg ctggggtatg tcagtgatcg cagtagaatg tactaattga    840
caagttggag aatacggtag aacgtcctta tccaacacag cctttatccc tctccctgac    900 gaggttttg tcagtgtaat atttcttttt gaactatcca gcttagtacc gtacgggaaa    960
gtgactggtg tgcttatctt tgaaatgtta ctttgggttt cggttcttta ggttagtaag    1020
aaagcacttg tcttctcata caaaggaaaa cctgagacga atcgcttacg aaagtagcaa    1080
tgaaagaaag gtggtggttt taatcgctac cgcaaaaacg atgggtcgt tttaattaac    1140
```

```
ttctcctacg caagcgtcta aacggacgtt ggggttttgc tagtttcttt agagaaaact    1200
agctaagtct ttaatgttat cattagagat ggcataaata taatacttgt gtctgctgat    1260
aagatcattt taatttggac gattagactt gttgaactac aggttactga atcacttgcg    1320
ctaatcaaca tgggagatat gtacgatgaa tcatttgaca agtcgggcgg tcctgctgac    1380
ttgatggacg attcttgggt ggaatcagtt tcgtggaaag atctgttgaa gaagttacac    1440
agcataaaat ttgcactaca gtctggtaga gatgagatca ctgggttact agcggcactg    1500
aatagacagt gtccttattc accatatgag cagtttccag ataagaaggt gtatttcctt    1560
ttagactcac gggctaacag tgctcttggt gtgattcaga acgcttcagc gttcaagaga    1620
cgagctgatg agaagaatgc agtggcgggt gttacaaata ttcctgcgaa tccaaacaca    1680
acggttacga cgaaccaagg gagtactact actaccaagg cgaacactgg ctcgactttg    1740
gaagaagact tgtacactta ttacaaattc gatgatgcct ctacagcttt ccacaaatct    1800
ctaacttcgt tagagaacat ggagttgaag agttattacc gaaggaactt tgagaaagta    1860
ttcgggatta agtttggtgg agcagctgct agttcatctg caccgcctcc agcgagtgga    1920
ggtccgatac gtcctaatcc ctagggattt aaggacgtga actctgttga gatctctgtg    1980
aaattcagag ggtgggtgat accatattca ctgatgccat tagcgacatc taaatagggc    2040
taattgtgac taatttgagg gaatttcctt taccattgac gtcagtgtcg ttggtagcat    2100
ttgagtttcg aattcgagca tcttgttctg gggtttcaca ctatctttag agaaagtgtt    2160
aagttaatta agttatctta attaagagca taattatact gatttgtctc tcgttgatag    2220
agtctatcat tctgttacta aaaatttgac aactcggttt gctgacctac tggttactgt    2280
atcacttacc cgagttaacg agtctagaag gcctccatgg ggatccggta ccgagctcac    2340
gcgtctcgag gcccgggcat gtcccgaaga cattaaacta cggttcttta agtagatccg    2400
tgtctgaagt tttaggttca atttaaacct acgagattga cattctcgac tgatcttgat    2460
tgatcggtaa gtcttttgta atttaatttt cttttgatt ttattttaaa ttgttatctg     2520
tttctgtgta tagactgttt gagatcggcg tttggccgac tcattgtctt accatagggg    2580
aacggacttt gtttgtgttg ttattttatt tgtatttat taaaattctc aacgatctga    2640
aaaagcctcg cggctaagag attgttgggg ggtgagtaag tacttttaaa gtgatgatgg    2700
ttacaaaggc aaaaggggta aaacccctcg cctacgtaag cgttattacg cccgtctgta    2760
cttatatcag tacactgacg agtccctaaa ggacgaaacg ggagaacgct agccaccacc    2820
accaccacca cgtgtgaatt acaggtgacc agctcgaatt tccccgatcg ttcaaacatt    2880
tggcaataaa gtttcttaag attgaatcct gttgccggtc ttgcgatgat tatcatataa    2940
tttctgttga attacgttaa gcatgtaata attaacatgt aatgcatgac gttatttatg    3000
agatgggttt ttatgattag agtcccgcaa ttatacattt aatacgcgat agaaaacaaa    3060
atatagcgcg caaactagga taaattatcg cgcgcggtgt catctatgtt actagatcgg    3120
gaattaaact atcagtgttt gacaggatat attggcgggt aaacctaaga gaaaagagcg    3180
tttattagaa taacggatat ttaaaagggc gtgaaaaggt ttatccgttc gtccatttgt    3240
atgtgcatgc caaccacagg gttccccctcg ggatcaaagt actttgatcc aacccctccg    3300
ctgctatagt gcagtcggct tctgacgttc agtgcagccg tcttctgaaa cgacatgtc     3360
gcacaagtcc taagttacgc gacaggctgc cgccctgccc ttttcctggc gttttcttgt    3420
cgcgtgtttt agtcgcataa agtagaatac ttgcgactag aaccggagac attacgccat    3480
```

-continued

```
gaacaagagc gccgccgctg gcctgctggg ctatgcccgc gtcagcaccg acgaccagga    3540
cttgaccaac caacgggccg aactgcacgc ggccggctgc accaagctgt tttccgagaa    3600
gatcaccggc accaggcgcg accgcccgga gctggccagg atgcttgacc acctacgccc    3660
tggcgacgtt gtgacagtga ccaggctaga ccgcctggcc cgcagcaccc gcgacctact    3720
ggacattgcc gagcgcatcc aggaggccgg cgcgggcctg cgtagcctgg cagagccgtg    3780
ggccgacacc accacgccgg ccggccgcat ggtgttgacc gtgttcgccg gcattgccga    3840
gttcgagcgt tccctaatca tcgaccgcac ccggagcggg cgcgaggccg ccaaggcccg    3900
aggcgtgaag tttggccccc gccctaccct caccccggca cagatcgcgc acgcccgcga    3960
gctgatcgac caggaaggcc gcaccgtgaa agaggcggct gcactgcttg gcgtgcatcg    4020
ctcgaccctg taccgcgcac ttgagcgcag cgaggaagtg acgcccaccg aggccaggcg    4080
gcgcggtgcc ttccgtgagg acgcattgac cgaggccgac gccctggcgg ccgccgagaa    4140
tgaacgccaa gaggaacaag catgaaaccg caccaggacg gccaggacga accgtttttc    4200
attaccgaag agatcgaggc ggagatgatc gcggccgggt acgtgttcga gccgcccgcg    4260
cacgtctcaa ccgtgcggct gcatgaaatc ctggccggtt tgtctgatgc caagctggcg    4320
gcctggccgg ccagcttggc cgctgaagaa accgagcgcc gccgtctaaa aggtgatgt    4380 gtatttgagt aaaacagctt gcgtcatgcg gtcgctgcgt atatgatgcg atgagtaaat    4440
aaacaaatac gcaaggggaa cgcatgaagg ttatcgctgt acttaaccag aaaggcgggt    4500
caggcaagac gaccatcgca acccatctag cccgcgccct gcaactcgcc ggggccgatg    4560
ttctgttagt cgattccgat ccccaggca gtgcccgcga ttgggcggcc gtgcgggaag    4620
atcaaccgct aaccgttgtc ggcatcgacc gcccgacgat tgaccgcgac gtgaaggcca    4680
tcggccggcg cgacttcgta gtgatcgacg gagcgcccca ggcggcggac ttggctgtgt    4740
ccgcgatcaa ggcagccgac ttcgtgctga ttccggtgca gccaagccct tacgacatat    4800
gggccaccgc cgacctggtg gagctggtta agcagcgcat tgaggtcacg gatgaaggc    4860 tacaagcggc ctttgtcgtg tcgcgggcga tcaaaggcac gcgcatcggc ggtgaggttg    4920
ccgaggcgct ggccgggtac gagctgccca ttcttgagtc ccgtatcacg cagcgcgtga    4980
gctacccagg cactgccgcc gccggcacaa ccgttcttga atcagaaccc gagggcgacg    5040
ctgcccgcga ggtccaggcg ctggccgctg aaattaaatc aaaactcatt tgagttaatg    5100
aggtaaagag aaaatgagca aaagcacaaa cacgctaagt gccggccgtc cgagcgcacg    5160
cagcagcaag gctgcaacgt tggccagcct ggcagacacg ccagccatga gcgggtcaa    5220 cttttcagttg ccggcggagg atcacaccaa gctgaagatg tacgcggtac gccaaggcaa    5280
gaccattacc gagctgctat ctgaatacat cgcgcagcta ccagagtaaa tgagcaaatg    5340
aataaatgag tagatgaatt ttagcggcta aaggaggcgg catggaaaat caagaacaac    5400
caggcaccga cgccgtggaa tgccccatgt gtggaggaac gggcggttgg ccaggcgtaa    5460
gcggctgggt tgtctgccgg ccctgcaatg gcactggaac ccccaagccc gaggaatcgg    5520
cgtgacggtc gcaaaccatc cggcccggta caaatcggcg cggcgctggg tgatgacctg    5580
gtggagaagt tgaaggccgc gcaggccgcc cagcggcaac gcatcgaggc agaagcacgc    5640
cccggtgaat cgtggcaagc ggccgctgat cgaatccgca agaatcccg caaccgccg    5700 gcagccggtg cgccgtcgat taggaagccg cccaagggcg acgagcaacc agatttttc    5760 gttccgatgc tctatgacgt gggcacccgc gatagtcgca gcatcatgga cgtgccgtt    5820 ttccgtctgt cgaagcgtga ccgacgagct ggcgaggtga tccgctacga gcttccagac    5880
```

```
gggcacgtag aggtttccgc agggccggcc ggcatggcca gtgtgtggga ttacgacctg    5940
gtactgatgg cggtttccca tctaaccgaa tccatgaacc gataccggga agggaaggga    6000
gacaagcccg gccgcgtgtt ccgtccacac gttgcggacg tactcaagtt ctgccggcga    6060
gccgatggcg gaaagcagaa agacgacctg gtagaaacct gcattcggtt aaacaccacg    6120
cacgttgcca tgcagcgtac gaagaaggcc aagaacggcc gcctggtgac ggtatccgag    6180
ggtgaagcct tgattagccg ctacaagatc gtaaagagcg aaaccgggcg gccggagtac    6240
atcgagatcg agctagctga ttggatgtac cgcgagatca cagaaggcaa gaacccggac    6300
gtgctgacgg ttcaccccga ttacttttg atcgatcccg gcatcggccg ttttctctac     6360
cgcctggcac gccgcgccgc aggcaaggca gaagccagat ggttgttcaa gacgatctac    6420
gaacgcagtg gcagcgccgg agagttcaag aagttctgtt tcaccgtgcg caagctgatc    6480
gggtcaaatg acctgccgga gtacgatttg aaggaggagg cggggcaggc tggcccgatc    6540
ctagtcatgc gctaccgcaa cctgatcgag ggcgaagcat ccgccggttc ctaatgtacg    6600
gagcagatgc tagggcaaat tgccctagca ggggaaaaag gtcgaaaagg tctctttcct    6660
gtggatagca cgtacattgg gaacccaaag ccgtacattg gaaccggaa cccgtacatt     6720 gggaacccaa agccgtacat tgggaaccgg tcacacatgt aagtgactga tataaaagag    6780
aaaaaaggcg attttccgc ctaaaactct ttaaaactta ttaaaactct taaacccgc      6840 ctggcctgtg cataactgtc tggccagcgc acagccgaag agctgcaaaa agcgcctacc    6900
cttcggtcgc tgcgctccct acgccccgcc gcttcgcgtc ggcctatcgc ggccgctggc    6960
cgctcaaaaa tggctggcct acggccaggc aatctaccag ggcgcggaca agccgcgccg    7020
tcgccactcg accgccggcg cccacatcaa ggcaccctgc ctcgcgcgtt tcggtgatga    7080
cggtgaaaac ctctgacaca tgcagctccc ggagacggtc acagcttgtc tgtaagcgga    7140
tgccgggagc agacaagccc gtcagggcgc gtcagcgggt gttggcgggt gtcggggcgc    7200
agccatgacc cagtcacgta gcgatagcgg agtgtatact ggcttaacta tgcggcatca    7260
gagcagattg tactgagagt gcaccatatg cggtgtgaaa taccgcacag atgcgtaagg    7320
agaaaatacc gcatcaggcg ctcttccgct tcctcgctca ctgactcgct gcgctcggtc    7380
gttcggctgc ggcgagcggt atcagctcac tcaaaggcgg taatacggtt atccacagaa    7440
tcaggggata acgcaggaaa gaacatgtga gcaaaaggcc agcaaaaggc caggaaccgt    7500
aaaaaggccg cgttgctggc gttttccat aggctccgcc ccctgacga gcatcacaaa      7560 aatcgacgct caagtcagag gtggcgaaac ccgacaggac tataaagata ccaggcgttt    7620
ccccctggaa gctccctcgt gcgctctcct gttccgaccc tgccgcttac cggatacctg    7680
tccgcctttc tcccttcggg aagcgtggcg ctttctcata gctcacgctg taggtatctc    7740
agttcggtgt aggtcgttcg ctccaagctg ggctgtgtgc acgaaccccc cgttcagccc    7800
gaccgctgcg ccttatccgg taactatcgt cttgagtcca acccggtaag acacgactta    7860
tcgccactgg cagcagccac tggtaacagg attagcagag cgaggtatgt aggcggtgct    7920
acagagttct tgaagtggtg gcctaactac ggctacacta aaggacagt atttggtatc     7980 tgcgctctgc tgaagccagt taccttcgga aaaagagttg gtagctcttg atccggcaaa    8040
caaaccaccg ctggtagcgg tggtttttt gtttgcaagc agcagattac gcgcagaaaa     8100
aaaggatctc aagaagatcc tttgatcttt tctacgggt ctgacgctca gtggaacgaa     8160
aactcacgtt aagggatttt ggtcatgcat tctaggtact aaaacaattc atccagtaaa    8220
```

| | | | | |
|---|---|---|---|---|
| atataatatt | ttattttctc | ccaatcaggc | ttgatcccca | gtaagtcaaa | aaatagctcg | 8280 |
| acatactgtt | cttccccgat | atcctccctg | atcgaccgga | cgcagaaggc | aatgtcatac | 8340 |
| cacttgtccg | ccctgccgct | tctcccaaga | tcaataaagc | cacttacttt | gccatctttc | 8400 |
| acaaagatgt | tgctgtctcc | caggtcgccg | tgggaaaaga | caagttcctc | ttcgggcttt | 8460 |
| tccgtcttta | aaaatcata | cagctcgcgc | ggatctttaa | atggagtgtc | ttcttcccag | 8520 |
| ttttcgcaat | ccacatcggc | cagatcgtta | ttcagtaagt | aatccaattc | ggctaagcgg | 8580 |
| ctgtctaagc | tattcgtata | gggacaatcc | gatatgtcga | tggagtgaaa | gagcctgatg | 8640 |
| cactccgcat | acagctcgat | aatcttttca | gggctttgtt | catcttcata | ctcttccgag | 8700 |
| caaaggacgc | catcggcctc | actcatgagc | agattgctcc | agccatcatg | ccgttcaaag | 8760 |
| tgcaggacct | ttggaacagg | cagctttcct | tccagccata | gcatcatgtc | cttttcccgt | 8820 |
| tccacatcat | aggtggtccc | tttataccgg | ctgtccgtca | ttttaaata | taggttttca | 8880 |
| ttttctccca | ccagcttata | taccttagca | ggagacattc | cttccgtatc | ttttacgcag | 8940 |
| cggtatttt | cgatcagttt | tttcaattcc | ggtgatattc | tcattttagc | catttattat | 9000 |
| ttccttcctc | ttttctacag | tatttaaaga | taccccaaga | agctaattat | aacaagacga | 9060 |
| actccaattc | actgttcctt | gcattctaaa | accttaaata | ccagaaaaca | gcttttcaa | 9120 |
| agttgtttc | aaagttggcg | tataacatag | tatcgacgga | gccgattttg | aaaccgcggt | 9180 |
| gatcacaggc | agcaacgctc | tgtcatcgtt | acaatcaaca | tgctaccctc | cgcgagatca | 9240 |
| tccgtgtttc | aaacccggca | gcttagttgc | cgttcttccg | aatagcatcg | gtaacatgag | 9300 |
| caaagtctgc | cgccttacaa | cggctctccc | gctgacgccg | tcccggactg | atgggctgcc | 9360 |
| tgtatcgagt | ggtgattttg | tgccgagctg | ccggtcgggg | agctgttggc | tggctggtgg | 9420 |
| caggatatat | tgtggtgtaa | acaaattgac | gcttagacaa | cttaataaca | cattgcggac | 9480 |
| gttttaatg | tactgaatta | acgccgaatt | aattcctagg | ccaccatgtt | gggcccggcg | 9540 |
| cgcc | | | | | 9544 |

<210> SEQ ID NO 9
<211> LENGTH: 6791
<212> TYPE: DNA
<213> ORGANISM: Artificial sequence
<220> FEATURE:
<223> OTHER INFORMATION: YL192 (RNA1)

<400> SEQUENCE: 9

| | | | | |
|---|---|---|---|---|
| ataaaacatt | tcaatccttt | gaacgcggta | gaacgtgcta | attggatttt | ggtgagaacg | 60 |
| cggtagaacg | tacttatcac | ctacagtttt | attttgtttt | tctttttggt | ttaatctatc | 120 |
| cagcttagta | ccgagtgggg | gaaagtgact | ggtgtgccta | aaaccttttc | tttgatactt | 180 |
| tgtaaaaata | catacagata | caatggcgaa | cggtaacttc | aagttgtctc | aattgctcaa | 240 |
| tgtggacgag | atgtctgctg | agcagaggag | tcatttcttt | gacttgatgc | tgactaaacc | 300 |
| tgattgtgag | atcgggcaaa | tgatgcaaag | agttgttgtt | gataaagtcg | atgacatgat | 360 |
| tagagaaaga | aagactaaag | atccagtgat | tgttcatgaa | gttctttctc | agaaggaaca | 420 |
| gaacaagttg | atggaaattt | atcctgaatt | caatatcgtg | tttaaagacg | acaaaaacat | 480 |
| ggttcatggg | tttgcggctg | ctgagcgaaa | actacaagct | ttattgcttt | tagatagagt | 540 |
| tcctgctctg | caagaggtgg | atgacatcgg | tggtcaatgg | tcgttttggg | taactagagg | 600 |
| tgagaaaagg | attcattcct | gttgtccaaa | tctagatatt | cgggatgatc | agagagaaat | 660 |
| ttctcgacag | atatttctta | ctgctattgg | tgatcaagct | agaagtggta | agagacagat | 720 |

```
gtcggagaat gagctgtgga tgtatgacca atttcgtgaa aatattgctg cgcctaacgc    780
ggttaggtgc aataatacat atcagggttg tacatgtagg ggttttctg atggtaagaa     840 gaaaggcgcg cagtatgcga tagctcttca cagcctgtat gacttcaagt tgaaagactt    900
gatggctact atggttgaga agaaaactaa agtggttcat gctgctatgc tttttgctcc    960
tgaaagtatg ttagtggacg aaggtccatt accttctgtt gacggttact acatgaagaa   1020
gaacgggaag atctatttcg ttttgagaa agatccttcc ttttcttaca ttcatgactg     1080
ggaagagtac aagaagtatc tactggggaa gccagtgagt taccaaggga atgtgttcta   1140
cttcgaaccg tggcaggtga gaggagacac aatgcttttt tcgatctaca ggatagctgg   1200
agttccgagg aggtctctat catcgcaaga gtactaccga agaatatata tcagtagatg   1260
ggaaaacatg gttgttgtcc aattttcga tctggtcgaa tcaacgcgag agttggtcaa    1320
gaaagacctg tttgtagaga acaattcat ggacaagtgt ttggattaca tagctaggtt    1380
atctgaccag cagctgacca taagcaatgt taaatcatac ttgagttcaa ataattgggt   1440
cttattcata aacggggcgg ccgtgaagaa caagcaaagt gtagattctc gagatttaca   1500
gttgttggct caaactttgc tagtgaagga acaagtggcg agacctgtca tgagggagtt   1560
gcgtgaagca attctgactg agacgaaacc tatcacgtca ttgactgatg tgctgggttt   1620
aatatcaaga aaactgtgga agcagtttgc taacaagatc gcagtcggcg gattcgttgg   1680
catggttggt actctaattg gattctatcc aaagaaggta ctaacctggg cgaaggacac   1740
accaaatggt ccagaactat gttacgagaa ctcgcacaaa accaaggtga tagtatttct   1800
gagtgttgtg tatgccattg gaggaatcac gcttatgcgt cgagacatcc gagatggact   1860
ggtgaaaaaa ctatgtgata tgtttgatat caaacggggg gcccatgtct tagacgttga   1920
gaatccgtgc cgctattatg aaatcaacga tttctttagc agtctgtatt cggcatctga   1980
gtccggtgag accgttttac cagatttatc cgaggtaaaa gccaagtctg ataagctatt   2040
gcagcagaag aaagaaatcg ctgacgagtt tctaagtgca aaattctcta actattctgg   2100
cagttcggtg agaacttctc caccatcggt ggtcggttca tctcgaagcg gactgggtct   2160
gttgttggaa gacagtaacg tgctgaccca agctagagtt ggagtttcaa gaaaggtaga   2220
cgatgaggag atcatggagc agtttctgag tggtcttatt gacactgaag cagaaattga   2280
cgaggttgtt ccagccttt cagctgaatg tgaaagaggg gaaacaagcg gtacaaaggt    2340
gttgtgtaaa cctttaacgc caccaggatt tgagaacgtg ttgccagctg tcaaaccttt   2400
ggtcagcaaa ggaaaaacgg tcaaacgtgt cgattacttc caagtgatgg gaggtgagag   2460
attaccaaaa aggccggttg tcagtggaga cgattctgtg gacgctagaa gagagtttct   2520
gtactactta gatgcggaga gagtcgctca aaatgatgaa attatgtctc tgtatcgtga   2580
ctattcgaga ggagttattc gaactggagg tcagaattac ccgcacggac tgggagtgtg   2640
ggatgtggaa atgaagaact ggtgcatacg tccagtggtc actgaacatg cttatgtgtt   2700
ccaaccagac aaacgtatgg atgattggtc gggatactta gaagtggctg tttgggaacg   2760
aggtatgttg gtcaacgact cgcggtcga aaggatgagt gattatgtca tagtttgcga    2820
tcagacgtat ctttgcaata acaggttgat cttggacaat ttaagtgccc tggatctagg   2880
accagttaac tgttcttttg aattagttga cggtgtacct ggttgtggta agtcgacaat   2940
gattgtcaac tcagctaatc cttgtgtcga tgtggttctc tctactggga gagcagcaac   3000
cgacgacttg atcgagagat tcgcgagcaa aggttttcca tgcaaattga aaggagagt    3060
```

```
gaagacggtt gattcttttt tgatgcattg tgttgatggt tctttaaccg gagacgtgtt      3120
gcatttcgat gaagctctca tggcccatgc tggtatggtg tacttttgcg ctcagatagc      3180
tggtgctaaa cgatgtatct gtcaaggaga tcagaatcaa atttctttca agcctagggt      3240
atctcaagtt gatttgaggt tttctagtct ggtcggaaag tttgacattg ttacagaaaa      3300
aagagaaact tacagaagtc cagcagatgt ggctgccgta ttgaacaagt actatactgg      3360
agatgtcaga acacataacg cgactgctaa ttcgatgacg gtgaggaaga ttgtgtctaa      3420
agaacaggtt tctttgaagc ctggtgctca gtacataact ttccttcagt ctgagaagaa      3480
ggagttggta aatttgttgg cattgaggaa agtggcagct aaagtgagta cagtacacga      3540
gtcgcaagga gagacattca aagatgtagt cctagtcagg acgaaaccta cggatgactc      3600
aatcgctaga ggtcgggagt acttaatcgt ggcgttgtcg cgtcacacac aatcacttgt      3660
gtatgaaact gtgaaagagg acgatgtaag caaagagatc agggaaagtg ccgcgcttac      3720
gaaggcggct ttggcaagat tttttgttac tgagaccgtc ttatgacggt ttcggtctag      3780
gtttgatgtc tttagacatc atgaagggcc ttgcgccgtt ccagattcag gtacgattac      3840
ggacttggag atgtggtacg acgctttgtt tccgggaaat tcgttaagag actcaagcct      3900
agacgggtat ttggtggcaa cgactgattg caatttgcga ttagacaatg ttacgatcaa      3960
aagtggaaac tggaaagaca gtttgctga aaagaaacg tttctgaaac cggttattcg      4020
tactgctatg cctgacaaaa ggaagactac tcagttggag agtttgttag cattgcagaa      4080
aaggaaccaa gcggcacccg atctacaaga aaatgtgcac gcaacagttc taatcgaaga      4140
gacgatgaag aagttgaaat ctgttgtcta cgatgtggga aaaattcggg ctgatcctat      4200
tgtcaataga gctcaaatgg agagatggtg gagaaatcaa agcacagcgg tacaggctaa      4260
ggtagtagca gatgtgagag agttacatga aatagactat tcgtcttaca tgtatatgat      4320
caaatctgac gtgaaaccta agactgattt aacaccgcaa tttgaatact cagctctaca      4380
gactgttgtg tatcacgaga agttgatcaa ctcgttgttc ggtccaattt tcaaagaaat      4440
taatgaacgc aagttggatg ctatgcaacc acattttgtg ttcaacacga gaatgacatc      4500
gagtgattta aacgatcgag tgaagttctt aaatacggaa gcggcttacg actttgttga      4560
gatagacatg tctaaattcg acaagtcggc aaatcgcttc catttacaac tgcagctgga      4620
gatttacagg ttatttgggc tagatgagtg ggcggccttc cttttgggag tgtcgcacac      4680
tcaaactact gtgagagata ttcaaaatgg tatgatggcg catatttggt accaacaaaa      4740
gagtggagat gctgatactt ataatgcaaa ttcagataga acactgtgtg cactcttgtc      4800
tgaattacca tttggagaaag cagtcatggt tacatatgga ggagatgact cactgattgc      4860
gtttcctaga ggaacgcagt tgttgatcc gtgtccaaag ttggctacta agtggaattt      4920
cgagtgcaag attttaagt acgatgtccc aatgttttgt gggaagttct tgcttaagac      4980
gtcatcgtgt tacgagttcg tgccagatcc ggtaaaagtt ctgacgaagt tggggaaaaa      5040
gagtataaag gatgtgcaac atttagccga gatctacatc tcgctgaatg attccaatag      5100
agctcttggg aactacatgg tggtatccaa actgtccgag tctgtttcag accggtattt      5160
gtacaaaggt gattctgttc atgcgctttg tgcgctatgg aagcatatta agagttttac      5220
agctctgtgt acattattcc gagacgaaaa cgataaggaa ttgaacccgg ctaaggttga      5280
ttggaagaag gcacagagag ctgtgtcaaa cttttacgac tggtaatatg gaagacaagt      5340
cattggtcac cttgaagaag aagactttcg aagtctcaaa attctcaaat ctaggggcca      5400
ttgaattgtt tgtggacggt aggaggaaga gaccgaagta ttttcacaga agaagagaaa      5460
```

```
ctgtcctaaa tcatgttggt gggaagaaga gtgaacacaa gttagacgtt tttgaccaaa    5520
gggattacaa aatgattaaa tcttacgcgt ttctaaagat agtaggtgta caactagttg    5580
taacatcaca tctacctgca gatacgcctg ggttcattca aatcgatctg ttggattcga    5640
gacttactga gaaaagaaag agaggaaaga ctattcagag attcaaagct cgagcttgcg    5700
ataactgttc agttgcgcag tacaaggttg aatacagtat ttccacacag gagaacgtac    5760
ttgatgtctg gaaggtgggt tgtatttctg agggcgttcc ggtctgtgac ggtacatacc    5820 cttttcagtat cgaagtgtcg ctaatatggg ttgctactga ttcgactagg cgcctcaatg    5880
tggaagaact gaacagttcg gattacattg aaggcgattt taccgatcaa gaggttttcg    5940
gtgagttcat gtcttttgaaa caagtggaga tgaagacgat tgaggcgaag tacgatggtc    6000
cttacagacc agctactact agacctaagt cattattgtc aagtgaagat gttaagagag    6060
cgtctaataa gaaaaactcg tcttaatgca taaagaaatt tattgtcaat atgacgtgtg    6120
tactcaaggg ttgtgtgaat gaagtcactg ttccttggtca cgagacgtgt agtatcggtc    6180
atgctaacaa attgcgaaag caagttgctg acatggttgg tgtcacacgt aggtgtgcgg    6240
aaaataattg tggatggttt gtctgtgttg ttatcaatga ttttacttttt gatgtgtata    6300 attgttgtgg ccgtagtcac cttgaaaagt gtcgtaaacg tgttgaaaca agaaatcgag    6360
aaatttggaa acaaattcga cgaaatcaag ctgaaaacat gtctgcgaca gctaaaaagt    6420
ctcataattc gaagacctct aagaagaaat tcaaagagga cagagaattt gggacaccaa    6480
aaagattttt aagagatgat gttcctttcg ggattgatcg tttgtttgct ttttgatttt    6540
attttatatt gttatctgtt tctgtgtata gactgtttga gattggcgct tggccgactc    6600
attgtcttac cataggggaa cggactttgt ttgtgttgtt attttatttg tattttatta    6660
aaattctcaa tgatctgaaa aggcctcgag gctaagagat tattgggggg tgagtaagta    6720
cttttaaagt gatgatggtt acaaaggcaa aagggtaaa accctcgcc tacgtaagcg      6780 ttattacgcc c                                                        6791
```

<210> SEQ ID NO 10
<211> LENGTH: 23
<212> TYPE: DNA
<213> ORGANISM: Artificial sequence
<220> FEATURE:
<223> OTHER INFORMATION: Cas9-gw-Fw

<400> SEQUENCE: 10

```
caccatggac tataaggacc acg                                             23
```

<210> SEQ ID NO 11
<211> LENGTH: 23
<212> TYPE: DNA
<213> ORGANISM: Artificial sequence
<220> FEATURE:
<223> OTHER INFORMATION: Cas9-Rev-Stop

<400> SEQUENCE: 11

```
ttacttttc ttttttgcct ggc                                              23
```

<210> SEQ ID NO 12
<211> LENGTH: 20
<212> TYPE: DNA
<213> ORGANISM: Artificial sequence
<220> FEATURE:
<223> OTHER INFORMATION: Cas9-Rev-No-Stop

```
<400> SEQUENCE: 12 cttttttcttt tttgcctggc                                              20

<210> SEQ ID NO 13
<211> LENGTH: 22
<212> TYPE: DNA
<213> ORGANISM: Artificial sequence
<220> FEATURE:
<223> OTHER INFORMATION: NB-ACTIN1-RT-F

<400> SEQUENCE: 13
tgaagatcct cacagagcgt gg                                            22

<210> SEQ ID NO 14
<211> LENGTH: 22
<212> TYPE: DNA
<213> ORGANISM: Artificial sequence
<220> FEATURE:
<223> OTHER INFORMATION: NB-ACTIN1QRT-LIU-R

<400> SEQUENCE: 14
ttgtatgtgg tctcgtggat tc                                            22

<210> SEQ ID NO 15
<211> LENGTH: 22
<212> TYPE: DNA
<213> ORGANISM: Artificial sequence
<220> FEATURE:
<223> OTHER INFORMATION: CAS9-SEQ-F6

<400> SEQUENCE: 15
gccctccaaa tatgtgactt cc                                            22

<210> SEQ ID NO 16
<211> LENGTH: 23
<212> TYPE: DNA
<213> ORGANISM: Artificial sequence
<220> FEATURE:
<223> OTHER INFORMATION: CAS9-REV-STOP

<400> SEQUENCE: 16 ttacttttc ttttttgcct ggc                                            23

<210> SEQ ID NO 17
<211> LENGTH: 20
<212> TYPE: DNA
<213> ORGANISM: Artificial sequence
<220> FEATURE:
<223> OTHER INFORMATION: TRV1-RELICASE-RT-F

<400> SEQUENCE: 17
ctactgggag agcagcaacc                                               20

<210> SEQ ID NO 18
<211> LENGTH: 20
<212> TYPE: DNA
<213> ORGANISM: Artificial sequence
<220> FEATURE:
<223> OTHER INFORMATION: TRV1-REPLICASE-RT-R

<400> SEQUENCE: 18
ctgagcgcaa aagtacacca                                               20

<210> SEQ ID NO 19
<211> LENGTH: 30
```

```
<212> TYPE: DNA
<213> ORGANISM: Artificial sequence
<220> FEATURE:
<223> OTHER INFORMATION: SPDK-PEBVS/SEQF

<400> SEQUENCE: 19
cgaattcgag catcttgttc tggggtttca                              30

<210> SEQ ID NO 20
<211> LENGTH: 30
<212> TYPE: DNA
<213> ORGANISM: Artificial sequence
<220> FEATURE:
<223> OTHER INFORMATION: SPDK-SEQ-R

<400> SEQUENCE: 20
ctatggtaag acaatgagtc ggccaaacgc                              30

<210> SEQ ID NO 21
<211> LENGTH: 20
<212> TYPE: DNA
<213> ORGANISM: Artificial sequence
<220> FEATURE:
<223> OTHER INFORMATION: NB-PDS3-TR1,2-gDNA-F2

<400> SEQUENCE: 21
gaaacacatc acctaggcgg                                         20

<210> SEQ ID NO 22
<211> LENGTH: 20
<212> TYPE: DNA
<213> ORGANISM: Artificial sequence
<220> FEATURE:
<223> OTHER INFORMATION: NB-PDS3-TR1,2-gDNA-R

<400> SEQUENCE: 22
gggcgtgagg aagtacgaaa                                         20

<210> SEQ ID NO 23
<211> LENGTH: 25
<212> TYPE: DNA
<213> ORGANISM: Artificial sequence
<220> FEATURE:
<223> OTHER INFORMATION: NBPDS3-gDNA-404bp-F

<400> SEQUENCE: 23
gtaaaatgcc ccaaattgga cttgt                                   25

<210> SEQ ID NO 24
<211> LENGTH: 26
<212> TYPE: DNA
<213> ORGANISM: Artificial sequence
<220> FEATURE:
<223> OTHER INFORMATION: NBPDS3-gDNA-404bp-R

<400> SEQUENCE: 24
cgtgaggaag tacgaaatga tgatga                                  26

<210> SEQ ID NO 25
<211> LENGTH: 20
<212> TYPE: DNA
<213> ORGANISM: Artificial sequence
<220> FEATURE:
<223> OTHER INFORMATION: NB.PCNA gDNA F1

<400> SEQUENCE: 25
``` cctaaccccta atttccccag                                          20

<210> SEQ ID NO 26
<211> LENGTH: 20
<212> TYPE: DNA
<213> ORGANISM: Artificial sequence
<220> FEATURE:
<223> OTHER INFORMATION: NB.PCNA gDNA R1

<400> SEQUENCE: 26
tcactgtcaa tgtccatcag                                           20

<210> SEQ ID NO 27
<211> LENGTH: 25
<212> TYPE: DNA
<213> ORGANISM: Artificial sequence
<220> FEATURE:
<223> OTHER INFORMATION: 307528-16-F

<400> SEQUENCE: 27
aaattggatc ttggatcact caagc                                     25

<210> SEQ ID NO 28
<211> LENGTH: 25
<212> TYPE: DNA
<213> ORGANISM: Artificial sequence
<220> FEATURE:
<223> OTHER INFORMATION: 307528-16-R

<400> SEQUENCE: 28
agccgttgat ttctcattat ccaaa                                     25

<210> SEQ ID NO 29
<211> LENGTH: 25
<212> TYPE: DNA
<213> ORGANISM: Artificial sequence
<220> FEATURE:
<223> OTHER INFORMATION: 3623076-16-F

<400> SEQUENCE: 29
acagatcata tgggtgtgtc ttcga                                     25

<210> SEQ ID NO 30
<211> LENGTH: 25
<212> TYPE: DNA
<213> ORGANISM: Artificial sequence
<220> FEATURE:
<223> OTHER INFORMATION: 3623076-16-R

<400> SEQUENCE: 30
gatgaaggaa gcagtatccc tagca                                     25

<210> SEQ ID NO 31
<211> LENGTH: 25
<212> TYPE: DNA
<213> ORGANISM: Artificial sequence
<220> FEATURE:
<223> OTHER INFORMATION: 3623321-16-F

<400> SEQUENCE: 31
cgcgtaaaga taaagtgagc ggata                                     25

<210> SEQ ID NO 32
<211> LENGTH: 25
<212> TYPE: DNA
<213> ORGANISM: Artificial sequence

<220> FEATURE:
<223> OTHER INFORMATION: 3623321-16-R

<400> SEQUENCE: 32
ggagaatgga ggttgtgtca tcttt                                         25

<210> SEQ ID NO 33
<211> LENGTH: 25
<212> TYPE: DNA
<213> ORGANISM: Artificial sequence
<220> FEATURE:
<223> OTHER INFORMATION: 3472614-0-F

<400> SEQUENCE: 33
aattgcacaa tttgacatca aatgc                                         25

<210> SEQ ID NO 34
<211> LENGTH: 25
<212> TYPE: DNA
<213> ORGANISM: Artificial sequence
<220> FEATURE:
<223> OTHER INFORMATION: 3472614-0-R

<400> SEQUENCE: 34
gaaacacaag ctgacaagaa agcaa                                         25

<210> SEQ ID NO 35
<211> LENGTH: 25
<212> TYPE: DNA
<213> ORGANISM: Artificial sequence
<220> FEATURE:
<223> OTHER INFORMATION: 2306460-16-F

<400> SEQUENCE: 35
ctttggcttt ggagatccag tagaa                                         25

<210> SEQ ID NO 36
<211> LENGTH: 25
<212> TYPE: DNA
<213> ORGANISM: Artificial sequence
<220> FEATURE:
<223> OTHER INFORMATION: 2306460-16-R

<400> SEQUENCE: 36
tggaggtagc agtaatcgcc atatt                                         25

<210> SEQ ID NO 37
<211> LENGTH: 25
<212> TYPE: DNA
<213> ORGANISM: Artificial sequence
<220> FEATURE:
<223> OTHER INFORMATION: 3483953-0-F

<400> SEQUENCE: 37
tgaacattgg aatgctcttc atcat                                         25

<210> SEQ ID NO 38
<211> LENGTH: 25
<212> TYPE: DNA
<213> ORGANISM: Artificial sequence
<220> FEATURE:
<223> OTHER INFORMATION: 3483953-0-R

<400> SEQUENCE: 38
ctatacttcc tcaatccctg ggctt                                         25

```
<210> SEQ ID NO 39
<211> LENGTH: 25
<212> TYPE: DNA
<213> ORGANISM: Artificial sequence
<220> FEATURE:
<223> OTHER INFORMATION: 2815907-16-F

<400> SEQUENCE: 39
aggaccattt ccctatgcct tgtat                                25

<210> SEQ ID NO 40
<211> LENGTH: 25
<212> TYPE: DNA
<213> ORGANISM: Artificial sequence
<220> FEATURE:
<223> OTHER INFORMATION: 2815907-16-R

<400> SEQUENCE: 40
ggcgacatat tagttcgaat ggaag                                25

<210> SEQ ID NO 41
<211> LENGTH: 25
<212> TYPE: DNA
<213> ORGANISM: Artificial sequence
<220> FEATURE:
<223> OTHER INFORMATION: 236396-16-F

<400> SEQUENCE: 41
tttcatgtca tttggaggtg atttg                                25

<210> SEQ ID NO 42
<211> LENGTH: 25
<212> TYPE: DNA
<213> ORGANISM: Artificial sequence
<220> FEATURE:
<223> OTHER INFORMATION: 236396-16-R

<400> SEQUENCE: 42
accttaatga agtcccttga ttccc                                25

<210> SEQ ID NO 43
<211> LENGTH: 25
<212> TYPE: DNA
<213> ORGANISM: Artificial sequence
<220> FEATURE:
<223> OTHER INFORMATION: 1395749-16-F

<400> SEQUENCE: 43
aggacttgac atgaaagccc aatta                                25

<210> SEQ ID NO 44
<211> LENGTH: 25
<212> TYPE: DNA
<213> ORGANISM: Artificial sequence
<220> FEATURE:
<223> OTHER INFORMATION: 1395749-16-R

<400> SEQUENCE: 44
actcaaacga cgtagtatca tgcca                                25

<210> SEQ ID NO 45
<211> LENGTH: 25
<212> TYPE: DNA
<213> ORGANISM: Artificial sequence
<220> FEATURE:
<223> OTHER INFORMATION: 3655214-0-F
```

```
<400> SEQUENCE: 45
agtatggtgt tgtgaaggag gcatt                                    25

<210> SEQ ID NO 46
<211> LENGTH: 25
<212> TYPE: DNA
<213> ORGANISM: Artificial sequence
<220> FEATURE:
<223> OTHER INFORMATION: 3655214-0-R

<400> SEQUENCE: 46
cttccaaaca gcgctctctt agaac                                    25

<210> SEQ ID NO 47
<211> LENGTH: 25
<212> TYPE: DNA
<213> ORGANISM: Artificial sequence
<220> FEATURE:
<223> OTHER INFORMATION: 649861-16-F

<400> SEQUENCE: 47
ataccctctc aaacacttcg tccag                                    25

<210> SEQ ID NO 48
<211> LENGTH: 25
<212> TYPE: DNA
<213> ORGANISM: Artificial sequence
<220> FEATURE:
<223> OTHER INFORMATION: 649861-16-R

<400> SEQUENCE: 48
agatttagtg gtgaccaggg catta                                    25

<210> SEQ ID NO 49
<211> LENGTH: 25
<212> TYPE: DNA
<213> ORGANISM: Artificial sequence
<220> FEATURE:
<223> OTHER INFORMATION: 977912-0-F

<400> SEQUENCE: 49
ctctcaaggt tggaggaact tgaaa                                    25

<210> SEQ ID NO 50
<211> LENGTH: 25
<212> TYPE: DNA
<213> ORGANISM: Artificial sequence
<220> FEATURE:
<223> OTHER INFORMATION: 977912-0-R

<400> SEQUENCE: 50
aaatgggttt cgccatcact aagta                                    25

<210> SEQ ID NO 51
<211> LENGTH: 25
<212> TYPE: DNA
<213> ORGANISM: Artificial sequence
<220> FEATURE:
<223> OTHER INFORMATION: 6771578-0-F

<400> SEQUENCE: 51
atgacataat cggaagcaac aacct                                    25

<210> SEQ ID NO 52
```

```
<211> LENGTH: 25
<212> TYPE: DNA
<213> ORGANISM: Artificial sequence
<220> FEATURE:
<223> OTHER INFORMATION: 6771578-0-R

<400> SEQUENCE: 52
gccttggttt ctacagttcg aaaga                                    25

<210> SEQ ID NO 53
<211> LENGTH: 25
<212> TYPE: DNA
<213> ORGANISM: Artificial sequence
<220> FEATURE:
<223> OTHER INFORMATION: 28210697-16-F

<400> SEQUENCE: 53
aataggctga accactctca ctgct                                    25

<210> SEQ ID NO 54
<211> LENGTH: 25
<212> TYPE: DNA
<213> ORGANISM: Artificial sequence
<220> FEATURE:
<223> OTHER INFORMATION: 28210697-16-R

<400> SEQUENCE: 54
tggaggctaa ttctaaagga aaggc                                    25

<210> SEQ ID NO 55
<211> LENGTH: 25
<212> TYPE: DNA
<213> ORGANISM: Artificial sequence
<220> FEATURE:
<223> OTHER INFORMATION: 9388034-16-F

<400> SEQUENCE: 55
aggacggctt ctaaggtgct tagtt                                    25

<210> SEQ ID NO 56
<211> LENGTH: 25
<212> TYPE: DNA
<213> ORGANISM: Artificial sequence
<220> FEATURE:
<223> OTHER INFORMATION: 9388034-16-R

<400> SEQUENCE: 56
tcaaggccta catagcctta tgctc                                    25

<210> SEQ ID NO 57
<211> LENGTH: 25
<212> TYPE: DNA
<213> ORGANISM: Artificial sequence
<220> FEATURE:
<223> OTHER INFORMATION: 9020645-16-F

<400> SEQUENCE: 57
acactttgga agaatttgca catca                                    25

<210> SEQ ID NO 58
<211> LENGTH: 25
<212> TYPE: DNA
<213> ORGANISM: Artificial sequence
<220> FEATURE:
<223> OTHER INFORMATION: 9020645-16-R

<400> SEQUENCE: 58
```
tcaactgtcg taatgcccaa catac                                        25

<210> SEQ ID NO 59
<211> LENGTH: 25
<212> TYPE: DNA
<213> ORGANISM: Artificial sequence
<220> FEATURE:
<223> OTHER INFORMATION: 25640405-0-F

<400> SEQUENCE: 59
ccggtaactt gggacaccat aataa                                        25

<210> SEQ ID NO 60
<211> LENGTH: 25
<212> TYPE: DNA
<213> ORGANISM: Artificial sequence
<220> FEATURE:
<223> OTHER INFORMATION: 25640405-0-R

<400> SEQUENCE: 60
ttggaaataa tcaggatttg gatgg                                        25

<210> SEQ ID NO 61
<211> LENGTH: 25
<212> TYPE: DNA
<213> ORGANISM: Artificial sequence
<220> FEATURE:
<223> OTHER INFORMATION: 11029229-0-F

<400> SEQUENCE: 61
atgaggcatc tacaccaatt gttca                                        25

<210> SEQ ID NO 62
<211> LENGTH: 25
<212> TYPE: DNA
<213> ORGANISM: Artificial sequence
<220> FEATURE:
<223> OTHER INFORMATION: 11029229-0-R

<400> SEQUENCE: 62
cttccttgtt tatcatgggt tcacc                                        25

<210> SEQ ID NO 63
<211> LENGTH: 25
<212> TYPE: DNA
<213> ORGANISM: Artificial sequence
<220> FEATURE:
<223> OTHER INFORMATION: 1668194-16-F

<400> SEQUENCE: 63
gtgctcctct gcttatggct tgtat                                        25

<210> SEQ ID NO 64
<211> LENGTH: 25
<212> TYPE: DNA
<213> ORGANISM: Artificial sequence
<220> FEATURE:
<223> OTHER INFORMATION: 1668194-16-R

<400> SEQUENCE: 64
gtaccggcat cttacaactt gcttt                                        25

<210> SEQ ID NO 65
<211> LENGTH: 25
<212> TYPE: DNA

```
<213> ORGANISM: Artificial sequence
<220> FEATURE:
<223> OTHER INFORMATION: 1313858-16-F

<400> SEQUENCE: 65
gtatgacgtc gataatgtgg cagag                                              25

<210> SEQ ID NO 66
<211> LENGTH: 25
<212> TYPE: DNA
<213> ORGANISM: Artificial sequence
<220> FEATURE:
<223> OTHER INFORMATION: 1313858-16-R

<400> SEQUENCE: 66
gaaccaatag cataacgaca agggt                                              25

<210> SEQ ID NO 67
<211> LENGTH: 25
<212> TYPE: DNA
<213> ORGANISM: Artificial sequence
<220> FEATURE:
<223> OTHER INFORMATION: 6884889-16-F

<400> SEQUENCE: 67
agttgcctct attgccttca ctttg                                              25

<210> SEQ ID NO 68
<211> LENGTH: 25
<212> TYPE: DNA
<213> ORGANISM: Artificial sequence
<220> FEATURE:
<223> OTHER INFORMATION: 6884889-16-R

<400> SEQUENCE: 68
gttctcactt cgaggaaagg catta                                              25

<210> SEQ ID NO 69
<211> LENGTH: 25
<212> TYPE: DNA
<213> ORGANISM: Artificial sequence
<220> FEATURE:
<223> OTHER INFORMATION: 9019907-0-F

<400> SEQUENCE: 69
atgatggtgt gatcaggaga tgtgt                                              25

<210> SEQ ID NO 70
<211> LENGTH: 25
<212> TYPE: DNA
<213> ORGANISM: Artificial sequence
<220> FEATURE:
<223> OTHER INFORMATION: 9019907-0-R

<400> SEQUENCE: 70
gaccaatcaa ttcaatttgc attga                                              25

<210> SEQ ID NO 71
<211> LENGTH: 25
<212> TYPE: DNA
<213> ORGANISM: Artificial sequence
<220> FEATURE:
<223> OTHER INFORMATION: 24706946-16-F

<400> SEQUENCE: 71
gtttggtgca ataagaactg aaccc                                              25
```

<210> SEQ ID NO 72
<211> LENGTH: 25
<212> TYPE: DNA
<213> ORGANISM: Artificial sequence
<220> FEATURE:
<223> OTHER INFORMATION: 24706946-16-R

<400> SEQUENCE: 72
aacatctcca acctcacttc tttcg                                    25

<210> SEQ ID NO 73
<211> LENGTH: 25
<212> TYPE: DNA
<213> ORGANISM: Artificial sequence
<220> FEATURE:
<223> OTHER INFORMATION: 8645480-0-F

<400> SEQUENCE: 73
tctccgagaa ctctcctgaa tcact                                    25

<210> SEQ ID NO 74
<211> LENGTH: 25
<212> TYPE: DNA
<213> ORGANISM: Artificial sequence
<220> FEATURE:
<223> OTHER INFORMATION: 8645480-0-R

<400> SEQUENCE: 74
tgtactacgt gaaacatgtt gggct                                    25

<210> SEQ ID NO 75
<211> LENGTH: 25
<212> TYPE: DNA
<213> ORGANISM: Artificial sequence
<220> FEATURE:
<223> OTHER INFORMATION: 12205859-0-F

<400> SEQUENCE: 75
ttaagtgctt gacataccag cctca                                    25

<210> SEQ ID NO 76
<211> LENGTH: 25
<212> TYPE: DNA
<213> ORGANISM: Artificial sequence
<220> FEATURE:
<223> OTHER INFORMATION: 12205859-0-R

<400> SEQUENCE: 76
gccttcttcc ttctcttcct caatt                                    25

<210> SEQ ID NO 77
<211> LENGTH: 25
<212> TYPE: DNA
<213> ORGANISM: Artificial sequence
<220> FEATURE:
<223> OTHER INFORMATION: 10568921-16-F

<400> SEQUENCE: 77
aacacttcga ttaaggacga ttgga                                    25

<210> SEQ ID NO 78
<211> LENGTH: 25
<212> TYPE: DNA
<213> ORGANISM: Artificial sequence
<220> FEATURE:

```
<223> OTHER INFORMATION: 10568921-16-R

<400> SEQUENCE: 78
aaacctggac cgttgatcaa ataga                                               25

<210> SEQ ID NO 79
<211> LENGTH: 25
<212> TYPE: DNA
<213> ORGANISM: Artificial sequence
<220> FEATURE:
<223> OTHER INFORMATION: 10857750-0-F

<400> SEQUENCE: 79
actgacaccg tctggtagaa ggact                                               25

<210> SEQ ID NO 80
<211> LENGTH: 25
<212> TYPE: DNA
<213> ORGANISM: Artificial sequence
<220> FEATURE:
<223> OTHER INFORMATION: 10857750-0-R

<400> SEQUENCE: 80
tgtccactcc tcaacgatat cacat                                               25

<210> SEQ ID NO 81
<211> LENGTH: 25
<212> TYPE: DNA
<213> ORGANISM: Artificial sequence
<220> FEATURE:
<223> OTHER INFORMATION: 1710512-16-F

<400> SEQUENCE: 81
agaaggccta gtgactctgc ttgaa                                               25

<210> SEQ ID NO 82
<211> LENGTH: 25
<212> TYPE: DNA
<213> ORGANISM: Artificial sequence
<220> FEATURE:
<223> OTHER INFORMATION: 1710512-16-R

<400> SEQUENCE: 82
ctcatctcga gcatcaacat catct                                               25

<210> SEQ ID NO 83
<211> LENGTH: 25
<212> TYPE: DNA
<213> ORGANISM: Artificial sequence
<220> FEATURE:
<223> OTHER INFORMATION: 599232-16-F

<400> SEQUENCE: 83
aatatctttg ttcctggtca gccaa                                               25

<210> SEQ ID NO 84
<211> LENGTH: 25
<212> TYPE: DNA
<213> ORGANISM: Artificial sequence
<220> FEATURE:
<223> OTHER INFORMATION: 599232-16-R

<400> SEQUENCE: 84
taaatgcatt tcaggctgga aactt                                               25
```

```
<210> SEQ ID NO 85
<211> LENGTH: 25
<212> TYPE: DNA
<213> ORGANISM: Artificial sequence
<220> FEATURE:
<223> OTHER INFORMATION: 2639758-0-F

<400> SEQUENCE: 85
tccatatttc tgattcgcgg actat                                         25

<210> SEQ ID NO 86
<211> LENGTH: 25
<212> TYPE: DNA
<213> ORGANISM: Artificial sequence
<220> FEATURE:
<223> OTHER INFORMATION: 2639758-0-R

<400> SEQUENCE: 86
tttgtaactt gtccgagcct ctttc                                         25

<210> SEQ ID NO 87
<211> LENGTH: 25
<212> TYPE: DNA
<213> ORGANISM: Artificial sequence
<220> FEATURE:
<223> OTHER INFORMATION: 161845497-16-F

<400> SEQUENCE: 87
ttgggattgt gatccgaata actct                                         25

<210> SEQ ID NO 88
<211> LENGTH: 25
<212> TYPE: DNA
<213> ORGANISM: Artificial sequence
<220> FEATURE:
<223> OTHER INFORMATION: 161845497-16-R

<400> SEQUENCE: 88
gcatattccg accgaatagt ctacg                                         25

<210> SEQ ID NO 89
<211> LENGTH: 25
<212> TYPE: DNA
<213> ORGANISM: Artificial sequence
<220> FEATURE:
<223> OTHER INFORMATION: 66367769-0-F

<400> SEQUENCE: 89
tatttggaat ccaagcccctt cagta                                        25

<210> SEQ ID NO 90
<211> LENGTH: 25
<212> TYPE: DNA
<213> ORGANISM: Artificial sequence
<220> FEATURE:
<223> OTHER INFORMATION: 66367769-0-R

<400> SEQUENCE: 90
tgaaggcatg catttcatta agttg                                         25

<210> SEQ ID NO 91
<211> LENGTH: 25
<212> TYPE: DNA
<213> ORGANISM: Artificial sequence
<220> FEATURE:
<223> OTHER INFORMATION: 60631893-16-F
```

```
<400> SEQUENCE: 91
gaagagttcg aagccagtca agaag                                          25

<210> SEQ ID NO 92
<211> LENGTH: 25
<212> TYPE: DNA
<213> ORGANISM: Artificial sequence
<220> FEATURE:
<223> OTHER INFORMATION: 60631893-16-R

<400> SEQUENCE: 92
tgacagacaa agatcatcac tgcag                                          25

<210> SEQ ID NO 93
<211> LENGTH: 25
<212> TYPE: DNA
<213> ORGANISM: Artificial sequence
<220> FEATURE:
<223> OTHER INFORMATION: 5303471-16-F

<400> SEQUENCE: 93
gctcataaac tcaccctaaa ggcaa                                          25

<210> SEQ ID NO 94
<211> LENGTH: 25
<212> TYPE: DNA
<213> ORGANISM: Artificial sequence
<220> FEATURE:
<223> OTHER INFORMATION: 5303471-16-R

<400> SEQUENCE: 94
acccttcggg aattggtatc actat                                          25

<210> SEQ ID NO 95
<211> LENGTH: 25
<212> TYPE: DNA
<213> ORGANISM: Artificial sequence
<220> FEATURE:
<223> OTHER INFORMATION: 23533037-16-F

<400> SEQUENCE: 95
acccagacta ggaaatgctt ctcct                                          25

<210> SEQ ID NO 96
<211> LENGTH: 25
<212> TYPE: DNA
<213> ORGANISM: Artificial sequence
<220> FEATURE:
<223> OTHER INFORMATION: 23533037-16-R

<400> SEQUENCE: 96
tcgcaaatca tattgcttaa gaaca                                          25

<210> SEQ ID NO 97
<211> LENGTH: 25
<212> TYPE: DNA
<213> ORGANISM: Artificial sequence
<220> FEATURE:
<223> OTHER INFORMATION: 13305716-0-F

<400> SEQUENCE: 97
ctcgtactcg gcttcgttgt tagtt                                          25

<210> SEQ ID NO 98
<211> LENGTH: 25
```

```
<212> TYPE: DNA
<213> ORGANISM: Artificial sequence
<220> FEATURE:
<223> OTHER INFORMATION: 13305716-0-R

<400> SEQUENCE: 98
ctctctctag gttcatctcg cgatc                                              25

<210> SEQ ID NO 99
<211> LENGTH: 25
<212> TYPE: DNA
<213> ORGANISM: Artificial sequence
<220> FEATURE:
<223> OTHER INFORMATION: 110292002-16-F

<400> SEQUENCE: 99
catggtttgc tgatgtttcc aatta                                              25

<210> SEQ ID NO 100
<211> LENGTH: 25
<212> TYPE: DNA
<213> ORGANISM: Artificial sequence
<220> FEATURE:
<223> OTHER INFORMATION: 110292002-16-R

<400> SEQUENCE: 100
gctctaactc gaccgtaaga tggaa                                              25

<210> SEQ ID NO 101
<211> LENGTH: 25
<212> TYPE: DNA
<213> ORGANISM: Artificial sequence
<220> FEATURE:
<223> OTHER INFORMATION: 58328972-0-F

<400> SEQUENCE: 101
taacatagac acgtgaaaca tcggg                                              25

<210> SEQ ID NO 102
<211> LENGTH: 25
<212> TYPE: DNA
<213> ORGANISM: Artificial sequence
<220> FEATURE:
<223> OTHER INFORMATION: 58328972-0-R

<400> SEQUENCE: 102
tctttgacat ggtcagactg ctttc                                              25

<210> SEQ ID NO 103
<211> LENGTH: 25
<212> TYPE: DNA
<213> ORGANISM: Artificial sequence
<220> FEATURE:
<223> OTHER INFORMATION: 109561616-16-F

<400> SEQUENCE: 103
cctagaatgc ggtggatcag attac                                              25

<210> SEQ ID NO 104
<211> LENGTH: 25
<212> TYPE: DNA
<213> ORGANISM: Artificial sequence
<220> FEATURE:
<223> OTHER INFORMATION: 109561616-16-R

<400> SEQUENCE: 104
```
accaacatta tcatggtcaa ggaca                                          25

<210> SEQ ID NO 105
<211> LENGTH: 25
<212> TYPE: DNA
<213> ORGANISM: Artificial sequence
<220> FEATURE:
<223> OTHER INFORMATION: 118708061-0-F

<400> SEQUENCE: 105
attctagctg aacttgcaga ggatg                                          25

<210> SEQ ID NO 106
<211> LENGTH: 25
<212> TYPE: DNA
<213> ORGANISM: Artificial sequence
<220> FEATURE:
<223> OTHER INFORMATION: 118708061-0-R

<400> SEQUENCE: 106
tataaacgtt tgtctcaaca gtccc                                          25

<210> SEQ ID NO 107
<211> LENGTH: 25
<212> TYPE: DNA
<213> ORGANISM: Artificial sequence
<220> FEATURE:
<223> OTHER INFORMATION: 2542427-16-F

<400> SEQUENCE: 107
atgtttggca acgagaaaga atctc                                          25

<210> SEQ ID NO 108
<211> LENGTH: 25
<212> TYPE: DNA
<213> ORGANISM: Artificial sequence
<220> FEATURE:
<223> OTHER INFORMATION: 2542427-16-R

<400> SEQUENCE: 108
acataatcag atcagtggtc gtgga                                          25

<210> SEQ ID NO 109
<211> LENGTH: 25
<212> TYPE: DNA
<213> ORGANISM: Artificial sequence
<220> FEATURE:
<223> OTHER INFORMATION: 73089692-16-F

<400> SEQUENCE: 109
ccacatttag gaatgatgcg acata                                          25

<210> SEQ ID NO 110
<211> LENGTH: 25
<212> TYPE: DNA
<213> ORGANISM: Artificial sequence
<220> FEATURE:
<223> OTHER INFORMATION: 73089692-16-R

<400> SEQUENCE: 110
tctgctctcc ttatcgttcg agtct                                          25

<210> SEQ ID NO 111
<211> LENGTH: 25
<212> TYPE: DNA
<213> ORGANISM: Artificial sequence

```
<220> FEATURE:
<223> OTHER INFORMATION: 7004096-16-F

<400> SEQUENCE: 111
gaatggaagg gaaatagtgt tgtgc                                          25

<210> SEQ ID NO 112
<211> LENGTH: 25
<212> TYPE: DNA
<213> ORGANISM: Artificial sequence
<220> FEATURE:
<223> OTHER INFORMATION: 7004096-16-R

<400> SEQUENCE: 112
gatcctccct attccgcgaa tatac                                          25

<210> SEQ ID NO 113
<211> LENGTH: 25
<212> TYPE: DNA
<213> ORGANISM: Artificial sequence
<220> FEATURE:
<223> OTHER INFORMATION: 18989987-16-F

<400> SEQUENCE: 113
tcgataagtc tgataccgac ggttt                                          25

<210> SEQ ID NO 114
<211> LENGTH: 25
<212> TYPE: DNA
<213> ORGANISM: Artificial sequence
<220> FEATURE:
<223> OTHER INFORMATION: 18989987-16-R

<400> SEQUENCE: 114
tcacttactg cttcattgat ggagg                                          25

<210> SEQ ID NO 115
<211> LENGTH: 25
<212> TYPE: DNA
<213> ORGANISM: Artificial sequence
<220> FEATURE:
<223> OTHER INFORMATION: 59347010-16-F

<400> SEQUENCE: 115
agtatattca attgcgctca ctggg                                          25

<210> SEQ ID NO 116
<211> LENGTH: 25
<212> TYPE: DNA
<213> ORGANISM: Artificial sequence
<220> FEATURE:
<223> OTHER INFORMATION: 59347010-16-R

<400> SEQUENCE: 116
gtgctatgtt gagctgagac atgct                                          25

<210> SEQ ID NO 117
<211> LENGTH: 25
<212> TYPE: DNA
<213> ORGANISM: Artificial sequence
<220> FEATURE:
<223> OTHER INFORMATION: 19927971-16-F

<400> SEQUENCE: 117
agatgaagca tttgacatgt gcatt                                          25
```

<210> SEQ ID NO 118
<211> LENGTH: 25
<212> TYPE: DNA
<213> ORGANISM: Artificial sequence
<220> FEATURE:
<223> OTHER INFORMATION: 19927971-16-R

<400> SEQUENCE: 118
tggaagaact tgttccatca catgt                                        25

<210> SEQ ID NO 119
<211> LENGTH: 25
<212> TYPE: DNA
<213> ORGANISM: Artificial sequence
<220> FEATURE:
<223> OTHER INFORMATION: 61274140-0-F

<400> SEQUENCE: 119
gacttgacaa gtgggaccca ttaac                                        25

<210> SEQ ID NO 120
<211> LENGTH: 25
<212> TYPE: DNA
<213> ORGANISM: Artificial sequence
<220> FEATURE:
<223> OTHER INFORMATION: 61274140-0-R

<400> SEQUENCE: 120
atttgacgtg gatcagttgc aagta                                        25

<210> SEQ ID NO 121
<211> LENGTH: 25
<212> TYPE: DNA
<213> ORGANISM: Artificial sequence
<220> FEATURE:
<223> OTHER INFORMATION: 2246445-16-F

<400> SEQUENCE: 121
ctacagggac ctgaacaaag caagt                                        25

<210> SEQ ID NO 122
<211> LENGTH: 25
<212> TYPE: DNA
<213> ORGANISM: Artificial sequence
<220> FEATURE:
<223> OTHER INFORMATION: 2246445-16-R

<400> SEQUENCE: 122
caacttaaat atgagctcgc acgtg                                        25

<210> SEQ ID NO 123
<211> LENGTH: 49
<212> TYPE: DNA
<213> ORGANISM: Artificial sequence
<220> FEATURE:
<223> OTHER INFORMATION: Pds3

<400> SEQUENCE: 123
gttatgtttt ggtagtagcg actccatggg gcataagttt agaattcgt              49

<210> SEQ ID NO 124
<211> LENGTH: 42
<212> TYPE: DNA
<213> ORGANISM: Artificial sequence
<220> FEATURE:
<223> OTHER INFORMATION: 08_B11

-continued

<400> SEQUENCE: 124
gttatgtttt ggtagtagct ggggcataag tttagaattc gt                42

<210> SEQ ID NO 125
<211> LENGTH: 43
<212> TYPE: DNA
<213> ORGANISM: Artificial sequence
<220> FEATURE:
<223> OTHER INFORMATION: 10_D11

<400> SEQUENCE: 125
gttatgtttt ggtagtagca tgggcataa gtttagaatt cgt                43

<210> SEQ ID NO 126
<211> LENGTH: 45
<212> TYPE: DNA
<213> ORGANISM: Artificial sequence
<220> FEATURE:
<223> OTHER INFORMATION: 12_F11

<400> SEQUENCE: 126
gttatgtttt ggtagtagcg aatggggcat aagtttagaa ttcgt              45

<210> SEQ ID NO 127
<211> LENGTH: 46
<212> TYPE: DNA
<213> ORGANISM: Artificial sequence
<220> FEATURE:
<223> OTHER INFORMATION: 19_E12

<400> SEQUENCE: 127
gttatgtttt ggtagtagcg acatggggca taagtttaga attcgt             46

<210> SEQ ID NO 128
<211> LENGTH: 48
<212> TYPE: DNA
<213> ORGANISM: Artificial sequence
<220> FEATURE:
<223> OTHER INFORMATION: 22_H12

<400> SEQUENCE: 128
gttatgtttt ggtagtagcg actcatgggg cataagttta gaattcgt           48

<210> SEQ ID NO 129
<211> LENGTH: 50
<212> TYPE: DNA
<213> ORGANISM: Artificial sequence
<220> FEATURE:
<223> OTHER INFORMATION: 11_E11

<400> SEQUENCE: 129
gttatgtttt ggtagtagcg actccaatgg ggcataagtt tagaattcgt         50

<210> SEQ ID NO 130
<211> LENGTH: 39
<212> TYPE: DNA
<213> ORGANISM: Artificial sequence
<220> FEATURE:
<223> OTHER INFORMATION: 12_D06

<400> SEQUENCE: 130
gttatgtttt ggtagtaggg gcataagttt agaattcgt                     39

<210> SEQ ID NO 131

```
<211> LENGTH: 42
<212> TYPE: DNA
<213> ORGANISM: Artificial sequence
<220> FEATURE:
<223> OTHER INFORMATION: 08_H05

<400> SEQUENCE: 131
gttatgtttt ggtagtagcg acggcataag tttagaattc gt                        42

<210> SEQ ID NO 132
<211> LENGTH: 45
<212> TYPE: DNA
<213> ORGANISM: Artificial sequence
<220> FEATURE:
<223> OTHER INFORMATION: 10_B06

<400> SEQUENCE: 132
gttatgtttt ggtagtagcg aatggggcat aagtttagaa ttcgt                     45

<210> SEQ ID NO 133
<211> LENGTH: 46
<212> TYPE: DNA
<213> ORGANISM: Artificial sequence
<220> FEATURE:
<223> OTHER INFORMATION: 09_A06

<400> SEQUENCE: 133
gttatgtttt ggtagtagcg acatggggca taagtttaga attcgt                    46

<210> SEQ ID NO 134
<211> LENGTH: 48
<212> TYPE: DNA
<213> ORGANISM: Artificial sequence
<220> FEATURE:
<223> OTHER INFORMATION: 30_F08

<400> SEQUENCE: 134
gttatgtttt ggtagtagcg actcctgggg cataagttta gaattcgt                  48

<210> SEQ ID NO 135
<211> LENGTH: 48
<212> TYPE: DNA
<213> ORGANISM: Artificial sequence
<220> FEATURE:
<223> OTHER INFORMATION: 05_E05

<400> SEQUENCE: 135
gttatgtttt ggtagtagcg actcatgggg cataagttta gaattcgt                  48

<210> SEQ ID NO 136
<211> LENGTH: 50
<212> TYPE: DNA
<213> ORGANISM: Artificial sequence
<220> FEATURE:
<223> OTHER INFORMATION: 20_D07

<400> SEQUENCE: 136
gttatgtttt ggtagtagcg actccaatgg ggcataagtt tagaattcgt                50

<210> SEQ ID NO 137
<211> LENGTH: 52
<212> TYPE: DNA
<213> ORGANISM: Artificial sequence
<220> FEATURE:
<223> OTHER INFORMATION: pcna

<400> SEQUENCE: 137
```
tgagcactat cgttgtgacc gtaatatttc aatggggatg aaccttggta ac         52

<210> SEQ ID NO 138
<211> LENGTH: 40
<212> TYPE: DNA
<213> ORGANISM: Artificial sequence
<220> FEATURE:
<223> OTHER INFORMATION: 23 G11

<400> SEQUENCE: 138
tgagcactat cgttgtgacc gtgggatgaa ccttggtaac                       40

<210> SEQ ID NO 139
<211> LENGTH: 46
<212> TYPE: DNA
<213> ORGANISM: Artificial sequence
<220> FEATURE:
<223> OTHER INFORMATION: 15 G10

<400> SEQUENCE: 139
tgagcactat cgttgtgacc gtaaaatggg gatgaaccttt ggtaac               46

<210> SEQ ID NO 140
<211> LENGTH: 52
<212> TYPE: DNA
<213> ORGANISM: Artificial sequence
<220> FEATURE:
<223> OTHER INFORMATION: 05 H03

<400> SEQUENCE: 140
tgagcactat cgttgtgacc gcaatatttc aatggggatg aaccttggta ac         52

<210> SEQ ID NO 141
<211> LENGTH: 53
<212> TYPE: DNA
<213> ORGANISM: Artificial sequence
<220> FEATURE:
<223> OTHER INFORMATION: 26 F07

<400> SEQUENCE: 141
tgagcactat cgttgtgacc gtaatatttc aaatgggat gaaccttggt aac         53

<210> SEQ ID NO 142
<211> LENGTH: 58
<212> TYPE: DNA
<213> ORGANISM: Artificial sequence
<220> FEATURE:
<223> OTHER INFORMATION: WT

<400> SEQUENCE: 142
agtaacataa agttatgtac ctattgccga ggagcttgtg gagacgaata atgaggtc   58

<210> SEQ ID NO 143
<211> LENGTH: 57
<212> TYPE: DNA
<213> ORGANISM: Artificial sequence
<220> FEATURE:
<223> OTHER INFORMATION: H02

<400> SEQUENCE: 143
agtaacataa agttatgtac ctattgccga ggagttgtgg agacgaataa tgaggtc    57

<210> SEQ ID NO 144
<211> LENGTH: 55
<212> TYPE: DNA

```
<213> ORGANISM: Artificial sequence
<220> FEATURE:
<223> OTHER INFORMATION: E01

<400> SEQUENCE: 144
agtaacataa agttatgtac ctattgccga ggttgtggag acgaataatg aggtc            55

<210> SEQ ID NO 145
<211> LENGTH: 51
<212> TYPE: DNA
<213> ORGANISM: Artificial sequence
<220> FEATURE:
<223> OTHER INFORMATION: D05

<400> SEQUENCE: 145
agtaacataa agttatgtac ctattgccga gtggagacga ataatgaggt c                51

<210> SEQ ID NO 146
<211> LENGTH: 49
<212> TYPE: DNA
<213> ORGANISM: Artificial sequence
<220> FEATURE:
<223> OTHER INFORMATION: D03

<400> SEQUENCE: 146
agtaacataa agttatgtac ctattgccga ggagacgaat aatgaggtc                   49

<210> SEQ ID NO 147
<211> LENGTH: 59
<212> TYPE: DNA
<213> ORGANISM: Artificial sequence
<220> FEATURE:
<223> OTHER INFORMATION: G02

<400> SEQUENCE: 147
agtaacataa agttatgtac ctattgccga ggagccttgt ggagacgaat aatgaggtc        59
```

TARGETED VIRAL-MEDIATED PLANT GENOME EDITING USING CRISPR /CAS9

CROSS REFERENCE TO RELATED APPLICATIONS

This application is the National Stage of International Application No. PCT/IB2015/001202, filed 12 Jun. 2015, which claims the benefit of and priority to U.S. Provisional Patent Application Ser. No. 62/011,124 filed on 12 Jun. 2014 and titled "TARGETED VIRAL-MEDIATED PLANT GENOME EDITING USING CRISPR/CAS9" and U.S. Provisional Patent Application Ser. No. 62/014,309 filed on 19 Jun. 2014 and titled "TARGETED VIRAL-MEDIATED PLANT GENOME EDITING USING CRISPR/CAS9" the entire disclosures of which are herein incorporated by reference in their entireties.

FIELD OF THE DISCLOSURE

The present disclosure relates to methods of generating targeted mutations in a plant genome by delivering a guide polynucleotide to a plant cell expressing Cas9 endonuclease.

SEQUENCE LISTING

The present application includes a sequence listing incorporated herein by reference in its entirety. The information recorded in computer readable form on the electronic version referenced herein is identical to the written sequence listing published with the referenced PCT application.

BACKGROUND

Targeted plant genome editing will enable functional genetic and genomic studies, as well as help to discover, expand, and develop novel traits of agricultural importance for feed and fodder (Pennisi, E. (2010) *Science* 327: 802-803). Owing to the inefficiencies of the homology-directed repair process in plant cells, current research aimed at targeted genetic modification in plants is focused on generating targeted double-strand breaks (DSBs) and harnessing the two main DSB repair pathways: imprecise non-homologous end-joining and precise homology-directed repair (Voytas, D. F. (2013) *Ann. Rev. Plant Biol.* 64: 327-350). Enzymes that can be easily modified to bind specifically to user-selected genomic sequences and create DSBs do not exist in nature, but can be generated de novo as synthetic bimodular proteins containing a DNA-binding module engineered to bind a user-defined sequence along with a DNA-cleaving module capable of making DSBs in the genome. Several types of DNA-binding domains have been engineered to confer sequence specificity, including homing endonucleases, zinc finger nucleases (ZFNs), and transcription activator-like proteins. Customization of these genome-editing platforms requires protein engineering, a time-consuming and labor-intensive process (Puchta et al., (2014) *Plant J.* 78: 727-741). Furthermore, delivery of genome-engineering reagents into cells is a major barrier to the effective use of these technologies in discovering or designing novel traits (Baltes et al., (2014) *Plant Cell* 26: 151-163).

The recently developed CRISPR/Cas9 system has been used across eukaryotic species for targeted genome editing (Cong et al., (2013) *Science* 339: 819-823; Mali et al., (2013) *Science* 339, 823-826). This system comprises the Cas9 endonuclease of *Streptococcus pyogenes* and a synthetic guide RNA (gRNA) molecule that combines the functions of CRISPR RNA (cRNA) and transactivating cRNA (tracrRNA). The gRNA directs the Cas9 endonuclease to a target sequence complementary to 20 nucleotides preceding a protospacer-associated motif (PAM) NGG sequence required for Cas9 activity (Jinek et al., (2012) *Science* 337: 816-821). Owing to the specificity of the system and the fact that its targeting is determined by the 20-nucleotide sequence of the gRNA molecule, this system allows unprecedentedly facile engineering. Furthermore, it is amenable to multiplexing in cells in which delivery and expression of the reagents is feasible. Several studies have reported the applicability of the CRISPR/Cas9 system to in planta genome editing in several plant species including rice, *Nicotiana benthamiana*, and *Arabidopsis* (Nekrasov et al., (2013) *Nature Biotechnol.* 31: 691-693; Shan et al., (2013) *Nature Biotechnol.* 31: 686-688; Li et al., (2013) *Nature Biotechnol.* 31: 688-691). In these studies, to achieve moderate efficiencies of targeted genome modification, it was necessary to generate transformant lines that stably expressed the Cas9 and gRNA molecules; the heritability of the resultant modifications was monitored in subsequent generations. It is time-consuming to generate these stably expressing lines; therefore, efficient delivery methods are urgently needed to expedite and maximize the usefulness of this technology for trait discovery and development. Currently, the lack of efficient delivery methods represents a major barrier to achieving highly efficient targeted modification across plant species.

SUMMARY

Efficient targeted genomic editing holds much promise in the discovery and development of highly important agricultural traits. Clustered Regularly Interspaced Palindromic Repeats (CRISPRs)/CRISPR associated (Cas) type II systems have been employed for targeted genome editing applications across eukaryotic species including plants. Stable expression of Cas9 and gRNA transgenes is required for editing plant genes, and multiplexing is a challenging task. The present disclosure provides a viral-mediated genome-editing platform that facilitates multiplexing, obviates stable transformation, and is applicable across plant species. The RNA2 genome of the tobacco rattle virus (TRV), used frequently in Virus-Induced Gene Signalling (VIGS) applications, was engineered to carry and systemically deliver the guide RNA molecules into *Nicotiana benthamiana* plants overexpressing Cas9 endonuclease. High genomic modification frequencies were observed in inoculated as well as systemic leaves including the plant growing points. This system facilitates multiplexing and can lead to germinal transmission of the genomic modifications in the progeny, thereby obviating the requirements of repeated transformations and tissue culture. The editing platform of the disclosure is useful in plant genome engineering and applicable across plant species amenable to viral infections for agricultural biotechnology applications.

One aspect of the disclosure encompasses embodiments of a method for modifying a target site in the genome of a plant cell, the method comprising providing a nucleic acid sequence encoding a guide RNA-PAM to a plant cell having a Cas endonuclease, wherein the guide RNA is delivered to the plant cell by a plant virus vector, and wherein said guide RNA and Cas endonuclease are capable of forming a complex that enables the Cas endonuclease to introduce a double strand break at said target site.

In some embodiments of this aspect of the disclosure, the plant virus vector can be a genome of the Tobacco Rattle Virus (TRV).

In some embodiments of this aspect of the disclosure, the nucleic acid sequence encoding a guide RNA-PAM can be inserted into the TRV-RNA2 genome of the TRV-derived vector.

In some embodiments of this aspect of the disclosure, the method can further comprise targeting a plurality of target sites in the same recipient plant cell or cells, wherein step (a) of said method comprises delivering to the plant cell expressing a Cas9 endonuclease a plurality of recombinant viral vectors, wherein said viral vectors each independently comprises a nucleic acid sequence encoding a guide RNA-PAM complementary to a targeted region of the plant cell genome and a Protospacer Adjacent Motif (PAM), and wherein each member of the plurality of recombinant viral vectors comprises a gRNA-PAM sequence not found in the other recombinant viral vectors delivered to the plant cell.

Another aspect of the of this aspect disclosure encompasses embodiments of a method for modifying a target site in the genome of a plant cell, the method comprising providing a nucleic acid sequence encoding a guide RNA-PAM to a plant cell having a Cas endonuclease, and optionally a polynucleotide modification template, wherein the guide RNA, and optionally the polynucleotide modification template, is delivered to the plant cell by a plant virus vector, and wherein said guide RNA and Cas endonuclease can be capable of forming a complex that enables the Cas endonuclease to introduce a double strand break at said target site, and wherein said polynucleotide modification template comprises at least one nucleotide modification of said target site.

In some embodiments of this aspect of the methods of the disclosure, the target site in the genome of a cell can be selected from the group consisting of a promoter sequence, a terminator sequence, a regulatory element sequence, a splice site, a coding sequence, a polyubiquitination site, an intron site, and an intron enhancing motif.

Another aspect of the disclosure encompasses embodiments of a recombinant nucleic acid construct comprising a plant virus vector comprising a promoter operably linked to a nucleic acid sequence encoding a guide RNA-PAM, wherein said guide RNA can be capable of forming a complex with a plant optimized Cas9 endonuclease, and wherein said complex is capable of binding to and creating a double strand break in a genomic target sequence said plant genome.

In some embodiments of this aspect of the disclosure, the plant virus vector is a genome of the Tobacco Rattle Virus (TRV).

In some embodiments of this aspect of the disclosure, the nucleic acid sequence encoding a guide RNA-PAM can be inserted into the TRV-RNA2 genome of the TRV-derived vector.

Another aspect of the disclosure encompasses embodiments of a genetically modified plant, or a progeny thereof, generated by a method for modifying a target site in the genome of a plant cell, the method comprising genetically modifying plant cell or cells or cells having a Cas endonuclease by providing to said cell or cells a recombinant nucleic acid construct comprising a nucleic acid sequence encoding a guide RNA-PAM, and optionally a polynucleotide modification template, wherein the guide RNA-PAM, and optionally the polynucleotide modification template, is delivered to the plant cell or cells by a plant virus vector, and wherein said guide RNA-PAM and Cas endonuclease are capable of forming a complex that enables the Cas endonuclease to introduce a double strand break at said target site, and wherein said polynucleotide modification template comprises at least one nucleotide modification of said target site; culturing the genetically modifying plant cell or cells or cells to generate a plant embryo or mature plant; and optionally generating progeny from said embryo or mature plant.

BRIEF DESCRIPTION OF THE DRAWINGS

Many aspects of the disclosure can be better understood with reference to the following drawings.

FIGS. 1A-1D illustrate targeted genome modification in planta using TRV.

FIG. 1A schematically illustrates the experimental scheme of the methods of the disclosure.

FIG. 1B illustrates T7 endonuclease 1 (T7E1)-based mutation analysis in inoculated and systemic leaves. Samples were collected from inoculated and systemic leaves. Ten days after infection (10DAI) genomic DNA was enriched with NcoI and the PCR products subjected to T7E1. Mutation was detected in leaves in inoculated (lane 3) and systemic leaves (lane 4, 5, 7) both only in plants co-infiltrated with pYL192, but not in systemic leaves of plants infiltrated only with SPDK.pEBV::PDS.gRNA (Lane 6) or pYL156.U6::PDS.gRNA with pYL192 (Lane 8). Lanes 1 and 2 are controls.

FIG. 1C illustrates the alignment of reads (SEQ ID NO: 124-129 against SEQ ID NO: 123) from the PCR product cloned and Sanger sequenced from inoculated leaves. Topmost is the VVT sequence (SEQ ID NO: 123) (target sequence is underlined, the NcoI site is indicated by a line and the PAM by dots), followed by the number of different indels formed to the right of sequence (− means deletion of x nucleotides and + means insertion of x nucleotides).

FIG. 1D illustrates the alignment of reads (SEQ ID NO: 130-136 against SEQ ID NO: 123) from the PCR product cloned and Sanger sequenced from systemic leaves. Topmost is the VVT sequence (SEQ ID NO: 123) (target sequence is underlined, the NcoI site is indicated by a line and the PAM by dots), followed by the number of different indels formed to the right of sequence (− means deletion of x nucleotides and + means insertion of x nucleotides).

FIGS. 2A-2C illustrate mutation analyses for NB.PCNA and genomic target multiplexing.

FIG. 2A illustrates a T7 Endonuclease1 (T7E1)-based NB.PCNA mutation analysis on PCR product from gDNA. Cas9-expressing plants were co-infiltrated with SPDK.pEBV::PCNA.sgRNA, and pYL192. Three independent plants (Lanes 1, 2, and 3) clearly show indel formation compared to vector control (Lanes 4, 5, and 6).

FIG. 2B illustrates the alignment of reads (SEQ ID NO: 138-141 against SEQ ID NO: 137) from the PCR product Sanger sequenced clones. Topmost is the VVT sequence (target sequence is underlined, NcoI site is indicated by a line and PAM by dots), followed by the number of different indels formed to the right of sequence (− means deletion of x nucleotides and + means insertion of x nucleotides).

FIG. 2C illustrates the multiplexing of different target mutations. gDNA samples were collected from Cas9-expressing plants co-infiltrated with SPDK.pEBV::PDS.sgRNA, SPDK.pEBV::PCNA.sgRNA and pYL192. PCR was performed independently for PDS3 and PCNA with respective primers. PCR product was subjected to T7E1 digestion. The PCNA3 mutation is shown in lane 3 and 4, and the PDS mutation is shown in lanes 7 and 8. Lane 1 is vector control.

FIGS. 3A-3D illustrate in planta Cas9 nuclear localization and expression.

FIG. 3A illustrates Cas9-GFP and Cas9 constructs in binary vectors for Cas9 localization and for generating Cas9-expressing *Nicotiana benthamiana*. NLS, Nuclear Localization Signal, 3× Flag tag.

FIG. 3B illustrates Cas9-GFP localization in infiltrated leaves, visualized by confocal microscopy. DAPI was used to stain nuclei. DAPI and GFP merge to the cell nuclei.

FIG. 3C illustrates Cas9 expression confirmation in transgenic *N. benthamiana* by Semi-quantitative RT-PCR. Actin1 was used as normalization control.

FIG. 3D illustrates Cas9 expression confirmation by western blot in T2 lines. Anti-flag antibody was used to detect flag-Cas9 in transgenic *N. benthamiana*. Lower panel was used as protein loading control.

FIG. 4A illustrates TRV RNA1 and RNA2 organization and modification for targeted genome editing in planta. RNA1 in binary system: LB (lift border); p35S (2×CaMV 35S promoter); RdRP (134/194 kDa RNA dependent RNA polymerase); MP (Movement protein); 16 k (cysteine rich protein); Rz (self-cleaving ribozyme); Tnos (nopaline synthase terminator); RB (right border). RNA2: LB, 2x35S; CP (Coat protein); MCS (multiple cloning sites); Rz; Tnos; and RB. In the RNA2-U6::gRNA, sgRNA under AtU6 promoter was ligated in the MCS. In RNA2-pEBV-gRNA, sgRNA was inserted to be under the pEBV viral promoter.

FIGS. 12A and 12B illustrate off-targeting of CRISPR/ Cas9 in *N. benthamiana*.

FIG. 12A illustrates a T7E1 assay from SPDK-pEBV:: sgRNA-PDS3 plus pYL192 infiltrated leaves. gDNA amplified PCR fragments around the potential off targets.

FIG. 12B illustrates a control T7E1 non-treated PCR product.

FIG. 14 illustrates the nucleotide sequence of Cas9 (flag-nls-cas9-nls) (SEQ ID NO: 1).

FIG. 15 illustrates the nucleotide sequence of the sgRNA (NB-PDS3) (SEQ ID NO: 2) and the map thereof. The NB-PDS3 target-2 is in bold.

FIG. 16 illustrates the nucleotide sequence of the NB-PDS3 (SEQ ID NO: 3) selected region and the map thereof. The NB-PDS3 target-2 is in bold.

FIG. 17 illustrates the nucleotide sequence of the sgRNA (NB.PCNA) (SEQ ID NO: 4) selected region and the map thereof. The NB-PDS3 target-2 Ssp1 is in bold.

FIG. 18 illustrates the nucleotide sequence of the NB.PCNA (SEQ ID NO: 5) selected region and the map thereof.

FIG. 19 illustrates the nucleotide sequence of pYL156 RNA2 (SEQ ID NO: 6).

FIG. 20 illustrates the map of the construct pYL156 RNA2. Locations of restriction sites are indicated.

FIG. 21 illustrates the nucleotide sequence of *Arabidopsis* U6 promoter sequence for expression of sgRNA (SEQ ID NO: 7).

FIG. 22 illustrates the nucleotide sequence of SPDK-RNA2 (SEQ ID NO: 8).

FIG. 24 illustrates the nucleotide sequence of YL192 (SEQ ID NO: 9).

FIG. 28 illustrates the confirmation of indels in the F1 progeny of *N. bethamiana* plants using restriction endonuclease protection assay. Confirmation of the indels in the F1 progeny of *N. bethamiana* plants. DNA was extracted from four pools, each pool is made of leaf discs from 50 seedlings. 1 µg of 404 bp PCR-amplified product was subjected to NcoI digestion. NcoI resistant bands indicating the presence of genomic modifications are highly enriched in the progeny of Cas9-overexpressing plants infiltrated with RNA2.PEBV:: PDS compared to control.

FIG. 29 illustrates the confirmation of Cas9-GFP expression in T3 *Arabidopsis* plants by Western blot analysis.

FIGS. 32A-32C illustrate TRV-expressed gRNA can target *Arabidopsis* genomic sequences AtGL1, AtADH1, and AtTT4 in Cas9-GFP expressing plants.

FIG. 32A illustrates a map showing the AtGI1 fragment used to PCR amplify DNA sequence flanking targeted sequence.

FIG. 32B illustrates the results of a T7E1 assay for mutation/indels detection. Lane 1 and 4 show indels formation compared to control lane 5.

FIG. 32C illustrates the result of a PstI recognition site loss assay for ADH1 (lane 1) and TT4 (lane 3) lanes 2 and 4 are respective controls of ADH1 and TT4. Expected DNA bands are represented with stars.

Figure 1A:
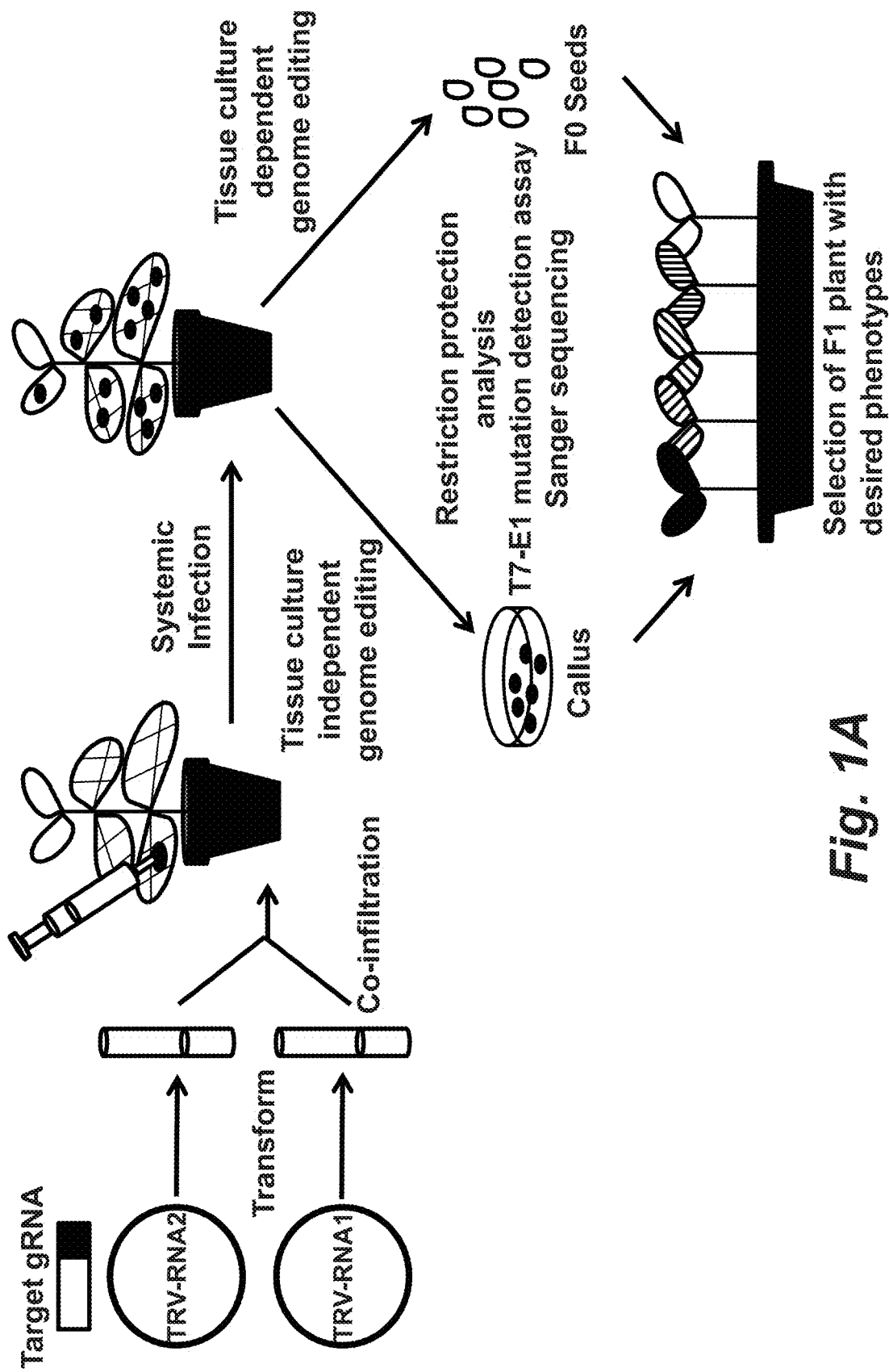
Figure 1B:
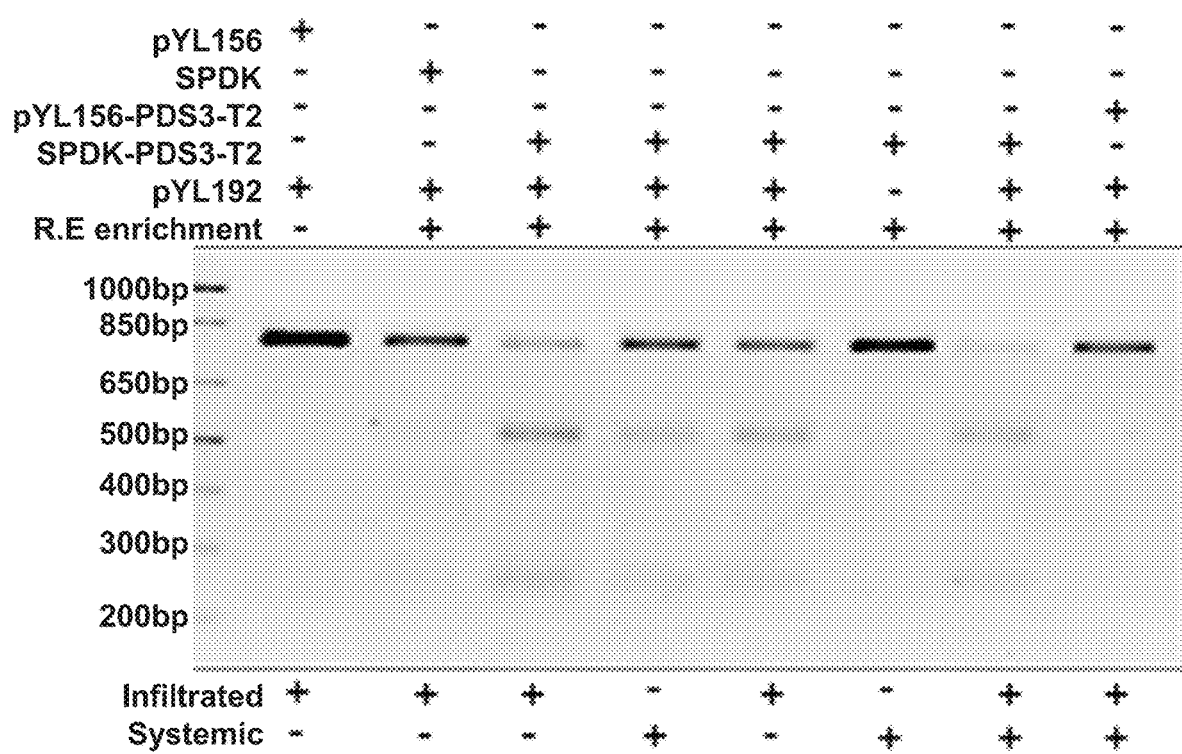

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, toxicology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Definitions

The term "agroinfiltration" as used herein refers to a method in plant biology to induce expression of genes in a plant or to produce a desired protein. In the method a suspension of *Agrobacterium tumefaciens* is injected into a plant leaf, where it transfers the desired gene to plant cells. The benefit of agroinfiltration when compared to traditional plant transformation is speed and convenience.

First step of the protocol is to introduce a gene of interest to a strain of *Agrobacterium*. Subsequently the strain is grown in a liquid culture and the resulting bacteria are washed and suspended into a suitable buffer solution. This solution is then placed in a syringe (without a needle). The tip of the syringe is pressed against the underside of a leaf while simultaneously applying gentle counterpressure to the other side of the leaf. The *Agrobacterium* solution is then injected into the airspaces inside the leaf through stomata, or sometimes through a tiny incision made to the underside of the leaf.

Vacuum infiltration is another way to penetrate *Agrobacterium* deep into plant tissue. In this procedure, leaf disks, leaves, or whole plants are submerged in a beaker containing the solution, and the beaker is placed in a vacuum chamber. The vacuum is then applied, forcing air out of the stomata. When the vacuum is released, the pressure difference forces solution through the stomata and into the mesophyll.

Once inside the leaf the *Agrobacterium* remains in the intercellular space and transfers the gene of interest in high copy numbers into the plant cells. The gene is then transiently expressed (no selection for stable integration is performed). The plant can be monitored for a possible effect in the phenotype, subjected to experimental conditions or harvested and used for purification of the protein of interest. Many plant species can be processed using this method, but the most common ones are *Nicotiana benthamiana* and *Nicotiana tabacum.*'

The term "allele" as used herein refers to one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

The term "Cas endonuclease recognition (CER) domain" of a guide polynucleotide as used herein refers to a nucleotide sequence (such as a second nucleotide sequence domain of a guide polynucleotide) that interacts with a Cas endonuclease polypeptide. The CER domain can be composed of a DNA sequence, a RNA sequence, a modified DNA sequence, a modified RNA sequence, or any combination thereof. The guide polynucleotide and Cas endonuclease are capable of forming a complex that enables the Cas endonuclease to introduce a double strand break at a DNA target site.

The terms "Cas gene" and "CRISPR-associated (Cas) gene" are used interchangeably herein. A comprehensive review of the Cas protein family is presented in Haft et al. (2005) *Computational Biology, PLoS Comput. Biol.* 1: e60. doi:10.1371/journal.pcbi.0010060. At least 41 CRISPR-associated (Cas) gene families are described. CRISPR systems belong to different classes, with different repeat patterns, sets of genes, and species ranges. The number of Cas genes at a given CRISPR locus can vary between species.

A Cas endonuclease is a Cas protein encoded by a Cas gene, and is capable of introducing a double strand break into a DNA target sequence. The Cas endonuclease is guided by a guide polynucleotide to recognize and optionally introduce a double strand break at a specific target site into the genome of a cell. Accordingly, as used herein, the term "guide polynucleotide/Cas endonuclease system" can refer to a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide polynucleotide, but only if the correct Protospacer-Adjacent Motif (PAM) is approximately oriented at the 3' end of the target sequence.

An advantageous Cas endonuclease gene for use in the methods and systems of the present disclosure is a Cas9 endonuclease. The Cas endonuclease gene can be a plant codon optimized *Streptococcus pyogenes* Cas9 gene encoding a Cas9 endonuclease that can recognize any genomic sequence of the form $N_{(12-30)}NGG$. The Cas endonuclease can be introduced directly into a cell by any method known in the art, for example, but not limited to transient introduction methods, transfection and/or topical application. It is contemplated that a plant receiving the viral-delivered guide nucleic acid according to the methods of the present disclosure can be a stable transgenic (genetically-modified) plant expressing a heterologous Cas endonuclease.

The terms "chimeric RNA", "chimeric guide RNA", "guide RNA", "single guide RNA" and "synthetic guide RNA" as used herein are used interchangeably and refer to the polynucleotide sequence comprising a guide polynucleotide, a tracr sequence and a tracr mate sequence.

The term "coding sequence" as used herein refers to a polynucleotide sequence which codes for a specific amino acid sequence.

The terms "codon-modified gene" or "codon-preferred gene" or "codon-optimized gene" as used herein refer to a gene having its frequency of codon usage designed to mimic the frequency of preferred codon usage of the host plant cell.

The term "complementarity" as used herein refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

The terms "conserved domain" or "motif" as used herein refer to a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

Polynucleotide and polypeptide sequences, variants thereof, and the structural relationships of these sequences can be described by the terms "homology", "homologous", "substantially identical", "substantially similar" and "correspondingly substantially" which are used interchangeably herein. These terms as used herein refer to polypeptide or nucleic acid fragments wherein changes in one or more amino acids or nucleotide bases do not affect the function of the molecule, such as the ability to mediate gene expression or to produce a certain phenotype. These terms also refer to modification(s) of nucleic acid fragments that do not substantially alter the functional properties of the resulting nucleic acid fragment relative to the initial, unmodified fragment. These modifications include deletion, substitution, and/or insertion of one or more nucleotides in the nucleic acid fragment.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The terms "crossed," "cross," or "crossing" as used herein refer to the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

The term "dicot" as used herein refers to the subclass of angiosperm plants also knows as "dicotyledoneae" and includes reference to whole plants, plant organs (e.g., leaves, stems, roots, etc.), seeds, plant cells, and progeny of the same. Plant cell, as used herein includes, without limitation, seeds, suspension cultures, embryos, meristematic regions, callus tissue, leaves, roots, shoots, gametophytes, sporophytes, pollen, and microspores.

The term "expression" as used herein refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The term "gene" as used herein refers to a nucleic acid fragment that expresses a functional molecule such as, but not limited to, a specific protein, including regulatory sequences preceding (5' non-coding sequences) and following (3' non-coding sequences) the coding sequence.

The term "genome" as used herein, referring to a plant cell encompasses not only chromosomal DNA found within the nucleus, but organelle DNA found within subcellular components (e.g., mitochondria, or plastid) of the cell.

The term "genomic region" as used herein refers to a segment of a chromosome in the genome of a plant cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

The term "guide polynucleotide" as used herein refers to a polynucleotide sequence that can form a complex with a Cas endonuclease and enables the Cas endonuclease to recognize and optionally cleave a DNA target site. The guide polynucleotide can be a single molecule or a double molecule. The guide polynucleotide sequence can be a RNA sequence, a DNA sequence, or a combination thereof (a RNA-DNA combination sequence).

The guide polynucleotide such as guide RNA can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. The first molecule of the duplex guide polynucleotide can comprise a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides).

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide.

The guide RNA can be introduced into a plant or plant cell directly using any method known in the art such as, but not limited to, particle bombardment or topical applications. The guide RNA can be introduced indirectly by introducing a recombinant DNA molecule comprising the corresponding guide DNA sequence operably linked to a plant specific promoter that is capable of transcribing the guide RNA in said plant cell. The guide RNA may be introduced via particle bombardment or *Agrobacterium* transformation of a recombinant DNA construct comprising the corresponding guide DNA operably linked, for example, to a plant U6 polymerase III promoter. Most advantageously, however, the guide nucleic acid is delivered to a plant cell using the viral vector system according to the methods of the present disclosure.

The term "guide polynucleotide" as used herein refers to any polynucleotide sequence having sufficient complementarity with a target polynucleotide sequence to hybridize with the target sequence and direct sequence-specific binding of a CRISPR complex to the target sequence. The degree of complementarity between a guide polynucleotide and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). A guide polynucleotide can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. A guide polynucleotide can be less than about 75, 50, 45, 40, 35, 30, 25, 20, 15, 12, or fewer nucleotides in length. The ability of a guide polynucleotide to direct sequence-specific binding of a CRISPR complex to a target sequence may be assessed by any suitable assay. For example, the components of a CRISPR system sufficient to form a CRISPR complex, including the guide polynucleotide to be tested, may be provided to a host cell having the corresponding target sequence, such as by transfection with vectors encoding the components of the CRISPR sequence, followed by an assessment of preferential cleavage within the target sequence. Similarly, cleavage of a target polynucleotide sequence may be evaluated in a test tube by providing the target sequence, components of a CRISPR complex, including the guide polynucleotide to be tested and a control guide polynucleotide different from the test guide polynucleotide, and comparing binding or rate of cleavage at the target sequence between the test and control guide polynucleotide reactions. Other assays are possible, and will occur to those skilled in the art.

A guide polynucleotide can be selected to reduce the degree of secondary structure within the guide polynucleotide. Secondary structure may be determined by any suitable polynucleotide folding algorithm. Some programs are based on calculating the minimal Gibbs free energy. An example of one such algorithm is mFold, as described by Zuker & Stiegler ((1981) *Nucleic Acids Res.* 9, 133-148). Another example folding algorithm is the online webserver RNAfold, developed at Institute for Theoretical Chemistry at the University of Vienna, using the centroid structure prediction algorithm (see e.g. Gruber et al., (2008) *Cell* 106: 23-24; and Carr & Church (2009) *Nature Biotechnol.* 27: 1151-1162).

The term "heterologous" is used broadly below to indicate that the gene/sequence of nucleotides in question have been introduced into the cells in question (e.g. of a plant or an ancestor thereof) using genetic engineering, i.e. by human intervention. A heterologous gene may replace an endogenous equivalent gene, i.e. one which normally performs the same or a similar function, or the inserted sequence may be additional to the endogenous gene or other sequence. Nucleic acid heterologous to a cell may be non-naturally occurring in cells of that type, variety or species. Thus the heterologous nucleic acid may comprise a coding sequence of, or derived from, a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression.

The term "homologous recombination" as used herein refers to the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology.

Homology-directed repair (HDR) is a mechanism in cells to repair double-stranded and single stranded DNA breaks. Homology-directed repair includes homologous recombination (HR) and single-strand annealing (SSA) (Lieber. (2010) *Annu. Rev. Biochem.* 79: 181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks.

Error-prone DNA repair mechanisms can produce mutations at double-strand break sites. The Non-Homologous-End-Joining (NHEJ) pathways are the most common repair mechanism to bring the broken ends together (Bleuyard et al., (2006) *DNA Repair* 5: 1-12). The structural integrity of chromosomes is typically preserved by the repair, but deletions, insertions, or other rearrangements are possible. The two ends of one double-strand break are the most prevalent substrates of NHEJ (Kirk et al., (2000) *EMBO J.* 19: 5562-5566), however if two different double-strand breaks occur, the free ends from different breaks can be ligated and result in chromosomal deletions (Siebert & Puchta, (2002) *Plant Cell* 14:1121-1131), or chromosomal translocations between different chromosomes (Pacher et al., (2007) *Genetics* 175: 21-29).

Episomal DNA molecules can also be ligated into the double-strand break, for example, integration of T-DNAs into chromosomal double-strand breaks (Chilton & Que, (2003) *Plant Physiol.* 133: 956-965; Salomon & Puchta, (1998) *EMBO J.* 17: 6086-6095). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) *Plant Cell* 16: 342-352). Ectopic and/or epigenic DNA sequences may also serve as a DNA repair template for homologous recombination (Puchta, (1999) *Genetics* 152: 1173-1181). *Genome Editing Using the Guide RNA/Cas Endonuclease System*: The guide RNA/Cas endonuclease systems of the present disclosure can be used in combination with a co-delivered polynucleotide modification template to allow for editing of a genomic nucleotide sequence of interest. The guide RNA/Cas endonuclease system of the present disclosure can be deployed where the guide polynucleotide does not solely comprise ribonucleic acids but wherein the guide polynucleotide comprises a combination of RNA-DNA molecules or solely comprise DNA molecules.

The term "homology" as used herein refers to DNA sequences that are similar. For example, a "region of homology to a genomic region" that is found on the donor DNA is a region of DNA that has a similar sequence to a given "genomic region" in the plant genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bp. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) Molecular Cloning: A Laboratory Manual, (Cold Spring Harbor Laboratory Press, NY); Current Protocols in Molecular Biology, Ausubel et al., Eds (1994) Current Protocols, (Greene Publishing Associates, Inc. and John Wiley & Sons, Inc.); and Tijssen (1993) Laboratory Techniques in Biochemistry and Molecular Biology-Hybridization with Nucleic Acid Probes, (Elsevier, New York).

The term "hybridization" as used herein refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

The term "introduced" as used herein refers to providing a nucleic acid (e.g., expression construct) or protein to a cell. The term "introduced" also includes reference to the incorporation of a nucleic acid into a eukaryotic or prokaryotic cell where the nucleic acid may be incorporated into the genome of the cell, and includes reference to the transient provision of a nucleic acid or protein to the cell. "Introduced" further includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

The term "mature" protein as used herein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

The terms "modified nucleotide" or "edited nucleotide" as used herein refer to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "mutated gene" as used herein refers to a gene that has been altered through such as human intervention. Such a "mutated gene" has a sequence that differs from the sequence of the corresponding non-mutated gene by at least one nucleotide addition, deletion, or substitution. The mutated gene can comprise an alteration that results from a guide polynucleotide/Cas endonuclease system as disclosed herein. A mutated plant is a plant comprising a mutated gene.

The term "native gene" refers to a gene as found in nature with its own regulatory sequences.

The terms "3' non-coding sequences", "transcription terminator" or "termination sequences" as used herein refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1: 671-680.

The terms "non-naturally occurring" or "engineered" as used herein are used interchangeably and refer to the involvement of the hand of man. The terms, when referring to nucleic acid molecules or polypeptides mean that the nucleic acid molecule or the polypeptide is at least substantially free from at least one other component with which they are naturally associated in nature and as found in nature.

The term "nickase" as used herein refers to modified versions of the Cas9 enzyme containing a single inactive catalytic domain, either RuvC- or HNH-. With only one active nuclease domain, the Cas9 "nickase" will cut only one strand of the target DNA, thereby generating a single-strand break or 'nick'. A Cas9 nickase is still able to bind DNA based on guide polynucleotide specificity, though nickases will only cut one of the DNA strands. The majority of CRISPR plasmids are derived from *S. pyogenes* and the RuvC domain inactivated, for example, by a D10A mutation.

The term "off-target effect" as used herein refers to when flexibility in the base-pairing interactions between the guide polynucleotide sequence and the genomic DNA target sequence allows imperfect matches to the target sequence to be cut by Cas9. Single mismatches at the 5' end of the guide polynucleotide (furthest from the PAM site) can be permissive for off-target cleavage by Cas9.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In one example, the complementary RNA regions can be operably linked, either directly or indirectly, 5' to the target mRNA, or 3' to the target mRNA, or within the target mRNA, or a first complementary region is 5' and its complement is 3' to the target mRNA.

The term "percentage of sequence identity" as used herein refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins & Sharp, (1989) *CABIOS* 5: 151-153; Higgins et al., (1992) *Comput. Appl. Biosci.* 8: 189-191) and found in the MegAlign™ program of the LASERGENE bioinformatics computing suite (DNASTAR Inc., Madison, Wis.). After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins & Sharp, (1989) *CABIOS* 5: 151-153; Higgins et al., (1992) *Comput. Appl. Biosci.* 8: 189-191) and found in the MegAlign™ v6.1 program of the LASERGENE bioinformatics computing suite (DNASTAR Inc., Madison, Ws.). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff & Henikoff, (1989) *Proc. Natl. Acad. Sci. U.S.A.* 89:10915). GAP uses the algorithm of Needleman & Wunsch, (1970) *J. Mol. Biol.* 48: 443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

"BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

The term "phenotypic marker" as used herein refers to a screenable or selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products that provide resistance against otherwise toxic compounds including antibiotics, such as, spectinomycin, ampicillin, kanamycin, tetracycline, Basta, neomycin phosphotransferase II (NEO), hygromycin phosphotransferase (HPT)) and the like; DNA segments that encode products that are otherwise lacking in the recipient cell (e.g., tRNA genes, auxotrophic markers);

DNA segments that encode products which can be readily identified (e.g., phenotypic markers such as 11-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification. Additional selectable markers can include, but are not limited to, genes that confer resistance to herbicidal compounds.

The term "plant" refers to whole plants, plant organs, plant tissues, seeds, plant cells, seeds, and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in a plant or in a plant organ, tissue or cell culture. The term "plant organ" refers to plant tissue or a group of tissues that constitute a morphologically and functionally distinct part of a plant. "Progeny" comprises any subsequent generation of a plant.

A transgenic plant includes, for example, a plant that comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by the genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

A fertile plant is a plant that produces viable male and female gametes and is self-fertile. Such a self-fertile plant can produce a progeny plant without the contribution from any other plant of a gamete and the genetic material contained therein. As used herein, a "male sterile plant" is a plant that does not produce male gametes that are viable or otherwise capable of fertilization. As used herein, a "female sterile plant" is a plant that does not produce female gametes that are viable or otherwise capable of fertilization. It is recognized that male-sterile and female-sterile plants can be female-fertile and male-fertile, respectively. It is further recognized that a male fertile (but female sterile) plant can produce viable progeny when crossed with a female fertile plant and that a female fertile (but male sterile) plant can produce viable progeny when crossed with a male fertile plant.

Any commercially or scientifically valuable plant is envisaged in accordance with these embodiments of the invention. However, it is most advantageous if such plants are susceptible to a viral infection either naturally or induced or resulting from artificial means. Such viruses are advantageously modified to deliver a heterologous nucleotide sequence such as a guide nucleotide sequence to a plant cell. A suitable plant for use with the method of the invention can be any monocotyledonous or dicotyledonous plant including, but not limited to, maize, wheat, barley, rye, oat, rice, soybean, peanut, pea, lentil and alfalfa, cotton, rapeseed, canola, pepper, sunflower, potato, tobacco, tomato, lettuce, mums, arabidopsis, broccoli, cabbage, beet, quinoa, spinach, cucumber, squash, watermelon, beans, hibiscus, okra, apple, rose, strawberry, chile, garlic, onions, sorghum, eggplant, eucalyptus, pine, a tree, an ornamental plant, a perennial grass and a forage crop, coniferous plants, moss, algae, as well as other plants listed in World Wide Web.

Accordingly, plant families may comprise, but are not limited to, Alliaceae, Amaranthaceae, Amaryllidaceae, Apocynaceae, Asteraceae, Boraginaceae, Brassicaceae, Campanulaceae, Caryophyllaceae, Chenopodiaceae, Compositae, Cruciferae, Cucurbitaceae, Euphorbiaceae, Fabaceae, Gramineae, Hyacinthaceae, Labiatae, Leguminosae-Papilionoideae, Liliaceae, Linaceae, Malvaceae, Phytolaccaceae, Poaceae, Pinaceae, Rosaceae, Scrophulariaceae, Solanaceae, Tropaeolaceae, Umbelliferae and Violaceae.

Such plants include, but are not limited to, *Allium cepa, Amaranthus caudatus, Amaranthus retroflexus, Antirrhinum majus, Arabidopsis thaliana, Arachis hypogaea, Artemisia* sp., *Avena sativa, Bellis perennis, Beta vulgaris, Brassica campestris, Brassica campestris* ssp. *Napus, Brassica campestris* ssp. *Pekinensis, Brassica juncea, Calendula officinalis, Capsella bursa-pastoris, Capsicum annuum, Catharanthus roseus, Chemanthus cheiri, Chenopodium album, Chenopodium amaranticolor, Chenopodium foetidum, Chenopodium quinoa, Coriandrum sativum, Cucumis melo, Cucumis sativus, Glycine max, Gomphrena globosa, Gossypium hirsutum cv. Siv'on, Gypsophila elegans, Helianthus annuus, Hyacinthus, Hyoscyamus niger, Lactuca sativa, Lathyrus odoratus, Linum usitatissimum, Lobelia erinus, Lupinus mutabilis, Lycopersicon esculentum, Lycopersicon pimpinellifolium, Melilotus albus, Momordica balsamina, Myosotis sylvatica, Narcissus pseudonarcissus, Nicandra physalodes, Nicotiana benthamiana, Nicotiana clevelandii, Nicotiana glutinosa, Nicotiana rustica, Nicotiana sylvestris, Nicotiana tabacum, Nicotiana edwardsonii, Ocimum basilicum, Petunia hybrida, Phaseolus vulgaris, Phytolacca Americana, Pisum sativum, Raphanus sativus, Ricinus communis, Rosa sericea, Salvia splendens, Senecio vulgaris, Solanum lycopersicum, Solanum melongena, Solanum nigrum, Solanum tuberosum, Solanum pimpinellifolium, Spinacia oleracea, Stellaria media, Sweet Wormwood, Trifolium pratense, Trifolium repens, Tropaeolum majus, Tulipa, Vicia faba, Vicia villosa* and *Viola arvensis*. Other plants that may be infected include *Zea maize, Hordeum vulgare, Triticum aestivum, Oryza sativa* and *Oryza glaberrima*.

The term "plant-optimized nucleotide sequence" as used herein refers to a nucleotide sequence that has been optimized for increased expression in plants, particularly for increased expression in plants or in one or more plants of interest. For example, a plant-optimized nucleotide sequence can be synthesized by modifying a nucleotide sequence encoding a protein such as, for example, double-strand-break-inducing agent (e.g., an endonuclease) as disclosed herein, using one or more plant-preferred codons for improved expression. See, for example, Campbell & Gowri (1990) *Plant Physiol.* 92: 1-11 for a discussion of host-preferred codon usage.

Methods are available in the art for synthesizing plant-preferred genes. See, for example, U.S. Pat. Nos. 5,380,831, and 5,436,391, and Murray et al. (1989) *Nucleic Acids Res.* 17: 477-498, herein incorporated by reference. Additional sequence modifications are known to enhance gene expression in a plant host. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given plant host, as calculated by reference to known genes expressed in the host plant cell. When possible, the sequence is modified to avoid one or more predicted hairpin secondary mRNA structures. Thus, "a plant-optimized nucleotide sequence" of the present disclosure comprises one or more of such sequence modifications.

The term "plant viral (virus) vector" as used herein refers to a nucleic acid vector including a DNA vector (e.g., a plasmid), a RNA vector, virus or other suitable replicon (e.g., viral vector) encoding for viral genes or parts of viral genes.

Viruses that have been shown to be useful for the transformation of plant hosts include, but are not limited to, Cauliflower Mosaic Virus (CaMV), Tobacco Mosaic Virus (TMV) and Bean Virus (BV). Transformation of plants using plant viruses is described in, for example, Gluzman et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Other viruses which may be advantageously useful in transformation of plant hosts include, but are not limited to, tobacco rattle virus (TRV) and its related viruses. TRV is known for its ability to infect meristematic tissues, it comprises a broad host range and different strain isolates. For example strain N5, obtained from narcissus, causes severe necrosis in *Nicotiana clevelandii* (Harrison et al. (1983) *Ann. Appl. Biol.* 102: 331-338). The hypochoeris mosaic virus (HMV), which is serologically related to TRV infects the Asteraceae family of plants (Brunt & Stace-Smith (1978) *Ann. Appl. Biol.* 90: 205-214). The tobacco rattle virus strain TCM, originally obtained from tulip, is serologically closely related to the Dutch serotype of Pea early-browning virus. Furthermore, there are also monocotyledons species susceptible to TRV, as for example *Avena sativa* (family Poaceae).

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein that will encapsidate the viral DNA. If the virus is an RNA virus, the virus is generally cloned as a cDNA and inserted into a plasmid. The plasmid is then used to make all of the constructions. The RNA virus is then produced by replicating the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931. TRV-based expression vectors have been described in for example U.S. Pat. No. 7,229,829.

TRV is a positive strand RNA virus with a bipartite genome, hence the genome is divided into two positive-sense, single-stranded RNAs, that may be separately encapsidated into viral particles. The two TRV genomic RNA vectors used by the present invention are referred to herein as pTRV1 (GenBank Accession No: AF406990) and pTRV2 (GenBank Accession No: AF406991), wherein pTRV1 encodes polypeptides that mediate replication and movement in the host plant while pTRV2 encodes coat proteins. In certain embodiments, the nucleic acid sequence of pTRV2 is devoid of 2b sequence. pTRV2 vectors without the 2b region are more efficient in gene expression in meristematic tissues.

The selection of the vector may be dependent on the target plant such as monocots. The modified wheat streak mosaic virus (WSMV) has been previously shown to express NPT II and _ -glucuronidase (GUS) in monocots (e.g. wheat, barley, oat and maize)

The terms "plasmid", "vector" and "cassette" as used herein refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell.

The term "polymerase chain reaction (PCR)" as used herein refers to a technique for the synthesis of specific DNA segments and consists of a series of repetitive denaturation, annealing, and extension cycles. Typically, a double-stranded DNA is heat denatured, and two primers complementary to the 3' boundaries of the target segment are annealed to the DNA at low temperature, and then extended at an intermediate temperature. One set of these three consecutive steps is referred to as a "cycle".

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "polynucleotide modification template" as used herein refers to a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The term "amino acid" as used herein refers to natural and/or unnatural or synthetic amino acids, including glycine and both the D or L optical isomers, and amino acid analogs and peptidomimetics.

The term "promoter" as used herein refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since patterns of expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

The term "Protospacer Adjacent Motif (PAM) sequence" as used herein refers to a nucleic acid sequence present in the DNA target sequence but not in the guide polynucleotide sequence itself. For Cas9 to successfully bind to DNA, the target sequence in the genomic DNA must be complementary to the guide polynucleotide sequence and must be immediately followed by the correct protospacer adjacent motif or PAM sequence. Any DNA sequence with the correct target sequence followed by the PAM sequence will be bound by Cas9. A target sequence without the PAM following it is not sufficient for Cas9 to cut. Furthermore, the PAM sequence varies by the species of the bacteria from which the Cas9 was derived. The Type II CRISPR system derived from S. pyogenes, for example, has the PAM sequence NGG located on the immediate 3' end of a gRNA recognition sequence. Components (gRNA, Cas9) derived from different bacterial species will not function together. The CRISPR system requires that both the gRNA and Cas9 are expressed in the target cells, the respective promoters for Cas9 and gRNA expression determining the species specificity of a particular system.

The terms "recombinant DNA molecule", "recombinant construct", "expression construct", "construct", "construct", and "recombinant DNA construct" are used interchangeably herein. A recombinant construct comprises an artificial combination of nucleic acid fragments, e.g., regulatory and coding sequences that are not all found together in nature. For example, a construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) EMBO J. 4: 2411-2418; De Almeida et al., (1989) Mol. Gen. Genetics 218: 78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The term "RNA transcript" as used herein refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript pre mRNAt. "Messenger RNA" or "mRNA" refers to the RNA that is without introns and that can be translated into protein by the cell. "cDNA" refers to a DNA that is complementary to, and synthesized from, an mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107, 065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "regulatory sequences" as used herein refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation target sequences, RNA processing sites, effector binding sites, and stem-loop structures.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The terms "sequence identity" or "identity" in the context of nucleic acid or polypeptide sequences as used herein refer to the nucleic acid bases or amino acid residues in two sequences that are the same when aligned for maximum correspondence over a specified comparison window.

The term "stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or other DNA-containing organelle, of a host organism resulting in gene expression without integration or stable inheritance. Host organisms containing the transformed nucleic acid fragments are referred to as "transgenic" organisms.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na$^+$ ion, typically about 0.01 to 1.0 M Na$^+$ ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl) SDS (sodium dodecyl sulfate) at 37° C., and a wash in 1-2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C., and a wash in 0.1.times.SSC at 60 to 65° C.

The terms "subfragment that is functionally equivalent" and "functionally equivalent subfragment" are used interchangeably herein. These terms as used herein refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of genes to produce the desired phenotype in a transformed plant. genes can be designed for use in suppression by linking a nucleic acid fragment or subfragment thereof, whether or not it encodes an active enzyme, in the sense or antisense orientation relative to a plant promoter sequence.

The terms "target site", "target sequence", "target DNA", "target locus", "genomic target site", "genomic target sequence", and "genomic target locus" are used interchangeably herein and refer to a polynucleotide sequence in the genome (including choloroplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature. The terms "endogenous target sequence" and "native target sequence" are used interchangeably herein to refer to a target sequence that is endogenous or native to the genome of a plant and is at the endogenous or native position of that target sequence in the genome of the plant.

The target polynucleotide of a CRISPR complex can be any polynucleotide endogenous or exogenous to the eukaryotic cell and in the context of the present disclosure most advantageously a plant cell. For example, the target polynucleotide can be a polynucleotide residing in the nucleus of the plant cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence).

Target polynucleotides include a sequence associated with a signaling biochemical pathway, e.g., a signaling biochemical pathway-associated gene or polynucleotide. Examples of target polynucleotides can include a disease-associated gene or polynucleotide. In plants, a "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The term "targeted mutation" as used herein refers to a mutation in a native gene that was made by altering a target sequence within the native gene using a method involving a double-strand-break-inducing agent that is capable of inducing a double-strand break in the DNA of the target sequence as disclosed herein or known in the art.

The targeted mutation can be the result of a guide RNA/Cas endonuclease induced gene editing as described herein. The guide RNA/Cas endonuclease-induced targeted mutation can occur in a nucleotide sequence that is located within or outside a genomic target site that is recognized and cleaved by a Cas endonuclease.

The term "tracr mate sequence" may also be used interchangeably with the term "direct repeat(s)". In general, a "tracr mate sequence" includes any sequence that has sufficient complementarity with a tracr sequence to promote one or more of: (1) excision of a guide polynucleotide flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. The degree of complementarity between the tracr sequence and tracr mate sequence along the length of the shorter of the two when optimally aligned can be about or more than about 25%, 30%, 40%, 50%, 60%, 70%, 80%, 90%, 95%, 97.5%, 99%, or higher. The tracr sequence can be about or more than about 5, 6, 7, 8, 9, 10, 11, 12, 13, 14, 15, 16, 17, 18, 19, 20, 25, 30, 40, 50, or more nucleotides in length. The tracr sequence and tracr mate sequence can be contained within a single transcript, such that hybridization between the two produces a transcript having a secondary structure, such as a hairpin. Preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. The single transcript can further include a transcription termination sequence; preferably this is a polyT sequence, for example six T nucleotides.

The term "transformation cassette" refers to a specific vector containing a gene and having elements in addition to the gene that facilitates transformation of a particular host cell.

The term "translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner & Foster, (1995) *Mol. Biotechnol.* 3: 225-236).

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. The variable targeting domain can comprise a contiguous stretch of 12 to 30 nucleotides, most advantageously, but not exclusively, a contiguous stretch of about 20 nucleotides. The variable targeting domain can be composed of a DNA sequence, a RNA sequence, a modified DNA sequence, a modified RNA sequence, or any combination thereof.

The term "variant" as used herein refers to the exhibition of qualities that have a pattern that deviates from what occurs in nature.

The term "wild type" as used herein refers to the typical form of an organism, strain, gene or characteristic as it occurs in nature as distinguished from mutant or variant forms.

The practice of the present disclosure employs, unless otherwise indicated, conventional techniques of biochemistry, chemistry, molecular biology, microbiology, cell biology, genomics and recombinant DNA, which are within the skill of the art. See Sambrook et al., MOLECULAR CLONING: A LABORATORY MANUAL, 2nd edition (1989); CURRENT PROTOCOLS IN MOLECULAR BIOLOGY (Ausubel, et al. eds., (1987)); the series METHODS IN ENZYMOLOGY (Academic Press, Inc.): PCR 2: A PRACTICAL APPROACH (MacPherson et al., eds. (1995)), Harlow & Lane, eds. (1988) ANTIBODIES, A LABORATORY MANUAL, and ANIMAL CELL CULTURE (Freshney, ed. (1987)).

ABBREVIATIONS

CRISPR: Clustered Regularly Interspaced Short Palendromic Repeat (a region in bacterial genomes used in pathogen defense; crRNA: endogenous bacterial RNA that confers target specificity, requires tracrRNA to bind to Cas9; DSB: Double Strand Break; gRNA: guide RNA, a fusion of the crRNA and tracrRNA; gRNA sequence: 20 nucleotides that precede a PAM sequence in the genomic DNA; HDR: Homology Directed Repair; InDel: Insertion/Deletion; NHEJ: Non-Homologous End-Joining; ORF: Open Reading Frame; PAM: Protospacer Adjacent Motif;

DESCRIPTION

The present disclosure encompasses embodiments of a method for the targeted modification of a plant genome using a plant viral vector. The vector is used to deliver a nucleic acid to a plant cell encoding a guide polynucleotide, and in particular a guide RNA (gRNA), sequence complementary to a targeted region of the plant cell genome and a Protospacer Adjacent Motif (PAM). It is contemplated that the plant cell has also been genetically modified to express a Cas9 endonuclease, most advantageously by the prior formation of stable transgenically-modified plant cells. The combination of the gRNA-PAM and the expressed Cas9 endonuclease will generate a double-strand beak in the target genomic DNA. Upon repair of the break by the NHEJ mechanism, random nucleotide insertions or deletions (Indels) may occur at the repair site that may generate a mutation of the genomic sequence. While such mutations may result in an amino acid substitution at the break position, they may also generate a premature termination codon that results in an abnormally shortened expressed protein product.

Most particularly, but not exclusively, the present disclosure encompasses embodiments of a virus delivery system for delivering the elements of the CRISPR system to a plant cell or cells. Most advantageously, but not exclusively, a viral vector for use in the systems of the disclosure is a tobacco rattle virus (TRV).

The "CRISPR system" comprises transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide polynucleotide (also referred to as a "spacer" in the context of an endogenous CRISPR system), or other sequences and transcripts from a CRISPR locus. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., *J. Bacteriol.*, 169: 5429-5433; and Nakata et al., *J. Bacteriol.*, 171: 3553-3556), and associated genes. Similar interspersed SSRs have been identified in *Haloferax mediterranei, Streptococcus pyogenes, Anabaena,* and *Mycobacterium tuberculosis* (See, Groenen et al., *Mol. Microbiol.*, 10: 1057-1065; Hoe et al., *Emerg. Infect. Dis.* 5: 254-263; Masepohl et al., *Biochim. Biophys. Acta* 1307: 26-30; and Mojica et al., *Mol. Microbiol.*, 17:85-93).

The CRISPR loci typically differ from other SSRs by the structure of the repeats, which have been termed short regularly spaced repeats (SRSRs) (Janssen et al., *OMICS J. Integ. Biol.*, 6: 23-33; and Mojica et al., *Mol. Microbiol.*, 36: 244-246). In general, the repeats are short elements that occur in clusters that are regularly spaced by unique intervening sequences with a substantially constant length (Mojica et al., supra). Although the repeat sequences are highly conserved between strains, the number of interspersed repeats and the sequences of the spacer regions typically differ from strain to strain (van Embden et al., *J. Bacteriol.*, 182:2393-2401). CRISPR loci have been identified in more than 40 prokaryotes (See e.g., Jansen et al., Mol. Microbiol., 43:1565-1575) including, but not limited to *Aeropyrum, Pyrobaculum, Sulfolobus, Archaeoglobus, Halocarcula, Methanobacteriumn, Methanococcus, Methanosarcina, Methanopyrus, Pyrococcus, Picrophilus, Themoplasma, Corynebacterium, Mycobacterium, Streptomyces, Aquifex, Porphvromonas, Chlorobium, Thermus, Bacillus, Listeria, Staphylococcus, Clostridium, Thenrmoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema,* and *Thermotoga*.

One or more elements of a CRISPR system can be derived from a type I, type II, or type III CRISPR system. One or more elements of a CRISPR system can be derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide polynucleotide is designed to have complementarity, where hybridization between a target sequence and a guide polynucleotide promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. A target sequence is located in the nucleus or cytoplasm of a cell. The target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence". An exogenous template polynucleotide may be referred to as an editing template. The recombination can be homologous recombination.

Typically, in the context of a CRISPR system, formation of a CRISPR complex (comprising a guide polynucleotide hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide polynucleotide. The tracr sequence has sufficient complementarity to a tracr mate sequence to hybridize and participate in formation of a CRISPR complex. As with the target sequence, it is believed that complete complementarity is not needed, provided there is sufficient to be functional. The tracr sequence has at least 50%, 60%, 70%, 80%, 90%, 95% or 99% of sequence complementarity along the length of the tracr mate sequence when optimally aligned.

One or more vectors driving expression of one or more elements of a CRISPR system can be introduced into a host plant cell such that expression of the elements of the CRISPR system direct formation of a CRISPR complex at one or more target sites. For example, a Cas enzyme, a guide polynucleotide linked to a tracr-mate sequence, and a tracr sequence could each be operably linked to separate regulatory elements on separate nucleic acid vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream"

of) or 3' with respect to ("downstream" of) a second element. The coding sequence of one element may be located on the same or opposite strand of the coding sequence of a second element, and oriented in the same or opposite direction. A single promoter drives expression of a transcript encoding a CRISPR enzyme and one or more of the guide polynucleotide, tracr mate sequence (optionally operably linked to the guide polynucleotide), and a tracr sequence embedded within one or more intron sequences (e.g. each in a different intron, two or more in at least one intron, or all in a single intron). The CRISPR enzyme, guide polynucleotide, tracr mate sequence, and tracr sequence are operably linked to and expressed from the same promoter.

A vector according to the disclosure can comprise one or more insertion sites, such as a restriction endonuclease recognition sequence (also referred to as a "cloning site"). One or more insertion sites (e.g. about or more than about 1, 2, 3, 4, 5, 6, 7, 8, 9, 10, or more insertion sites) are located upstream and/or downstream of one or more sequence elements of one or more vectors. A vector comprises an insertion site upstream of a tracr mate sequence, and optionally downstream of a regulatory element operably linked to the tracr mate sequence, such that following insertion of a guide polynucleotide into the insertion site and upon expression the guide polynucleotide directs sequence-specific binding of a CRISPR complex to a target sequence in a eukaryotic cell. A vector comprises two or more insertion sites, each insertion site being located between two tracr mate sequences so as to allow insertion of a guide polynucleotide at each site. In such an arrangement, the two or more guide polynucleotides may comprise two or more copies of a single guide polynucleotide, two or more different guide polynucleotides, or combinations of these. When multiple different guide polynucleotides are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide polynucleotides. About or more than about 1, 2, 3, 4, 5, 6, 7, 8, 9, 10, or more such guide-sequence-containing vectors may be provided, and optionally delivered to a cell.

A vector can comprise a regulatory element operably linked to an enzyme-coding sequence encoding a CRISPR enzyme, such as a Cas protein. For example, the amino acid sequence of S. pyogenes Cas9 protein may be found in the SwissProt database under accession number Q99ZW2. The unmodified CRISPR enzyme has DNA cleavage activity, such as Cas9. The CRISPR enzyme can direct cleavage of one or both strands at the location of a target sequence, such as within the target sequence and/or within the complement of the target sequence. The CRISPR enzyme can direct cleavage of one or both strands within about 1, 2, 3, 4, 5, 6, 7, 8, 9, 10, 15, 20, 25, 50, 100, 200, 500, or more base pairs from the first or last nucleotide of a target sequence. A vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. A Cas9 nickase may be used in combination with guide sequenc(es), e.g., two guide polynucleotides, which target respectively sense and antisense strands of the DNA target. This combination allows both strands to be nicked and used to induce NHEJ. It is contemplated that sgRNAs targeted at the same location but to different strands of DNA) can induce mutagenic NHEJ. A single nickase (Cas9-D10A with a single sgRNA) is unable to induce NHEJ and create indels but double nickase (Cas9-D10A and two sgRNAs targeted to different strands at the same location) can do so in human embryonic stem cells (hESCs).

As a further example, two or more catalytic domains of Cas9 (RuvC I, RuvC II, and RuvC III) may be mutated to produce a mutated Cas9 substantially lacking all DNA cleavage activity. A D10A mutation can be combined with one or more of H840A, N854A, or N863A mutations to produce a Cas9 enzyme substantially lacking all DNA cleavage activity. A CRISPR enzyme can be considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than S. pyogenes, mutations in corresponding amino acids may be made to achieve similar effects.

An enzyme coding sequence encoding a CRISPR enzyme can be advantageously codon optimized for expression in particular cells, such as in plant cells. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence.

Various species exhibit particular bias for certain codons of a particular amino acid. Such codon usage differences are especially significant between groups of organisms such as between bacteria and plants. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura et al., (2000) *Nucl. Acids Res.* 28: 292. Computer algorithms for codon optimizing a particular sequence for expression in a particular host cell are also available, such as Gene Forge (Aptagen; Jacobus, Pa.), are also available. One or more codons (e.g. 1, 2, 3, 4, 5, 10, 15, 20, 25, 50, or more, or all codons) in a sequence encoding a CRISPR enzyme can correspond to the most frequently used codon for a particular amino acid.

A vector can further encode a CRISPR enzyme comprising one or more nuclear localization sequences (NLSs), such as about or more than about 1, 2, 3, 4, 5, 6, 7, 8, 9, 10, or more NLSs. The CRISPR enzyme can comprise about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. An NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Typically, an NLS consists of one or more short sequences of positively charged lysines or arginines exposed on the protein surface, but other types of NLS are known.

In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Examples of detectable markers include fluorescent proteins (such as Green fluorescent proteins, or GFP; RFP; CFP), and epitope tags (HA tag, flag tag, SNAP tag). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

A recombination template can be provided. A recombination template may be a component of another vector as described herein, contained in a separate vector, or provided as a separate polynucleotide. A recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. The template polynucleotide can be complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). When a template sequence and a polynucleotide comprising a target sequence are optimally aligned, the nearest nucleotide of the template polynucleotide can be within about 1, 5, 10, 15, 20, 25, 50, 75, 100, 200, 300, 400, 500, 1000, 5000, 10000, or more nucleotides from the target sequence.

The CRISPR enzyme can be part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) -galactosidase, -glucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

The present disclosure, therefore, provides methods comprising delivering one or more polynucleotides, such as or one or more vectors as described herein, one or more transcripts thereof, and/or one or proteins transcribed therefrom, to a host cell. In some aspects, the disclosure further provides cells produced by such methods, and plants comprising or produced from such cells. A CRISPR enzyme in combination with (and optionally complexed with) a guide polynucleotide can be delivered to a cell. Conventional viral and non-viral based gene transfer methods can be used to introduce nucleic acids in plant cells or most target tissues. TRV-based methods can be used to administer nucleic acids encoding components of a CRISPR system to cells in culture, or in a host organism. One or more vectors described herein can be used to produce a transgenic plant. Methods for producing transgenic plants and animals are known in the art, and generally begin with a method of cell transfection, such as described herein.

With recent advances in crop genomics, the ability to use CRISPR-Cas systems to perform efficient and cost effective gene editing and manipulation will allow the rapid selection and comparison of single and multiplexed genetic manipulations to transform such genomes for improved production and enhanced traits.

Guide polynucleotides and in particular gRNA molecules, determine specificity and direct the Cas9 endonuclease to genomic targets complementary to the 20 nucleotides preceding the NGG PAM sequence. Improving the methods for gRNA delivery into Cas9-overexpressing lines, therefore, is advantageous for an efficient and robust genome editing platform. Accordingly, a viral-mediated gRNA delivery system was developed that bypasses the requirement for transformation and/or regeneration of each user-defined target sequence, and in which editing efficiencies and applicability across plant species were significantly improved.

It is further contemplated that using the system and methods of the disclosure, a plant cell can receive a vector or vectors that encode more than one gRNA sequence, wherein the gRNA sequences specifically target different sites within the recipient cell's genome.

Most advantageously, it has been found that the desired target-specific gRNA nucleotide sequence, or a plurality of such sequences to multiple target sites in a plant genome, may be delivered to a plant cell by a recombinant viral vector such as, but not limited to, Tobacco Rattle Virus (TRV) that is engineered to comprise a heterologous gRNA-encoding nucleotide sequence. Such a viral vector may be delivered to an isolated plant cell or a cell in a tissue of a plant by direct delivery to such as a mechanically-generated wound in the surface of a leaf, to a plant vein, to a root, and the like by methods known in the art. Alternatively, it is contemplated that the recombinant viral vector(s) may be delivered to the plant cell or tissues by insertion of such vectors into a bacterial vector that can infect a plant system to deliver the viral vectors to Cas9-expressing plant cells.

In some particularly advantageous embodiments of the methods of the disclosure the gRNA-PAM encoding nucleic acid sequences may be inserted into the TRV-RNA2 genome of the Tobacco Rattle Virus (TRV). The recombinant TRV-RNA2 genome, or a plurality of such recombinant genomes (for targeting a plurality of sites of a plant genome), may be transformed into a bacterial vector delivery system such as, but not limited to, an *Agrobacterium tumefaciens*.

Methods for viral delivery of genome-engineering components have been established in mammalian cells using retroviruses and adenoviruses. In plants, tobacco rattle virus (TRV) has been widely used as an efficient vector for virus-induced gene silencing (VIGS) for functional genomics applications in plant species that it can infect (Ratcliff et al., (2001) *Plant J.* 25: 237-245). This virus is a member of the genus *Tobravirus*, which also includes pea early browning virus (PEBV) and pepper ring spot virus.

TRV, which has positive-sense single-stranded RNA, is a bipartite virus composed of distinct genomes RNA1 and RNA2. The RNA2 genome has been used as a vehicle to carry exonic gene fragments for post-transcriptional gene silencing (Dinesh-Kumar et al. (2003) *Meth. Mol. Biol.* 236: 287-294). Several viral vectors developed for VIGS applications are able to move systematically through the phloem in vascular tissues. The primary advantages of using TRV in VIGS applications include its mild symptoms, its ability to infect meristematic cells, and its wide range of host species. TRV has also been used to deliver a zinc finger nuclease (ZFN) to modify an integrated reporter gene in tobacco and petunia plants (Marton et al., (2010) *Plant Physiol* 154, 1079-1087).

To construct a viral-mediated genome editing system according to the disclosure, Cas9-over-expressing lines of *Nicotiana benthamiana* were generated. First, the human codon-optimized Cas9 sequence was optimized for in planta expression by generating the pK2GW7.Cas9 clone as shown in FIG. 3A. *Agrobacterium tumefaciens* was then used to transform tobacco leaf discs. The Cas9 clone was sequence verified, and its proper localization confirmed by transient expression of a GFP-fusion variant (encoded by pEARLYgate103.35S::Cas9:GFP) in tobacco leaves, as shown in FIG. 3B. In addition, the transgenic tobacco plants were analysed at the molecular level to determine the expression levels of the Cas9 transcript and protein, as shown in FIGS. 3C and 3D.

Next, a TRV RNA2 genome-derived vector was constructed and optimized for gRNA delivery. The TRV RNA2 constructs contained the gRNA nucleotide sequence under the control of either of two sequences: the *Arabidopsis thaliana* RNA polymerase III-transcribed U6 promoter (U6::gRNA) as a control, or the PEBV promoter (PEBV::gRNA) to permit the expression of the gRNA from the viral RNA-dependent RNA polymerase, as shown in FIG. 4A.

Figure 4B:
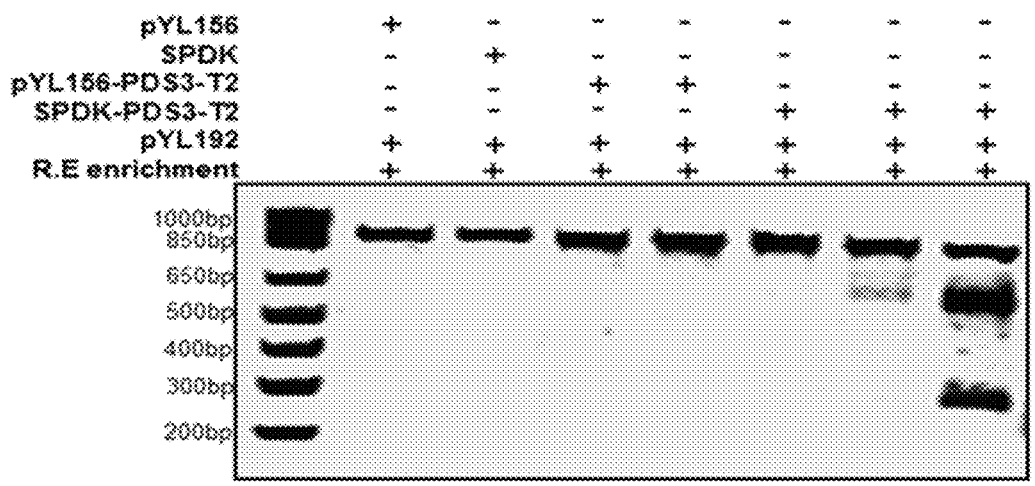
FIG. 4B illustrates T7E1-based NB.PDS3 mutation analysis on the PCR product from NcoI-enriched gDNA, two different RNA2 species, pYL156 with *Arabidopsis* U6:: sgRNA-PDS3 (Lanes 3 and 4) and SPDK with pEBV:: sgRNA-PDS3 (lanes 5, 6, and 7) were co-infiltrated with pYL192 to Cas9 expressing *N benthamiana*. Mutation was observed only in SPDK with pEBV::sgRNA (lane 5, 6, 7). Lanes 1 and 2 were vector controls.

As an embodiment of the system of the disclosure, the TRV virus was reconstituted in tobacco leaves by agroinfiltration of mixed *Agrobacterium* cultures that harbored the RNA1 genome (pYL192) in combination with the different RNA2 vectors. In these RNA2 vectors a gRNA with binding specificity for the phytoene desaturase (PDS) gene was driven by the negative-control promoter (pYL156.U6::PDS-.gRNA) or the PEBV promoter (pSPDK.PEBV::PDS-.gRNA) (FIG. 4A). Ten days post-infiltration, the presence of the TRV RNA1 and RNA2 genomes in both the inoculated and the systemic leaves was confirmed by RT-PCR, as shown in FIG. 4B.

Figure 5:
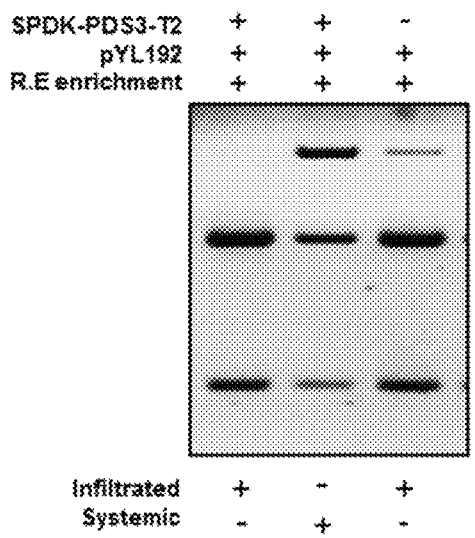
FIG. 5 illustrates detection of the systemic movement of TRV RNA1 and TRV RNA2 in inoculated leaves (Lanes 2 and 4) and in systemic leaves (Lanes 3 and 5). RT-PCR using TRV RNA1 with replicase-specific primers and TRV RNA2 with coat protein-specific primers were used. Control NB.Actin1-specific primers were used.
Figure 6:
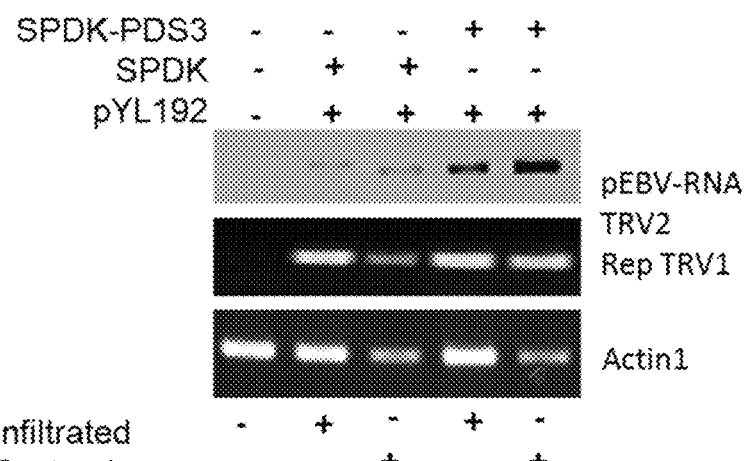
FIG. 6 illustrates the loss of restriction enzyme NcoI site assay. PCR product from NcoI enriched gDNA were subjected to NcoI digestion. Infiltrated and systemic leaf samples showed the NcoI resistant upper band (Lanes 2 and 3). Lane 1 is wild type control.
Figure 7:
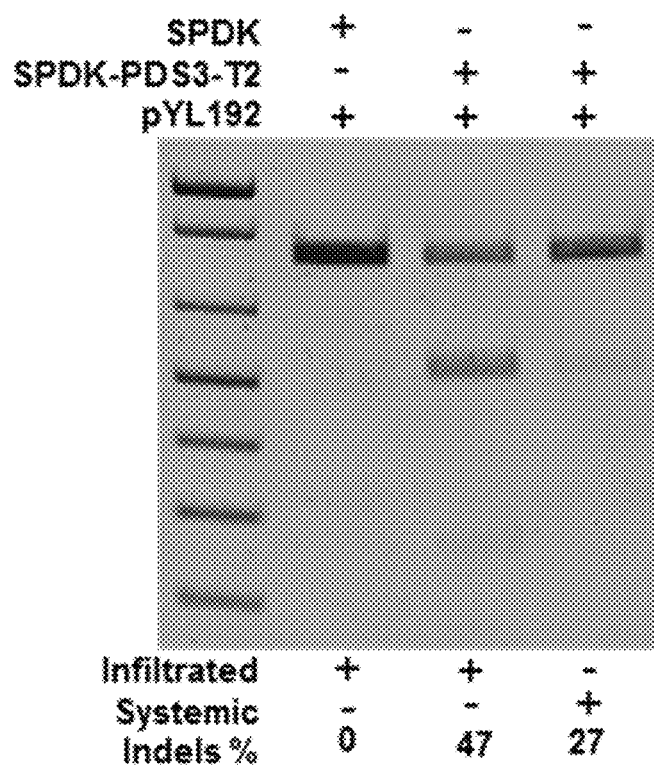
FIG. 7 illustrates the ratio of TRV-based CRISPR/Cas9 mutation. PCR product from non-enriched gDNA was subjected to T7E1 digestion, both from infiltrated and systemic leaves. Mutation percentage was calculated using ImagJ software.
Figure 8:
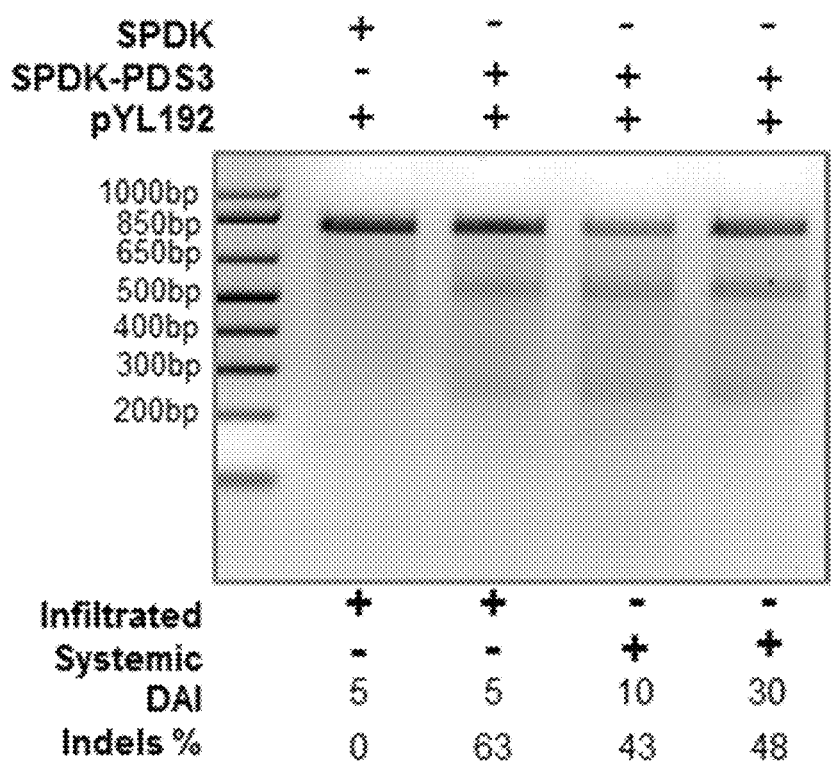
FIG. 8 illustrates systemic mutation analysis. gDNA was extracted from infiltrated leaves, 10DAI system leaves and 30DAI leaves and enriched with NcoI. The PCR product was subjected to T7E1 assay for mutation analysis.
Figure 9:
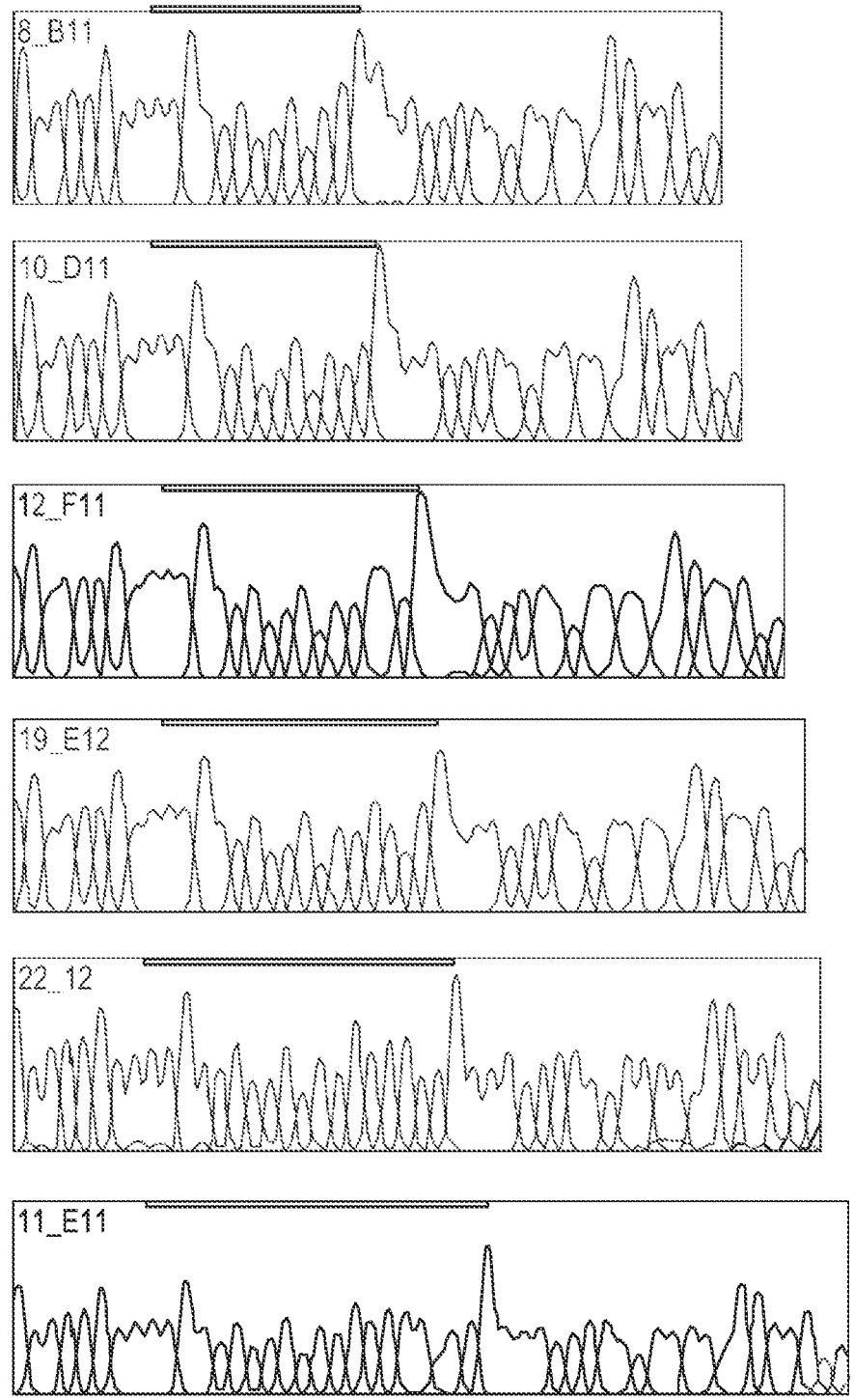
FIG. 9 illustrates chromatograms of the representative sequenced indels from infiltrated leaves for PDS3 (SEQ ID NO: 124-129). Black line highlights the target region in the PDS3 gene.
Figure 10:
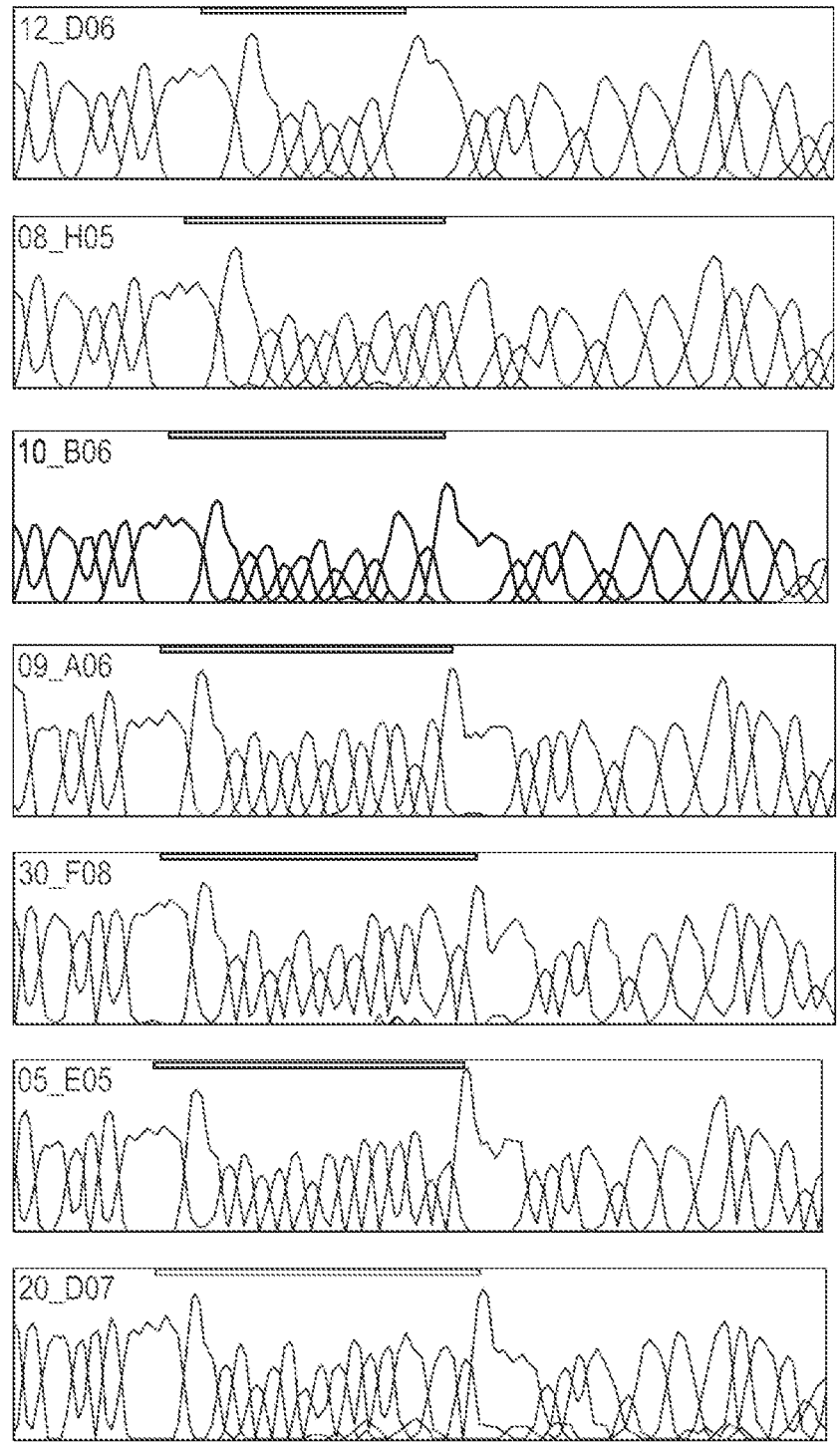
FIG. 10 illustrates chromatograms of the representative sequenced indels from systemic leaves for PDS3 (SEQ ID NO: 130-136). Black line highlights the target region in the PDS3 gene.
Figure 11:
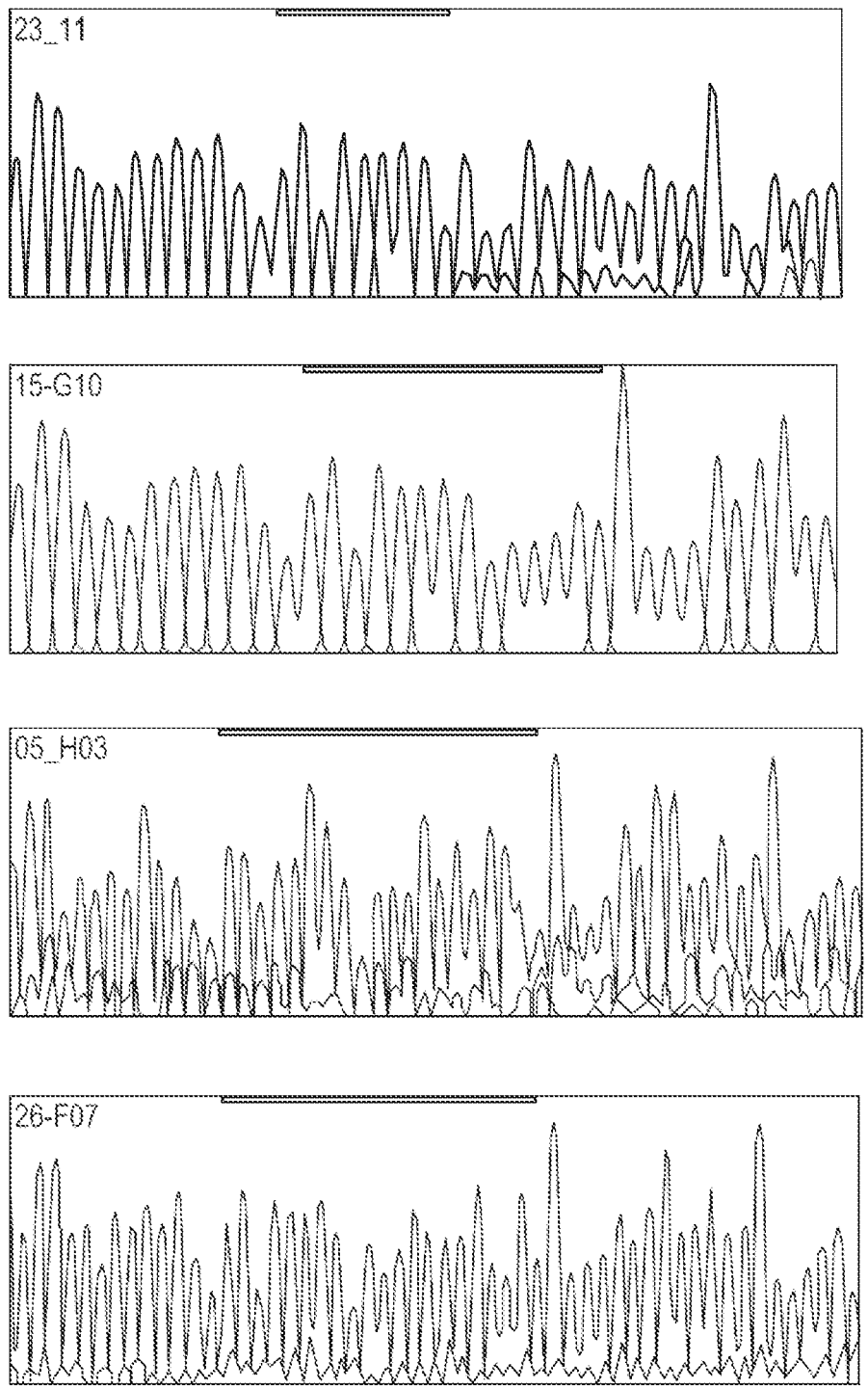
FIG. 11 illustrates chromatograms of the representative sequenced indels for PCNA gene (SEQ ID NO: 138-141). Black line highlights the target region in the PCNA gene.
Figure 13:
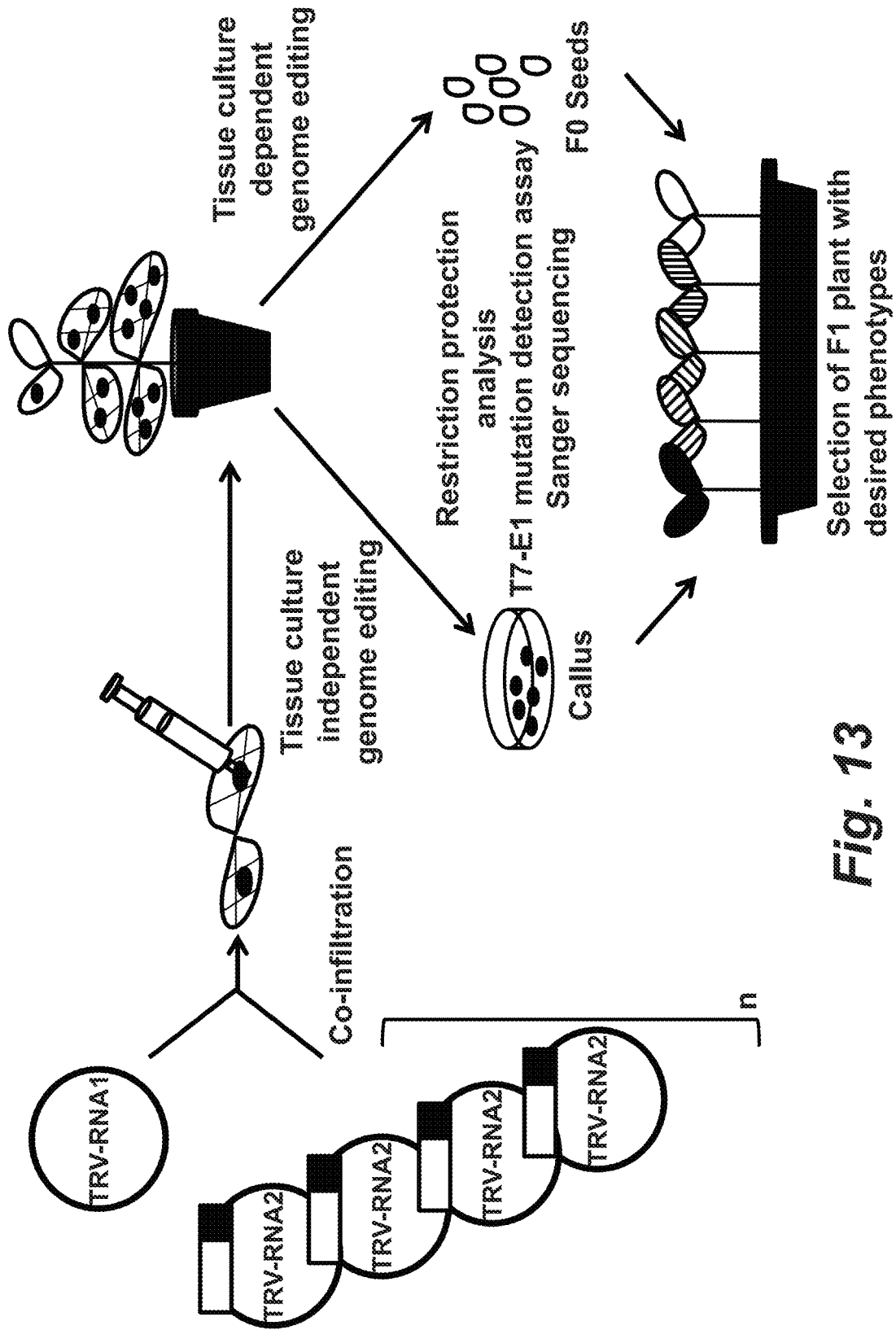
FIG. 13 illustrates a flow sheet of TRV-based targeted genome editing. TRV RNA1 and TRV RNA2 with the targeted sgRNA are mixed in equal volumes to be delivered to a lower leaf of Cas9-expressing plants. Through systemic infection, TRV moves to other regions of the plant, including meristimatic tissues. Leaves can be directly converted to callus and plantlets through tissue culturing or seed from the inoculated plant can be collected for mutation analysis and functional genomics. For multiplexing (multiple independent locus mutations at the same time), sgRNAs can be ligated individually to RNA2 vector and then mixed together and co-infiltrated with RNA1.
Figure 23:
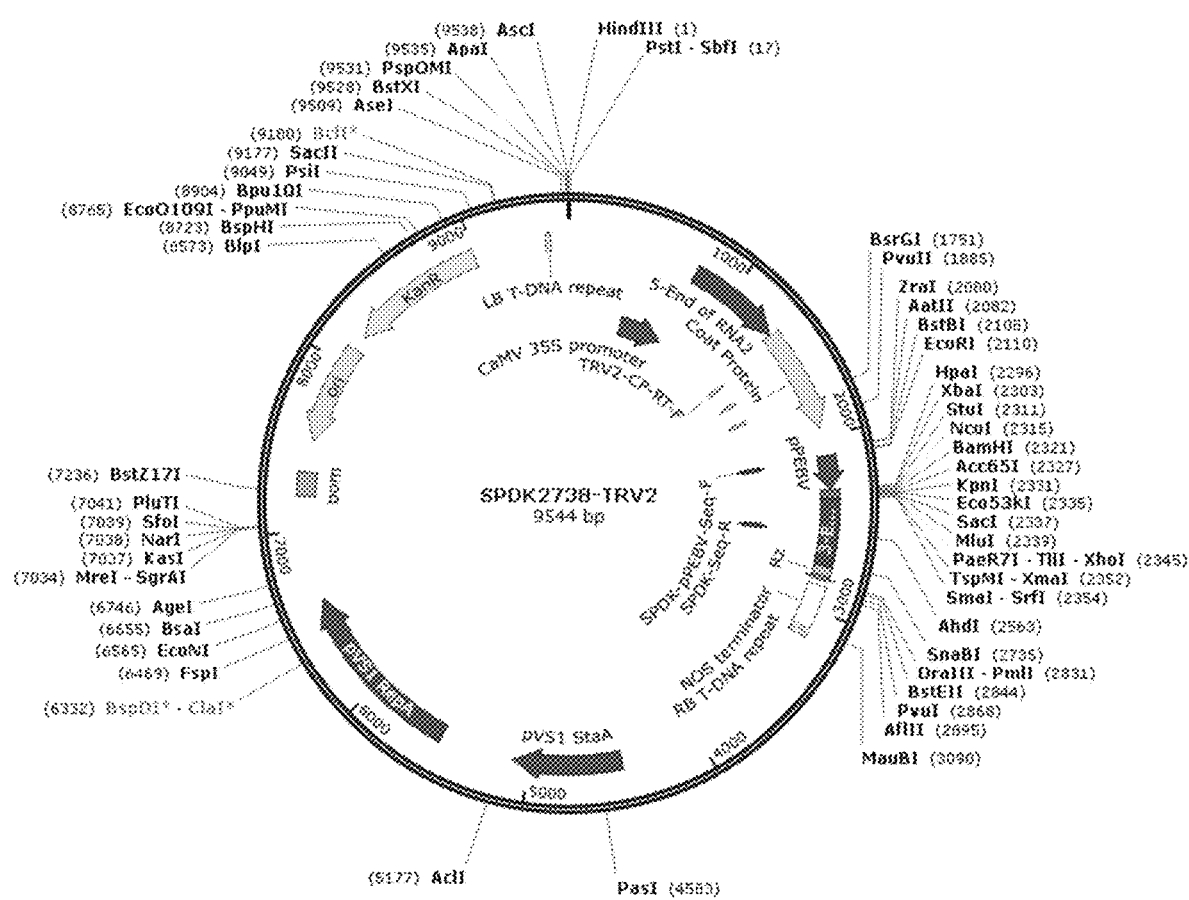
FIG. 23 illustrates the map of SPDK2738-TRV2. Locations of restriction sites are indicated.
Figure 25:
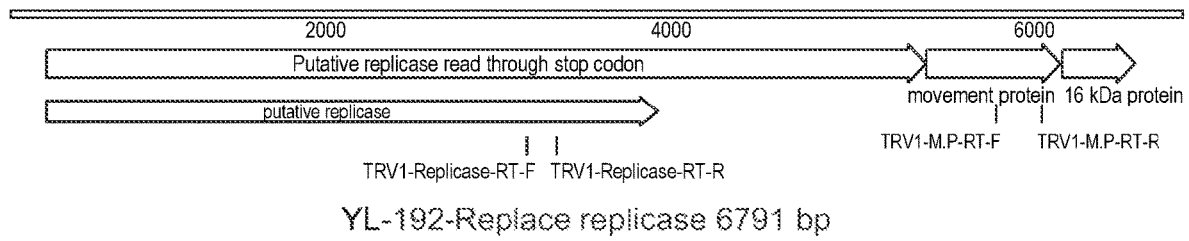
FIG. 25 illustrates the map of YL192.
Figure 26:
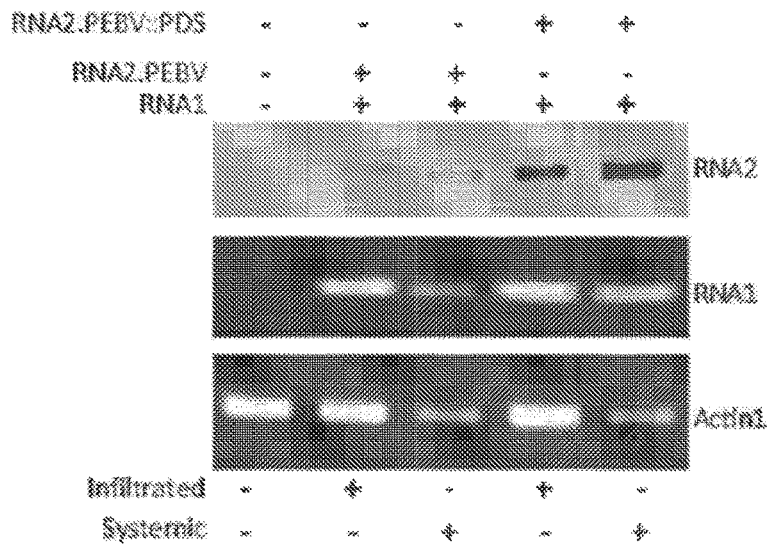
FIG. 26 illustrates systemic movement of TRV RNA1 and RNA2 using RT-PCR analysis. RNA1 with replicase specific primers and RNA2 with coat protein specific primer in inoculated leaf (Lane 2, 4), and in systemic leaf (Lane 3, 5). For RT-PCR control NbActin1-specific primers (SEQ ID NO: 13 and 14) were used.
Figure 27:
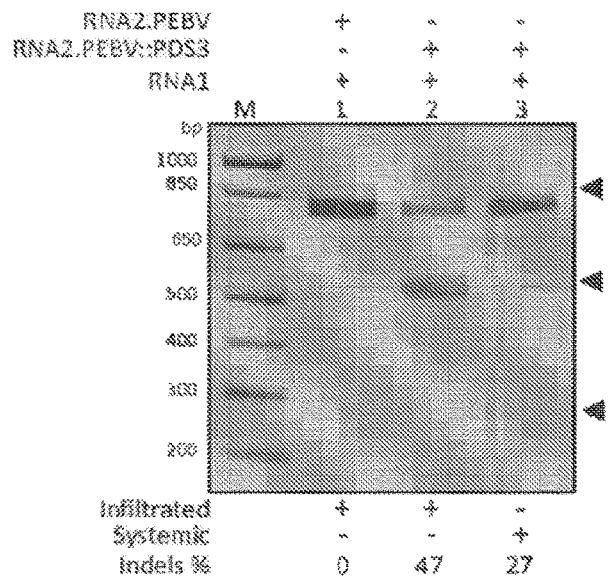
FIG. 27 illustrates the efficiency of TRV-based mutagenesis using CRISPR/Cas9. PCR products amplified from genomic DNA were subjected directly to T7E1 digestion, both from infiltrated and systemic leaves. Mutation efficiencies (in percentage) were calculated using ImagJ software.
Figure 30:
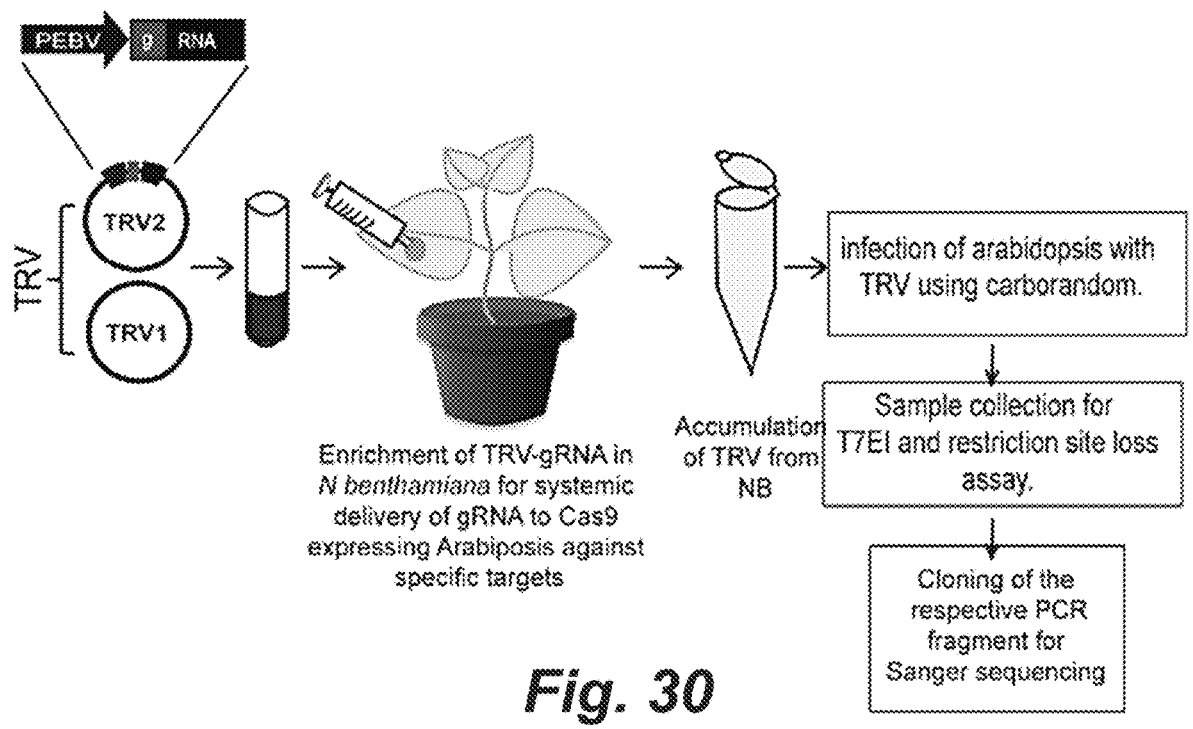
FIG. 30 schematically illustrates the enrichment of TRV (containing gRNA for AtGI1, AtADH1, and AtTT4) in *Nicotiana benthamiana* and inoculation of Cas9-GFP expressing *Arabidopsis* plants with the enriched TRV sap.
Figure 31:
FIG. 31 is a digital image confirming that TRV-VIGS silences AtPDS in whole plants (Leaves, Stem, Siliques).

Assays were then performed for genomic editing of the target sequence in both inoculated and systemic leaves using the surveyor and T7E1 nucleases and restriction-protection analysis (FIG. 5). Significant levels of editing in both assays were detected (FIG. 6). In both types of leaves, editing efficiencies were higher than those reported in previous studies (FIG. 7). Furthermore, to corroborate the T7E1 and restriction-protection assays, the target sequence from both inoculated and systemic leaves was PCR-cloned. Thirty of the resultant clones were then subjected to Sanger sequencing analysis (FIGS. 9 and 10). The sequencing analyses confirmed the results of the T7E1 and restriction-protection assays, and demonstrated that modification ratios were high: indels were present in 17 clones derived from inoculated leaves and in 9 clones from systemic leaves.

Figures 2A, 2B:
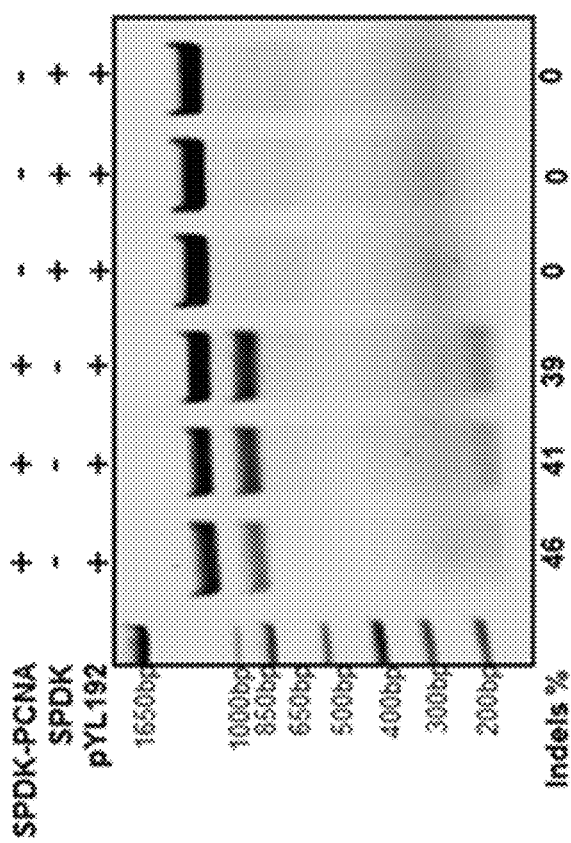

To further validate the functioning of systems of the disclosure, a gRNA molecule was designed and constructed that targeted the Proliferating Cell Nuclear Antigen (PCNA) gene. Using this construct, targeted modifications in the PCNA gene were achieved in both inoculated and systemic leaves, as demonstrated by T7E1 assays, as shown in FIG. 2A. The PCR amplicons were subcloned, and sequencing confirmed the presence of sequence modifications (FIG. 2B).

One of the primary advantages of the methods of viral-mediated delivery of gRNA molecules according to the disclosure is its amenability to multiplexing. To determine whether multiplexed genome editing was possible in the editing platform of the disclosure, gRNA molecules targeting both PCNA and PDS were co-delivered by mixing *Agrobacterium tumefaciens* bacterial cultures harboring the RNA2 vector clones pSPDK.PEBV::PCNA.gRNAs or pSPDK.PEBV::PDS.gRNAs with specificities for PDS and PCNA, respectively. Two weeks post-infiltration, genomic modifications at the intended targets were assayed. Modifications were present at both of the intended targets, as shown in FIG. 2C, although efficiencies were lower when more than one gRNA was used simultaneously.

A primary concern in applications of CRISPR/Cas9 genome editing is off-target activity. Although this issue is less important in plants than in genetic medicine, the extent of off-target activities by the systems of the disclosure were assessed. To identify candidate unintended targets of genome editing, the draft genome of *Nicotiana benthamiana* was screened for imperfect matches (i.e., allowing several mismatches) to a 20-nucleotide gRNA sequence (see Example 8, Table 2). These candidates were then subjected to T7E1 and restriction-protection assays. Consistent with previous reports (Nekrasov et al., (2013) *Nature Biotechnol.* 31: 691-693; Feng et al., (2014) *Proc. Natl. Acad. Sci. U.S.A.* 111: 4632-4637), no genomic modifications were detected at any of the predicted unintended targets, as shown in FIGS. 12A and 12B. Therefore, it was concluded that either the system exhibited no off-target activities, or that any such activities occurred at levels too low to be detected by the modification-detection assays employed.

It is to be understood that the viral-mediated genome editing platform of the disclosure is not to be limited to vectors derived from TRV; other RNA viruses (e.g., but not limited to, Tobacco Mosaic Virus (TMV) and Potato Virus X). Furthermore, it is contemplated that the systems and methods of the disclosure can be used to deliver gRNA molecules to various plant species. While *Nicotiana* and *Arabidopsis* have been used as useful experimental products, it is to be understood that any plant species or strain that can be genetically modified to express heterologous Cas9 endonuclease and can be infected or receive a target-specific gRNA, may be genetically modified by the methods of the disclosure.

For genome editing purposes, TRV is most advantageous as a vehicle for gRNA delivery to all plant parts, including meristems. The ability of the virus to infect growing points can lead to modification of the germline cells and eventually to seeds with the desired modifications, obviating the need for tissue culture and transformation. In addition, this system can be applied to transcriptional gene silencing by delivering gRNAs that target promoter regions into plants overexpressing a catalytically inactive Cas9 endonuclease.

Accordingly, the viral-mediated genome editing systems of the disclosure meet several requirements for efficient and multiplexed editing: 1) TRV, for example, can systematically infect a large number of plant species, both naturally and under laboratory conditions; 2) the virus can be introduced into plants via *Agrobacterium* and delivered into growing points of the plant; 3) the small genome size of TRV facilitates cloning, multiplexing, library constructions, and agroinfections; and 4) the viral RNA genome does not integrate into plant genomes. Furthermore, it is advantageous to use this system to confer viral interference, thereby protecting plants against DNA viruses. In conclusion, the methods of the disclosure expand the utility of the CRISPR/Cas9 system and are useful for bioengineering in functional genomics and agricultural biotechnology applications.

The disclosure further provides kits containing any one or more of the elements disclosed in the above methods and compositions. The kit can comprise a vector system and instructions for using the kit. The vector system can comprise (a) a first regulatory element that can be operably linked to a tracr mate sequence and one or more insertion sites for inserting a guide polynucleotide upstream of the tracr mate sequence, wherein when expressed, the guide polynucleotide directs sequence-specific binding of a CRISPR complex to a target sequence in a eukaryotic cell, wherein the CRISPR complex comprises a CRISPR enzyme complexed with (1) the guide polynucleotide that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. Elements may be provide individually or in combinations, and may be provided in any suitable container, such as a vial, a bottle, or a tube. The kit can include instructions in one or more languages, for example in more than one language.

A kit can comprise one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. The buffer can be alkaline. The buffer has a pH from about 7 to about 10. The kit can comprise one or more oligonucleotides corresponding to a guide polynucleotide for insertion into a vector so as to operably link the guide polynucleotide and a regulatory element. The kit can comprise a homologous recombination template polynucleotide.

One aspect of the disclosure encompasses embodiments of a method for modifying a target site in the genome of a plant cell, the method comprising providing a nucleic acid sequence encoding a guide RNA-PAM to a plant cell having a Cas endonuclease, wherein the guide RNA is delivered to the plant cell by a plant virus vector, and wherein said guide RNA and Cas endonuclease are capable of forming a complex that enables the Cas endonuclease to introduce a double strand break at said target site.

In some embodiments of this aspect of the disclosure, the method can further comprise providing to the plant cell a heterologous donor DNA, wherein said heterologous donor DNA can comprise a polynucleotide of interest desired to be incorporated into the genome of the plant cell.

In some embodiments of this aspect of the disclosure, the method can further comprise identifying at least one plant cell that has a modification at said target, wherein the modification includes at least one deletion or substitution of one or more nucleotides in said target site.

In some embodiments of this aspect of the disclosure, the plant virus vector can be a genome of the Tobacco Rattle Virus (TRV).

In some embodiments of this aspect of the disclosure, the nucleic acid sequence encoding a guide RNA-PAM can be inserted into the TRV-RNA2 genome of the TRV-derived vector.

In some embodiments of this aspect of the disclosure, the plant cell can be a genetically modified plant cell comprising a heterologous nucleic acid encoding a Cas9 endonuclease operably linked to a promoter.

In some embodiments of this aspect of the disclosure, the plant cell can be a stable transgenic variant comprising a heterologous nucleic acid encoding a Cas9 endonuclease operably linked to a promoter.

In some embodiments of this aspect of the disclosure, the heterologous nucleic acid encoding the Cas endonuclease gene can be a plant optimized nucleic acid sequence.

In some embodiments of this aspect of the disclosure, the plant cell can be in a tissue of a plant and the recombinant viral vector can be delivered to the plant cell by infecting the plant with the bacterial vector, by systemically delivering the viral vector, or by mechanical injury to a surface of the plant.

In some embodiments of this aspect of the disclosure, the bacterial vector can be an *Agrobacterium tumefaciens*.

In some embodiments of this aspect of the disclosure, the plant cell can be an isolated plant cell and wherein the method further comprises culturing said plant cell to generate a plant seedling or a mature plant.

In some embodiments of this aspect of the disclosure, the method can further comprise targeting a plurality of target sites in the same recipient plant cell or cells, wherein step (a) of said method comprises delivering to the plant cell expressing a Cas9 endonuclease a plurality of recombinant viral vectors, wherein said viral vectors each independently comprises a nucleic acid sequence encoding a guide RNA-PAM complementary to a targeted region of the plant cell genome and a Protospacer Adjacent Motif (PAM), and wherein each member of the plurality of recombinant viral vectors comprises a gRNA-PAM sequence not found in the other recombinant viral vectors delivered to the plant cell.

Another aspect of the of this aspect disclosure encompasses embodiments of a method for modifying a target site in the genome of a plant cell, the method comprising providing a nucleic acid sequence encoding a guide RNA-PAM to a plant cell having a Cas endonuclease, and optionally a polynucleotide modification template, wherein the guide RNA, and optionally the polynucleotide modification template, is delivered to the plant cell by a plant virus vector, and wherein said guide RNA and Cas endonuclease can be capable of forming a complex that enables the Cas endonuclease to introduce a double strand break at said target site, and wherein said polynucleotide modification template comprises at least one nucleotide modification of said target site.

In some embodiments of this aspect of the methods of the disclosure, the target site in the genome of a cell can be selected from the group consisting of a promoter sequence, a terminator sequence, a regulatory element sequence, a splice site, a coding sequence, a polyubiquitination site, an intron site, and an intron enhancing motif.

Another aspect of the disclosure encompasses embodiments of a recombinant nucleic acid construct comprising a plant virus vector comprising a promoter operably linked to a nucleic acid sequence encoding a guide RNA-PAM, wherein said guide RNA can be capable of forming a complex with a plant optimized Cas9 endonuclease, and wherein said complex is capable of binding to and creating a double strand break in a genomic target sequence said plant genome.

In some embodiments of this aspect of the disclosure, the plant virus vector is a genome of the Tobacco Rattle Virus (TRV).

In some embodiments of this aspect of the disclosure, the nucleic acid sequence encoding a guide RNA-PAM can be inserted into the TRV-RNA2 genome of the TRV-derived vector.

Another aspect of the disclosure encompasses embodiments of a genetically modified plant, or a progeny thereof, generated by a method for modifying a target site in the genome of a plant cell, the method comprising genetically modifying plant cell or cells or cells having a Cas endonuclease by providing to said cell or cells a recombinant nucleic acid construct comprising a nucleic acid sequence encoding a guide RNA-PAM, and optionally a polynucleotide modification template, wherein the guide RNA-PAM, and optionally the polynucleotide modification template, is delivered to the plant cell or cells by a plant virus vector, and wherein said guide RNA-PAM and Cas endonuclease are capable of forming a complex that enables the Cas endonuclease to introduce a double strand break at said target site, and wherein said polynucleotide modification template comprises at least one nucleotide modification of said target site; culturing the genetically modifying plant cell or cells or cells to generate a plant embryo or mature plant; and optionally generating progeny from said embryo or mature plant.

In some embodiments of this aspect of the disclosure, the plant virus vector can be a genome of the Tobacco Rattle Virus (TRV).

In some embodiments of this aspect of the disclosure, the nucleic acid sequence encoding a guide RNA-PAM is inserted into the TRV-RNA2 genome of the TRV-derived vector.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

The meaning of abbreviations is as follows: "sec" means second(s), "min" means minute(s), "h" means hour(s), "d" means day(s), "$\mu$L" means microliter(s), "mL" means milliliter(s), "L" means liter(s), "$\mu$M" means micromolar, "mM" means millimolar, "M" means molar, "mmol" means millimole(s), "$\mu$mole" mean micromole(s), "g" means gram(s), "$\mu$g" means microgram(s), "ng" means nanogram(s), "U" means unit(s), "bp" means base pair(s) and "kb" means kilobase(s).

EXAMPLE

Example 1

Vector Construction

To generate a Cas9 overexpressing line of *Nicotiana benthamiana*, a recombinant 35S::Cas9 (SEQ ID NO: 1) in a pK2GW7 binary vector was constructed. The complete 3XFlag-NLS-Cas9-NLS (SEQ ID NO: 1) cassette was PCR amplified with the Cas9-GW-Fw (SEQ ID NO: 10) and Cas9-Rev (SEQ ID NO: 3) primers using pX330 plasmid as the template. The purified PCR product was cloned into pENTR/D-TOPO (Life Technologies). Restriction digestion and Sanger sequencing were used to confirm the pENTR/Cas9 clones, which were subsequently cloned into the pK2GVV7 destination vector for in planta expression using the Gateway LR® clonase (Life Technologies).

To generate the Cas9 C-terminus fusion to the GFP reporter, the Cas9 3' stop codon was removed by PCR amplification using primers Cas9-GW-Fw (SEQ ID NO: 10) and Cas9-Rev-No-Stop (SEQ ID NO: 12) and sequencing confirmed clone pENTR/Cas9dStop for Gateway LR recombination reaction into pEARLY-GATE103. The pENTR/Cas9dStop clone was first linearized with the MluI enzyme and used for the recombination reaction to generate pEARLY-GATE103.Cas9:GFP. Sanger sequencing was used to confirm the sequence authenticity of clones and the translational fusions.

The gRNA clones were custom synthesized in pUC19 (–MCS) plasmid using BlueHeronBio gene synthesis service (BlueHeronBio, Bothell, Wash. USA). Each gRNA was flanked by XbaI and XmaI restriction sites and included a 116 bp fragment that contained a 20 bp nucleotide target sequence, 84 bp functioning as a Cas9-binding loop followed by seven T nucleotides for transcriptional termination. The 116 bp gRNA fragment of each target was subcloned into the TRV2 (RNA2) vector by restriction ligation cloning using with XbaI and XmaI restriction enzymes.

Example 2

Tobacco *Agrobacterium*-Mediated Transformation

The pK2GW7.Cas9 T-DNA binary vector was introduced into *Agrobacterium tumefaciens* strain GV310 using electroporation. Single colonies carrying the T-DNA vector were grown overnight at 28° C. in 5 mL LB medium containing 100 mg/L spectinomycin, 50 mg/L gentamycin and 25 mg/L rifampicin. The overnight culture was used to inoculate 50 mL LB containing the selective antibiotics and 5 mM MES. Cells were collected at $OD_{600}$ of 1.0 and pelleted, suspended and diluted to an $OD_{600}$ of 0.2 in transformation medium (liquid ½ MS salts, 150 mM acetosyringone, pH 5.8). Re-suspended cells were kept at ambient temperature for 4 hours and applied to forceps-wounded 1-2 cm leaf discs from 4-6 weeks aseptically grown tobacco plants. The Agrobacterium was co-cultured with leaf discs. After 36 hr, leaf discs were placed inverted on selection media containing 500 mg/L and 50 mg/L kanamycin. Leaf discs were plated onto MS regeneration and selection medium (4.4 g MS salts with vitamins, 1 mg/L BA, 0.1 mg/L NAA, 30 g sucrose, pH 5.8 and supplemented with 50 mg/L kanamycin and timentin 200 mg/L. Shoot tissues appeared after 3- to 4 weeks and were excised and placed into root-inducing medium. Small plantlets were removed and acclimated into soil, molecularly characterized for the presence of the transgene and seeds were collected from the plants and confirmed at the molecular level to carry the transgene.

Example 3

Agroinfiltration of Cas9 Over-Expressing Tobacco Plants

Two Cas9 over-expressing tobacco lines (B14-2, and B14-4) were selected for agroinfiltration experiments. TRV1 and TRV2 T-DNA vectors were introduced separately into Agrobacterium tumefaciens GV3101 strain. Transformed single colonies were grown overnight in selective medium and resuspended and diluted to an $OD_{600}$ of about 0.3 into infiltration medium (10 mM MES, 10 mM $CaCl_2$ pH 5.7, 200 µM Acetosyringone). The Agrobacterium cultures were kept at ambient temperature for four hours in the infiltration medium to increase their transformation competency. For co-infiltration using Agrobacteria harboring TRV1 and TRV2, agrobacterium cultures were mixed at 1:1 ratio (vol/vol). Agrobacteria were infiltrated into the lower side of the 3 to 4 weeks old leaves using a needleless 2 mL syringe. Samples were collected after 5, 10, and 30 days post-infiltration and used for targeted genome modification analysis.

Example 4

RT-PCR-Based Detection of TRV and gRNA Molecules

Total RNA (1 µg) was extracted from the systemic leaves after 5, 10, and 25 days post-infiltration using RNAeasy mini kit (Invitrogen). To remove DNA impurities, RNA was treated with DNaseI (Invitrogen). First strand cDNA was synthesized using SuperScript III reverse transcriptase (Invitrogen) using primers TRV1-MP-RT-R (SEQ ID NO: 18) and SPDK-SEQ-R (SEQ ID NO: 20) for TRV1 and TRV2, respectively. TRV.repF (SEQ ID NO: 17) and TRV.repR (SEQ ID NO: 20) primers were used to amplify 194 bp of the TRV replicase gene. The pPEBVF and SPDK-SEQ-R primers were used to amplify the 116 bp fragment of the gRNA. The Nicotiana benthamiana actin gene (Genbank accession number AY179605) was used as internal control and for data normalization.

Example 5

Detection of Cas9-Mediated Mutations Via T7E1 or Restriction Enzyme Protection Assays Tobacco leaves were collected after 5, 10, and 30 days post-infiltration and genomic DNA was extracted using DNA extraction buffer (100 mM Tris-Cl, 1 mM EDTA, 100 mM NaCl, 100 mM LiCl, 100 mM B-mercaptoethanol, 0.4% RNase) and PCI (Phenol:Chloroform:Isoamyl alcohol)

For T7E1 mutation detection assay in the PDS genomic target, the NB-PDS-TR12-F (SEQ ID NO: 21) and NB-PDS-TR12-R (SEQ ID NO: 22) primers were used to PCR amplify a 797 bp fragment containing the target sequence for modification. PCR reactions were either performed using genomic DNA directly or using genomic DNA enriched for the modification. The target sequence contained NcoI restriction site genomic DNA was enriched with NcoI (New England Biolab) and used as the template for PCR. This PCR product was used for T7E1 and for cloning and Sanger sequencing to confirm the genomic modification in the gene target sequence.

The gel-purified (200 ng) PCR product enriched NcoI genomic DNA was denatured and re-annealed in NEB Buffer 2 in the PCR cycler to allow for hetero-duplex formation using a cycling program (95° C. for 10 min, 85° C. for 2 min, 75° C. for 3 min, 65° C. for 3 min, 55° C. for 3 min, 45° C. for 3 min, 35° C. for 3 min, 25° C. for 3 min, 4° C.). The PCR product was subjected to mutation detection assays using T7E1. A T7E1 assay was also performed on PCR products from non-enriched gDNA as template for PDS3 and PCNA for mutation detection analysis.

Example 6

Identification of Potential Off-Target Loci in the Nicotiana benthamiana Genome

To screen for potential off-target sites, a combinatorics approach was applied to identify all potential binding gRNA sequences that would carry from 1 to 7 mutations at any nucleotide position in the gRNA sequence. These potential binding sites were identified in the genome of N. benthamiana (Table 1).

TABLE 1

| (PDS3) gRNA putative off-targets binding sites | | | |
|---|---|---|---|
| Number of mismatches | Total combinations of gRNAs | Total hits | Total hits with NcoI |
| 1 | 60 | 0 | 0 |
| 2 | 1,710 | 0 | 0 |
| 3 | 30,780 | 0 | 0 |
| 4 | 392,444 | 1 | 0 |
| 5 | 3,767,412 | 60 | 4 |
| 6 | 28,255,525 | 515 | 46 |
| 7 | 169,532,551 | 3,689 | 275 |

The putative off-target binding sites were subjected to further annotation where sequences were split into two groups of conserved and not conserved NcoI restriction sites directly preceding the Protospacer Adjacent Motif (PAM)

sequence and sites containing mutation in seed and non-seed sequence.

Sequences surrounding the putative off-target sites and designed primers around them were extracted. PRIMER3® used software to facilitate the high-throughput design and selection of primers. PCR was performed for all the selected 48 off-target sites. Out of 48 different primer pairs for off-targets, 28 gave specific single band amplification. All single band PCR products were treated with T7E1 as described above.

Example 7

Calculation of Modification Frequencies

For mutation rate determination, PCR products derived from PDS3 and PCNA genes from the non-enriched genomic DNA were treated with T7E1 and used for analysis. Mutation rates were estimated by using IMAGJ® software.

Example 8

TABLE 2

| SEQ ID NO: | PRIMER NAME | SEQUENCE (5'-3') | Usage |
|---|---|---|---|
| 10 | Cas9-gw-Fw | CACCATGGACTATAAGGACCACG | clone cas9 |
| 11 | Cas9-Rev-Stop | TTACTTTTTCTTTTTTGCCTGGC | clone Cas9 |
| 12 | Cas9-Rev-No-Stop | CTTTTTCTTTTTTGCCTGGC | Cas9-GFP |
| 13 | NB-ACTIN1-RT-F | TGAAGATCCTCACAGAGCGTGG | Rt-pcr normalization control |
| 14 | NB-ACTIN1QRT-LIU-R | TTGTATGTGGTCTCGTGGATTC | |
| 15 | CAS9-SEQ-F6 | GCCCTCCAAATATGTGACTTCC | Cas9 expression confirmation |
| 16 | CAS9-REV-STOP | TTACTTTTTCTTTTTTGCCTGGC | |
| 17 | TRV1-RELICASE-RT-F | CTACTGGGAGAGCAGCAACC | Detection of trv-rna1 systemic movement |
| 18 | TRV1-REPLICASE-RT-R | CTGAGCGCAAAAGTACACCA | |
| 19 | SPDK-PEBVS/SEQF | CGAATTCGAGCATCTTGTTCTGGGGTTTCA | Detection of trv-rna2 gRNA part systemic movement |
| 20 | SPDK-SEQ-R | CTATGGTAAGACAATGAGTCGGCCAAACGC | |
| 21 | NB-PDS3-TR12-GDNA-F2 | GAAACACATCACCTAGGCGG | PCR around pds target |
| 22 | NB-PDS3-TR12-GDNA-R | GGGCGTGAGGAAGTACGAAA | |
| 23 | NBPDS3-gDNA-404bp-F | GTAAAATGCCCCAAATTGGACTTGT | Amplify 404 bp around pds |
| 24 | NBPDS3-gDNA-404bp-R | CGTGAGGAAGTACGAAATGATGATGA | Amplify 404 bp around pds |
| 25 | NB.PCNA gDNA F1 | CCTAACCCTAATTTCCCCAG | PCR around pcna target |
| 26 | NB.PCNA gDNA R1 | TCACTGTCAATGTCCATCAG | |
| | 4 MISMATCHES | | |
| 27 | 307528-16-F | AAATTGGATCTTGGATCACTCAAGC | Nb-pds3-2 off target |
| 28 | 307528-16-R | AGCCGTTGATTTCTCATTATCCAAA | Nb-pds3-2 off target |
| | 5 MISMATCHES | | |
| 29 | 3623076-16-F | ACAGATCATATGGGTGTGTCTTCGA | Nb-pds3-2 off target |
| 30 | 3623076-16-R | GATGAAGGAAGCAGTATCCCTAGCA | Nb-pds3-2 off target |
| 31 | 3623321-16-F | CGCGTAAAGATAAAGTGAGCGGATA | Nb-pds3-2 off target |

TABLE 2-continued

| SEQ ID NO: | PRIMER NAME | SEQUENCE (5'-3') | Usage |
|---|---|---|---|
| 32 | 3623321-16-R | GGAGAATGGAGGTTGTGTCATCTTT | Nb-pds3-2 off target |
| 33 | 3472614-0-F | AATTGCACAATTTGACATCAAATGC | Nb-pds3-2 off target |
| 34 | 3472614-0-R | GAAACACAAGCTGACAAGAAAGCAA | Nb-pds3-2 off target |
| 35 | 2306460-16-F | CTTTGGCTTTGGAGATCCAGTAGAA | Nb-pds3-2 off target |
| 36 | 2306460-16-R | TGGAGGTAGCAGTAATCGCCATATT | Nb-pds3-2 off target |
| 37 | 3483953-0-F | TGAACATTGGAATGCTCTTCATCAT | Nb-pds3-2 off target |
| 38 | 3483953-0-R | CTATACTTCCTCAATCCCTGGGCTT | Nb-pds3-2 off target |
| 39 | 2815907-16-F | AGGACCATTTCCCTATGCCTTGTAT | Nb-pds3-2 off target |
| 40 | 2815907-16-R | GGCGACATATTAGTTCGAATGGAAG | Nb-pds3-2 off target |
| 41 | 236396-16-F | TTTCATGTCATTTGGAGGTGATTTG | Nb-pds3-2 off target |
| 42 | 236396-16-R | ACCTTAATGAAGTCCCTTGATTCCC | Nb-pds3-2 off target |
| 43 | 1395749-16-F | AGGACTTGACATGAAAGCCCAATTA | Nb-pds3-2 off target |
| 44 | 1395749-16-R | ACTCAAACGACGTAGTATCATGCCA | Nb-pds3-2 off target |
| 45 | 3655214-0-F | AGTATGGTGTTGTGAAGGAGGCATT | Nb-pds3-2 off target |
| 46 | 3655214-0-R | CTTCCAAACAGCGCTCTCTTAGAAC | Nb-pds3-2 off target |
| 47 | 649861-16-F | ATACCCTCTCAAACACTTCGTCCAG | Nb-pds3-2 off target |
| 48 | 649861-16-R | AGATTTAGTGGTGACCAGGGCATTA | Nb-pds3-2 off target |
| 49 | 977912-0-F | CTCTCAAGGTTGGAGGAACTTGAAA | Nb-pds3-2 off target |
| 50 | 977912-0-R | AAATGGGTTTCGCCATCACTAAGTA | Nb-pds3-2 off target |
| | 6 MISMATCHES | | |
| 51 | 6771578-0-F | ATGACATAATCGGAAGCAACAACCT | Nb-pds3-2 off target |
| 52 | 6771578-0-R | GCCTTGGTTTCTACAGTTCGAAAGA | Nb-pds3-2 off target |
| 53 | 28210697-16-F | AATAGGCTGAACCACTCTCACTGCT | Nb-pds3-2 off target |
| 54 | 28210697-16-R | TGGAGGCTAATTCTAAAGGAAAGGC | Nb-pds3-2 off target |
| 55 | 9388034-16-F | AGGACGGCTTCTAAGGTGCTTAGTT | Nb-pds3-2 off target |
| 56 | 9388034-16-R | TCAAGGCCTACATAGCCTTATGCTC | Nb-pds3-2 off target |

TABLE 2-continued

| SEQ ID NO: | PRIMER NAME | SEQUENCE (5'-3') | Usage |
|---|---|---|---|
| 57 | 9020645-16-F | ACACTTTGGAAGAATTTGCACATCA | Nb-pds3-2 off target |
| 58 | 9020645-16-R | TCAACTGTCGTAATGCCCAACATAC | Nb-pds3-2 off target |
| 59 | 25640405-0-F | CCGGTAACTTGGGACACCATAATAA | Nb-pds3-2 off target |
| 60 | 25640405-0-R | TTGGAAATAATCAGGATTTGGATGG | Nb-pds3-2 off target |
| 61 | 11029229-0-F | ATGAGGCATCTACACCAATTGTTCA | Nb-pds3-2 off target |
| 62 | 11029229-0-R | CTTCCTTGTTTATCATGGGTTCACC | Nb-pds3-2 off target |
| 63 | 1668194-16-F | GTGCTCCTCTGCTTATGGCTTGTAT | Nb-pds3-2 off target |
| 64 | 1668194-16-R | GTACCGGCATCTTACAACTTGCTTT | Nb-pds3-2 off target |
| 65 | 1313858-16-F | GTATGACGTCGATAATGTGGCAGAG | Nb-pds3-2 off target |
| 66 | 1313858-16-R | GAACCAATAGCATAACGACAAGGGT | Nb-pds3-2 off target |
| 67 | 6884889-16-F | AGTTGCCTCTATTGCCTTCACTTTG | Nb-pds3-2 off target |
| 68 | 6884889-16-R | GTTCTCACTTCGAGGAAAGGCATTA | Nb-pds3-2 off target |
| 69 | 9019907-0-F | ATGATGGTGTGATCAGGAGATGTGT | Nb-pds3-2 off target |
| 70 | 9019907-0-R | GACCAATCAATTCAATTTGCATTGA | Nb-pds3-2 off target |
| 71 | 24706946-16-F | GTTTGGTGCAATAAGAACTGAACCC | Nb-pds3-2 off target |
| 72 | 24706946-16-R | AACATCTCCAACCTCACTTCTTTCG | Nb-pds3-2 off target |
| 73 | 8645480-0-F | TCTCCGAGAACTCTCCTGAATCACT | Nb-pds3-2 off target |
| 74 | 8645480-0-R | TGTACTACGTGAAACATGTTGGGCT | Nb-pds3-2 off target |
| 75 | 12205859-0-F | TTAAGTGCTTGACATACCAGCCTCA | Nb-pds3-2 off target |
| 76 | 12205859-0-R | GCCTTCTTCCTTCTCTTCCTCAATT | Nb-pds3-2 off target |
| 77 | 10568921-16-F | AACACTTCGATTAAGGACGATTGGA | Nb-pds3-2 off target |
| 78 | 10568921-16-R | AAACCTGGACCGTTGATCAAATAGA | Nb-pds3-2 off target |
| 79 | 10857750-0-F | ACTGACACCGTCTGGTAGAAGGACT | Nb-pds3-2 off target |
| 80 | 10857750-0-R | TGTCCACTCCTCAACGATATCACAT | Nb-pds3-2 off target |
| 81 | 1710512-16-F | AGAAGGCCTAGTGACTCTGCTTGAA | Nb-pds3-2 off target |

TABLE 2-continued

| SEQ ID NO: | PRIMER NAME | SEQUENCE (5'-3') | Usage |
|---|---|---|---|
| 82 | 1710512-16-R | CTCATCTCGAGCATCAACATCATCT | Nb-pds3-2 off target |
| 83 | 599232-16-F | AATATCTTTGTTCCTGGTCAGCCAA | Nb-pds3-2 off target |
| 84 | 599232-16-R | TAAATGCATTTCAGGCTGGAAACTT | Nb-pds3-2 off target |
| 85 | 2639758-0-F | TCCATATTTCTGATTCGCGGACTAT | Nb-pds3-2 off target |
| 86 | 2639758-0-R | TTTGTAACTTGTCCGAGCCTCTTTC | Nb-pds3-2 off target |
| | 7 MISMATCHES | | |
| 87 | 161845497-16-F | TTGGGATTGTGATCCGAATAACTCT | N b-pds3-2 off target |
| 88 | 161845497-16-R | GCATATTCCGACCGAATAGTCTACG | N b-pds3-2 off target |
| 89 | 66367769-0-F | TATTTGGAATCCAAGCCCTTCAGTA | Nb-pds3-2 off target |
| 90 | 66367769-0-R | TGAAGGCATGCATTTCATTAAGTTG | Nb-pds3-2 off target |
| 91 | 60631893-16-F | GAAGAGTTCGAAGCCAGTCAAGAAG | Nb-pds3-2 off target |
| 92 | 60631893-16-R | TGACAGACAAAGATCATCACTGCAG | Nb-pds3-2 off target |
| 93 | 5303471-16-F | GCTCATAAACTCACCCTAAAGGCAA | Nb-pds3-2 off target |
| 94 | 5303471-16-R | ACCCTTCGGGAATTGGTATCACTAT | Nb-pds3-2 off target |
| 95 | 23533037-16-F | ACCCAGACTAGGAAATGCTTCTCCT | Nb-pds3-2 off target |
| 96 | 23533037-16-R | TCGCAAATCATATTGCTTAAGAACA | Nb-pds3-2 off target |
| 97 | 13305716-0-F | CTCGTACTCGGCTTCGTTGTTAGTT | Nb-pds3-2 off target |
| 98 | 13305716-0-R | CTCTCTCTAGGTTCATCTCGCGATC | Nb-pds3-2 off target |
| 99 | 110292002-16-F | CATGGTTTGCTGATGTTTCCAATTA | Nb-pds3-2 off target |
| 100 | 110292002-16-R | GCTCTAACTCGACCGTAAGATGGAA | Nb-pds3-2 off target |
| 101 | 58328972-0-F | TAACATAGACACGTGAAACATCGGG | Nb-pds3-2 off target |
| 102 | 58328972-0-R | TCTTTGACATGGTCAGACTGCTTTC | Nb-pds3-2 off target |
| 103 | 109561616-16-F | CCTAGAATGCGGTGGATCAGATTAC | N b-pds3-2 off target |
| 104 | 109561616-16-R | ACCAACATTATCATGGTCAAGGACA | N b-pds3-2 off target |
| 105 | 118708061-0-F | ATTCTAGCTGAACTTGCAGAGGATG | Nb-pds3-2 off target |
| 106 | 118708061-0-R | TATAAACGTTTGTCTCAACAGTCCC | Nb-pds3-2 off target |

TABLE 2-continued

| SEQ ID NO: | PRIMER NAME | SEQUENCE (5'-3') | Usage |
|---|---|---|---|
| 107 | 2542427-16-F | ATGTTTGGCAACGAGAAAGAATCTC | Nb-pds3-2 off target |
| 108 | 2542427-16-R | ACATAATCAGATCAGTGGTCGTGGA | Nb-pds3-2 off target |
| 109 | 73089692-16-F | CCACATTTAGGAATGATGCGACATA | Nb-pds3-2 off target |
| 110 | 73089692-16-R | TCTGCTCTCCTTATCGTTCGAGTCT | Nb-pds3-2 off target |
| 111 | 7004096-16-F | GAATGGAAGGGAAATAGTGTTGTGC | Nb-pds3-2 off target |
| 112 | 7004096-16-R | GATCCTCCCTATTCCGCGAATATAC | Nb-pds3-2 off target |
| 113 | 18989987-16-F | TCGATAAGTCTGATACCGACGGTTT | Nb-pds3-2 off target |
| 114 | 18989987-16-R | TCACTTACTGCTTCATTGATGGAGG | Nb-pds3-2 off target |
| 115 | 59347010-16-F | AGTATATTCAATTGCGCTCACTGGG | Nb-pds3-2 off target |
| 116 | 59347010-16-R | GTGCTATGTTGAGCTGAGACATGCT | Nb-pds3-2 off target |
| 117 | 19927971-16-F | AGATGAAGCATTTGACATGTGCATT | Nb-pds3-2 off target |
| 118 | 19927971-16-R | TGGAAGAACTTGTTCCATCACATGT | Nb-pds3-2 off target |
| 119 | 61274140-0-F | GACTTGACAAGTGGGACCCATTAAC | Nb-pds3-2 off target |
| 120 | 61274140-0-R | ATTTGACGTGGATCAGTTGCAAGTA | Nb-pds3-2 off target |
| 121 | 2246445-16-F | CTACAGGGACCTGAACAAAGCAAGT | Nb-pds3-2 off target |
| 122 | 2246445-16-R | CAACTTAAATATGAGCTCGCACGTG | Nb-pds3-2 off target |

Example 8

TABLE 3

Somatic and germline mutations in *Arabidopsis* plants infected with TRV

| | | GFP+ Plant | | Next Generation Seedlings | | | |
|---|---|---|---|---|---|---|---|
| TRV2 Vector | Plant ID | Phenotype | NHEJ | Seeds screened | GUS + | NHEJ PCR | SSA PCR |
| TRV2-sgP::Zif268:FokI:T2A:GFP | 1.1 | ++++ | D | 1120 | 4 | 0/120 | 0/120 |
| | 1.2 | ++++ | ND | 600 | 0 | | |
| | 1.3 | ++++ | ND | 300 | 0 | | |
| | 1.4 | ++++ | ND | 800 | 0 | | |
| | 2.1 | ++ | ND | 200 | 0 | | |
| | 2.2 | ++ | D | 200 | 0 | 0/47 | 0/47 |
| | 2.3 | ++ | ND | 200 | 0 | | |
| | 3.1 | ++ | N/A | 50 | 0 | | |
| | 3.2 | +++ | N/A | 1300 | 0 | | |
| | 3.3 | ++++ | ND | 1250 | 0* | | |
| | 3.4 | ++ | D | 200 | 1 | | |
| | 3.5 | ++ | ND | 100 | 0 | | |

TABLE 3-continued

Somatic and germline mutations in *Arabidopsis* plants infected with TRV

| TRV2 Vector | GFP+ Plant | | | Next Generation Seedlings | | | |
|---|---|---|---|---|---|---|---|
| | Plant ID | Phenotype | NHEJ | Seeds screened | GUS + | NHEJ PCR | SSA PCR |
| | 3.6 | +++ | ND | 1100 | 0 | | |
| | 3.7 | +++ | ND | 950 | 0 | | |
| | 3.8 | + | N/A | 0 | N/A | | |
| | 3.9 | + | N/A | 0 | N/A | | |
| | 3.10 | ++++ | N/A | 930 | 0 | | |
| | 3.11 | ++ | N/A | 20 | 0 | | |
| TRV2-sgP::Zif268:FoklΔ:T2A:GFP | 1.1 | ++++ | N/A | 600 | 0 | | |
| | 1.2 | ++++ | N/A | 800 | 0 | | |
| | 1.3 | ++++ | N/A | 400 | 0 | | |
| | 1.4 | ++++ | N/A | 500 | 0 | | |
| | 3.1 | ++++ | ND | 680 | 0* | | |
| | 3.2 | ++++ | ND | 550 | 0 | | |
| TRV2-sgP:GFP | 3.1 | ++++ | ND | 800 | 0 | | |
| | 3.2 | ++++ | N/A | 800 | 0 | | |
| | 3.3 | ++++ | N/A | 600 | 0 | | |
| | 3.4 | ++++ | N/A | 610 | 0 | | |
| Non-Infiltrated Control | | | | 10500 | 0 | | |

Plants were infected with a TRV construct expressing a Zif268:FokI ZFN and GFP separated by the T2A translational skipping sequence (TRV2-sgP:Zif268:FokI:T2A:GFP). GFP fluorescence served as a measure of virus spread through the plant. The control construct (TRV2-sgP:Zif268:FokIΔ:T2A:GFP) had an inactive FokI nuclease and served as a negative control. TRV2-sgP:GFP was an additional negative control D, detected a cleavage-resistant product; ND, did not detect a cleavage-resistant product; N/A, did not test. ++++, wild type phenotype; +++, mild phenotype: slightly stunted growth; ++, moderate phenotype: plants were noticeably smaller than controls, produced lower numbers of seeds; +, severe phenotype: stunted growth, no seeds produced. *found two seedlings with blue roots. Plants 3.8 and 3.9 did not produce seed.

The invention claimed is:

1. A method for making a heritable genomic modification at a target site in the genome of one or more plant germline cells, the method comprising
delivering a Tobacco Rattle Virus RNA2 (TRV2) T-DNA vector comprising a pea early browning virus (PEBV) promotor operably linked to a nucleic acid sequence encoding a single guide RNA (sgRNA) and a Tobacco Rattle Virus RNA1 (TRV1) T-DNA vector to one or more plant cells of a whole transgenic plant, and expression thereof to form recombinant Tobacco Rattle Virus, and
allowing recombinant Tobacco Rattle Virus infection of, and sgRNA expression in, one or more germline cells of the plant expressing a heterologous Cas endonuclease from a stably integrated genomic construct encoding the Cas endonuclease, wherein the sgRNA and Cas endonuclease form a complex and introduce a single or double strand break at a target site in the genome of the germline cell or cells leading to a heritable genomic modification.

2. The method of claim 1, wherein the construct comprises a heterologous nucleic acid encoding a Cas9 endonuclease operably linked to a promoter.

3. The method of claim 2, wherein the heterologous nucleic acid encoding the Cas9 endonuclease is a plant optimized nucleic acid sequence.

4. The method of claim 1, wherein delivery of the RNA2 (TRV2) T-DNA vector to the plant cell or cells comprises infiltrating the cell or cells with bacteria comprising the RNA1 (TRV2) T-DNA vector.

5. The method of claim 1, wherein delivery of the RNA1 (TRV1) T-DNA vector to the plant cell or cells comprises infiltrating the cell or cells with bacteria comprising the RNA1 (TRV1) T-DNA vector.

6. The method of claim 1, further comprising delivering to the plant cell or cells a heterologous donor DNA, wherein the heterologous donor DNA comprises a polynucleotide of interest to be incorporated into the genome of the plant cell.

7. The method of claim 5, wherein the bacteria is an *Agrobacterium*.

8. The method of claim 1, further comprising delivering to the plant cell or cells one or more additional RNA2 (TRV2) T-DNA vectors, wherein each additional RNA2 (TRV2) T-DNA vector encodes a different sgRNA.

9. The method of claim 8, wherein delivery of the one or more additional RNA2 (TRV2) T-DNA vectors to the plant cell or cells comprises infiltrating the cell or cells with bacteria comprising the additional RNA2 (TRV2) T-DNA vector(s).

10. The method of claim 1, further comprising selecting seeds comprising the heritable genomic modification.

11. The method of claim 10, further comprising growing a plant or plants from one or more of the selected seeds.

12. The method of claim 4, wherein the bacteria is an *Agrobacterium*.

13. The method of claim 4, wherein the bacteria is *Agrobacterium tumefaciens*.

14. The method of claim 5, wherein the bacteria is *Agrobacterium tumefaciens*.

15. The method of claim 1, wherein the modification comprises at least one deletion or substitution of one or more nucleotides in the target site.

16. The method of claim 8, comprising modifications at two or more target sites.

17. The method of claim 16, wherein the two or more modifications each comprise at least one deletion or substitution of one or more nucleotides in the target site.

18. The method of claim 1, wherein a double strand break is introduced.

19. The method of claim 1, wherein the Cas endonuclease is a nickase.

20. The method of claim 1, wherein the PEBV promoter comprises the PREV promoter sequence of SEQ ID NO:8.

\* \* \* \* \*